(12) United States Patent
Tillim

(10) Patent No.: US 6,944,914 B2
(45) Date of Patent: Sep. 20, 2005

(54) HANDLE AND FORCEPS/TWEEZERS AND METHOD AND APPARATUS FOR DESIGNING THE LIKE

(76) Inventor: Stephen L. Tillim, 11730 Magdalena Ave., Los Altos, CA (US) 94024

( * ) Notice: Subject to any disclaimer, the term of this patent is extended or adjusted under 35 U.S.C. 154(b) by 0 days.

(21) Appl. No.: 10/420,872

(22) Filed: Apr. 23, 2003

(65) Prior Publication Data

US 2004/0078935 A1 Apr. 29, 2004

Related U.S. Application Data

(63) Continuation-in-part of application No. 10/279,111, filed on Oct. 24, 2002, and a continuation-in-part of application No. PCT/US02/33956, filed on Oct. 24, 2002.
(60) Provisional application No. 60/330,527, filed on Oct. 24, 2001.

(51) Int. Cl.[7] .............................. B25G 1/04; A47J 45/00
(52) U.S. Cl. ............................. 16/430; 16/431; 16/421; 16/DIG. 12; 16/DIG. 19; 606/205; 294/99.2
(58) Field of Search ........................ 16/430, 431, 421, 16/DIG. 12, DIG. 19; 15/143, 145, 160, 257.5, 257.6; 30/232, 295, 308, 340, 341; 33/1 G, 510–512, 514.2; 173/162.1, 162.2, 169, 170; 81/177.1, 177.8, 174.5, 489; 74/551.1, 551.9, 553, 557; 482/47, 49, 44, 128; 606/205–207; D8/303, 313, DIG. 1, DIG. 6, DIG. 7, 61, 68, 80, 107; D7/649; D22/118; 294/1.1, 8.5, 11, 16, 25, 27.1, 28, 31.1, 33, 99.1, 99.2, 106, 902

(56) References Cited

U.S. PATENT DOCUMENTS

| 288,096 A | 11/1883 | Morgan |
|---|---|---|
| 336,540 A | 2/1886 | Wyttenbach |
| 340,382 A | 4/1886 | Smith |
| 700,492 A | 5/1902 | Henstock |
| 825,985 A | 7/1906 | Schwertenberg |
| 987,095 A | 3/1911 | Bonta |
| D43,242 S | 11/1912 | Bernstein |

(Continued)

OTHER PUBLICATIONS

International Search Report dated Feb. 28, 2005.
International Search Report dated Nov. 29, 2004.
International Search Report dated Jul. 14, 2004.
Result of Patent Search on "parallel grip" on USPTO website.
"Jamar Dynamometer", North Coast Medical, Inc., San Jose, CA 95125.
"Grotenhuis Endoscopic Fenestration System developed in cooperation with J. A. Grotenhuis, M.D.," Synergetics, Inc., 1998, one page.

(Continued)

*Primary Examiner*—Chuck Y. Mah
(74) *Attorney, Agent, or Firm*—Reed Smith LLP; Stanley P. Fisher, Esq.; Juan Carlos A. Marqueaz, Esq.

(57) ABSTRACT

The present invention provides a design method and apparatus for a handle providing a shape and structure that fills various regions of the hand except a region in an area over the underlying carpal tunnel. Such design method and apparatus provides for various handles for use by a hand. In particular, the apparatus includes a generally Y-shaped configuration, such as for a forceps/tweezers handle with a working end. The handle can include a radial section, an ulnar section and middle section. The handle also can have a radial arm, an ulnar arm and distal leg, with an ulnar end and a radial end for engaging a portion of the hand.

113 Claims, 32 Drawing Sheets

U.S. PATENT DOCUMENTS

| | | |
|---|---|---|
| 1,188,394 A | 6/1916 | Bernstein |
| 1,229,658 A | 6/1917 | Sandow |
| 1,648,354 A | 11/1927 | Lied |
| 1,879,456 A | 9/1932 | Parsons |
| 1,919,968 A | 7/1933 | Trabold |
| 2,047,635 A * | 7/1936 | Johst .................... 16/435 |
| 2,370,026 A | 2/1945 | Elia |
| 2,540,255 A | 2/1951 | Graves |
| 2,561,941 A | 7/1951 | Moskowitz |
| 2,621,688 A | 12/1952 | Wales |
| 2,669,991 A | 2/1954 | Curutchet |
| 2,669,993 A | 2/1954 | Curutchet |
| 2,975,505 A | 3/1961 | Linskey et al. |
| 3,129,939 A | 4/1964 | Stock |
| 3,407,816 A | 10/1968 | Curutchet |
| 3,557,792 A | 1/1971 | Rubin |
| 3,713,350 A | 1/1973 | Brilando |
| 3,741,665 A | 6/1973 | Smagala-Romanoff |
| 3,972,333 A | 8/1976 | Leveen |
| 4,043,343 A | 8/1977 | Williams |
| 4,127,338 A | 11/1978 | Laybourne |
| 4,161,051 A | 7/1979 | Brodwin |
| 4,413,034 A * | 11/1983 | Anderson .................... 428/172 |
| 4,462,404 A | 7/1984 | Schwarz et al. |
| 4,553,746 A | 11/1985 | Lee |
| 4,572,227 A | 2/1986 | Wheeler |
| 4,599,915 A | 7/1986 | Hlavac et al. |
| 4,599,920 A | 7/1986 | Schmid |
| 4,632,383 A | 12/1986 | Tsuzuki |
| 4,641,857 A | 2/1987 | Gailiunas |
| 4,644,651 A | 2/1987 | Jacobsen |
| 4,674,330 A | 6/1987 | Ellis |
| 4,674,501 A | 6/1987 | Greenberg |
| D292,297 S | 10/1987 | Bingham |
| 4,738,158 A | 4/1988 | Christol |
| 4,785,495 A | 11/1988 | Dellis |
| 4,798,377 A | 1/1989 | White |
| 4,802,704 A * | 2/1989 | Burns ................. 294/99.2 |
| 4,830,002 A | 5/1989 | Semm |
| 4,850,355 A | 7/1989 | Brooks et al. |
| 4,877,280 A * | 10/1989 | Milano ................. 294/99.2 |
| 4,885,818 A | 12/1989 | Arterbury |
| 4,899,618 A | 2/1990 | Christol |
| 4,924,851 A | 5/1990 | Ognier et al. |
| 4,941,460 A | 7/1990 | Working |
| 4,962,747 A | 10/1990 | Biller |
| 5,002,561 A | 3/1991 | Fisher |
| 5,005,674 A | 4/1991 | Piatt |
| 5,024,119 A | 6/1991 | Linden |
| 5,031,640 A | 7/1991 | Spitzer |
| 5,044,058 A * | 9/1991 | Voss ................. 29/278 |
| 5,046,381 A | 9/1991 | Mueller |
| 5,046,722 A | 9/1991 | Antoon |
| 5,047,046 A | 9/1991 | Bodoia |
| 5,047,049 A | 9/1991 | Salai |
| 5,076,569 A | 12/1991 | Gootter |
| 5,125,878 A | 6/1992 | Wingate et al. |
| 5,143,463 A | 9/1992 | Pozil et al. |
| 5,146,809 A | 9/1992 | Ruana |
| 5,146,810 A | 9/1992 | Mueller |
| 5,147,380 A | 9/1992 | Hernandez et al. |
| 5,159,851 A | 11/1992 | Rahmes |
| 5,160,343 A | 11/1992 | Brancel et al. |
| 5,176,696 A | 1/1993 | Saunders |
| 5,184,625 A | 2/1993 | Cottone, Jr. et al. |
| 5,199,324 A | 4/1993 | Sain |
| 5,211,655 A | 5/1993 | Hasson |
| 5,230,704 A | 7/1993 | Moberg et al. |
| 5,234,460 A | 8/1993 | Stouder, Jr. |
| D339,468 S | 9/1993 | Mertz |
| 5,277,683 A | 1/1994 | Wilkins |
| 5,299,991 A | 4/1994 | Sato |
| 5,318,589 A | 6/1994 | Lichtman |
| 5,339,850 A | 8/1994 | Mertz |
| 5,351,702 A | 10/1994 | Denjean |
| 5,366,476 A | 11/1994 | Noda |
| 5,379,758 A | 1/1995 | Snyder |
| 5,391,010 A | 2/1995 | Gorbunov |
| 5,417,234 A | 5/1995 | Davis |
| 5,445,479 A | 8/1995 | Hillinger |
| 5,454,380 A | 10/1995 | Gates |
| 5,470,162 A | 11/1995 | Rubin |
| 5,470,328 A | 11/1995 | Furnish et al. |
| 5,495,867 A | 3/1996 | Block |
| 5,498,256 A | 3/1996 | Furnish |
| 5,522,290 A | 6/1996 | Visser et al. |
| 5,540,304 A | 7/1996 | Hawkins et al. |
| 5,554,132 A | 9/1996 | Straits et al. |
| 5,556,092 A | 9/1996 | Theken |
| 5,562,693 A | 10/1996 | Devlin et al. |
| 5,571,127 A | 11/1996 | DeCampli |
| 5,578,050 A | 11/1996 | Webb |
| 5,606,985 A | 3/1997 | Battiston et al. |
| 5,634,382 A | 6/1997 | Fan |
| 5,653,713 A | 8/1997 | Michelson |
| 5,659,959 A | 8/1997 | Parlowski |
| 5,660,082 A | 8/1997 | Hsieh |
| 5,662,006 A | 9/1997 | Angeltun |
| 5,692,265 A | 12/1997 | Dalury |
| 5,728,121 A | 3/1998 | Bimbo et al. |
| 5,730,751 A | 3/1998 | Dillon et al. |
| 5,735,873 A | 4/1998 | MacLean |
| 5,761,767 A | 6/1998 | Barton |
| 5,782,853 A | 7/1998 | Zeevi et al. |
| 5,785,443 A | 7/1998 | Rubin |
| 5,791,671 A | 8/1998 | Tang et al. |
| 5,797,165 A | 8/1998 | Armbrust |
| 5,797,900 A | 8/1998 | Madhani et al. |
| 5,827,263 A * | 10/1998 | Furnish et al. ................. 606/1 |
| 5,829,099 A | 11/1998 | Kopelman et al. |
| 5,830,231 A | 11/1998 | Geiges, Jr. |
| 5,833,580 A | 11/1998 | Chiu |
| 5,846,221 A | 12/1998 | Snoke et al. |
| 5,885,018 A | 3/1999 | Sato |
| 5,893,877 A | 4/1999 | Gampp, Jr. et al. |
| 5,897,571 A | 4/1999 | Kazama |
| 5,908,432 A | 6/1999 | Pan |
| 5,920,944 A | 7/1999 | Biggs et al. |
| 5,923,467 A | 7/1999 | Pericic et al. |
| 5,935,149 A | 8/1999 | Ek |
| 5,961,430 A | 10/1999 | Zuckerman et al. |
| 5,976,121 A | 11/1999 | Matern et al. |
| 5,979,015 A | 11/1999 | Tamaribuchi |
| 5,980,511 A | 11/1999 | Bilitz et al. |
| 5,991,956 A | 11/1999 | Chapman |
| 6,007,570 A | 12/1999 | Sharkey et al. |
| 6,012,623 A | 1/2000 | Fealey |
| 6,024,737 A | 2/2000 | Morales |
| 6,029,780 A | 2/2000 | Phillips |
| 6,030,409 A | 2/2000 | Lang |
| 6,041,258 A | 3/2000 | Cigaina et al. |
| 6,042,559 A | 3/2000 | Dobak, III |
| 6,063,087 A | 5/2000 | Agee et al. |
| 6,079,523 A | 6/2000 | Irvine |
| 6,085,611 A | 7/2000 | Valdez |
| 6,094,780 A | 8/2000 | McGlothlin et al. |
| 6,119,309 A | 9/2000 | Lu |
| 6,129,622 A | 10/2000 | Seaman et al. |
| 6,129,740 A | 10/2000 | Michelson |
| 6,134,994 A | 10/2000 | Gomas |
| 6,145,151 A | 11/2000 | Herron et al. |

| | | |
|---|---|---|
| 6,161,256 A | 12/2000 | Quiring et al. |
| 6,161,974 A | 12/2000 | Nakagawa |
| 6,217,536 B1 | 4/2001 | Gustafson |
| 6,305,244 B1 | 10/2001 | Takahama |
| 6,354,618 B1 | 3/2002 | Liao |
| 6,427,565 B1 | 8/2002 | Ping |
| 6,530,125 B2 | 3/2003 | Shippert |
| 6,592,160 B1 | 7/2003 | Nicolay et al. |
| 6,637,962 B1 | 10/2003 | Roche et al. |
| 2001/0001630 A1 | 5/2001 | Nakagawa |

OTHER PUBLICATIONS

"Reverse Cut Diamond Arachnoid Knife developed with James E. Benecke, M.D.," Synergetics, Inc., 1996, one page.

"Deep Neuro Dissection Set," Synergetics, Inc., 1996, two pages.

"Dacey TruMicro Vertical Scissors," Synergetics, Inc., 1998, four pages.

"Skull Base Instruments developed with James E. Benecke, M.D.", Synergetics, Inc., 1996, two pages.

"Spetzler TruMicro Scisssors," Synergetics, Inc., 1998, two pages.

"Spetzler TruMicro Pituitary & Micro Cup Forceps," Synergetics, Inc., 1998, two pages.

"Spetzler Microsurgical Set," Synergetics, Inc., 1999, one page.

"Dacey Microvascular Repair Instruments developed in cooperation with Ralph G. Dacey, Jr., M.D.," Synergetics, Inc., 1996, two pages.

Photocopy of Carpal Lock, 2000, one page, Working, U.S. Pat. No. 4,941,460.

Splints, Dynamic Splints, Hand Splints, AliMed Catalog, 2000, pp. D25, D26, D29 and D30.

Web site brochure for Ergo Pen, 1999, five pages.

Steering Wheels and Quick Release Hubs, Pegasus Catalog, 2000, p. 107.

"Guide to the 2000 SAP U.S. Grand Prix", Road & Track, 2000, cover page, pp. 16 & 18, three advertisement pages for Ferrari, Kumo tires, and Suzuki.

Illustration of hammer in article entitled "Quake insurance is less of a bargain but it's still a good investment", San Jose Magazine, 2001, two pages.

"Carpal Tunnel Syndrome Strike Many, Easy to Treat", American Association of Neurological Surgeons, 2000, two pages.

Results of EAST patent search, re: Ergonomics, 2 pages, search performed in 2000.

Results of EAST patent search re: Medical Instruments, 15 pages, search performed in 2000.

Results of EAST patent search re: Pen, 1 page, search performed in 2000.

Result of Assignee patent search re: Synergetics patents, 2 pages, search performed in 2000.

"Hand Grip to Prevent and Alleviate Carpal Tunnel Syndrome", USPTO Disclosure Document No. 321372, filed Dec. 4, 1992, 3 pages and 1 page of PTOL–362 form.

* cited by examiner

HANDLE AND FORCEPS/TWEEZERS AND METHOD AND APPARATUS FOR DESIGNING THE LIKE

CLAIM FOR PRIORITY

This application claims the benefit of and is a Continuation-In-Part of U.S. application Ser. No. 10/279,111 filed on Oct. 24, 2002, the entire disclosure of which is incorporated herein by reference; this application also claims the benefit of and is a Continuation-In-Part of International Application No. PCT/US02/33956, filed on Oct. 24, 2002, presently published in English under PCT Article 21(2), the entire disclosure of which is incorporated herein by reference; and this application further claims the benefit of U.S. Provisional Patent Application Ser. No. 60/330,527 filed on Oct. 24, 2001, the entire disclosure of which is incorporated herein by reference.

FIELD OF INVENTION

The present invention provides handles for forceps/tweezers and method and apparatus for designing such handles. Desirably, the forceps/tweezers have a generally asymmetrical "Y" shaped handle designed to comfortably fit the hand when used. The present invention provides a forceps/tweezers handle that desirably includes two mirror image blades, which meet or connect at one end. The forceps/tweezers handle of the present invention can be used as a handle to assist the hand in pinching, gripping, holding, cutting and other functions. The forceps/tweezers handle of the present invention can be used for surgical forceps, a variety of surgical instruments, tweezers and a variety of tools and instruments.

BACKGROUND OF THE INVENTION

Forceps and tweezers are common tools made in the shape of a stylus in which there is a working end or tip and a part that rests on the fleshy space between the base of the index finger and the thumb. Typically, forceps and tweezers are held like a pencil where the thumb, index finger and middle finger hold forceps or tweezers close to the working end. As used herein and as in human anatomy, the anatomical term proximal is nearer and distal is further away on the extremities in relation to the torso. Similarly, in relation to the hand, typically the part of a forceps or tweezers resting over the portion of the hand between the base of the thumb and index finger is the proximal end, whereas the tips of forceps or tweezers can be referred to as the distal end.

Forceps and tweezers have opposing blades or members and fine tips enabling the hand to pick up and hold parts of various objects with a range of grip intensity. The opposing actions of the thumb and the long fingers manipulate the blades to move the tips of forceps or tweezers together. Opposition, i.e. moving the tip of the thumb and tips of the long fingers closer to each other, is done by contracting opponens muscle of the thumb and the lumbrical muscles of the long fingers. The lumbricals are small muscles located in the palm of the hand and their contraction pulls the proximal interphalangeal (PIP) bones at the base of the long fingers. The opponens muscle of the hand pulls the base of the thumb. When using forceps or tweezers, the function of fine pinch is under control of the opponens muscle and the lumbrical muscles. However, the function of gross pinch is under control of the opponens muscle of the forearm that pulls the distal portion of the thumb, and the deep flexor muscles of the forearm pull the distal portion of the index finger and the distal portion of the middle finger.

Typically, the blades of a forceps or tweezers receive support in the resting hand from the middle finger that crosses underneath them and the portion of the hand between the thumb and index finger. However, when the distal tips of a forceps or tweezers are moved together, the support for the forceps or tweezers in the hand changes and greater support is generated at the tips of the thumb and index fingers to hold the forceps or tweezers. This can cause muscle and joint strain.

Some of the factors that can cause strain in the hand when using a common forceps or tweezers include the width of the blades, the spring force of the blades, the way the hand and wrist joints function when grasping or pinching with a forceps or tweezers, the number of muscle fascicles of a muscle used to contract a corresponding muscle, and the position of the fingers on the forceps or tweezers. Typically, wider blades of a forceps or tweezers are easier to hold than narrow blades, and generally require less muscle tension to pinch. The spring-like properties of the material used for typical forceps or tweezers and the connection of the blades can affect the muscle force required to close a forceps or tweezers.

Most joints flex and extend and have a small degree of side to side motion, while other joints can move in more than one direction. In the latter joints, such as the thumb, there is larger surface contact area at the center of the joint than the periphery of the joint. When the thumb opposes the center of the long finger tips, the bones at the base of the thumb contact more surface area. When the thumb opposes the index finger or small finger, then bone contact in the joint is at the respective sides of the joint, with the joint contact area of the bones being less than when the thumb opposes the long fingers. Therefore, the common forceps or tweezers force the thumb to move to the radial side of the thumb joint where there is less bone contact surface area.

Muscles are made up of sub groups called muscle fascicles. These fascicles are made up of groups of muscle fibers. The amount of muscle fiber contraction determines the strength or the pinch force used to hold an object between the tips of the forceps or tweezers. When the radial side of the thumb joint is used to hold a common forceps or tweezers, the thumb opposes the index finger, and the radial side of the opponens muscle contracts to pull the thumb. In the common forceps or tweezers, fewer muscle fascicles and fibers are typically used for pinch strength when the thumb opposes the index finger than when the thumb opposes the center of the long finger tips. If fewer muscle fascicles and fibers are used to pinch, than potentially available, there is a greater chance of fatigue and strain in these muscles and their fascicles. Therefore, utilizing more muscle fascicles can desirably increase pinch strength and reduce muscle fatigue and stress. Thus a forceps or tweezers that increases the number of muscle fascicles used to pinch a forceps or tweezers is desirable.

Moreover, pinch strength is also affected by the number of muscles used in pinching. When the thumb and index finger pinch, one lumbrical muscle is used to pinch the index finger against the thumb. However, two lumbrical muscles, one for the index finger and one for the middle finger, are used in pinching when the thumb opposes the space between the index finger and middle finger. Pinch forces are potentially greater when the thumb opposes both the index finger and the middle finger than when the thumb opposes the index finger alone. This potential grip strength is greater because more opponens muscle fascicles are available when the thumb opposes the space between the index finger tip and the middle finger tip than when the thumb opposes the index finger tip. Thus, opposing the thumb to the space between the index finger and the middle finger has greater efficiency and can reduce muscle fatigue.

Additionally, hand strain can occur while using a common forceps or tweezers. This is because the thumb and index finger have a natural tendency to advance toward the tip of the common forceps or tweezers when holding a stylus-type tool, creating the potential for excessive squeezing of the forceps or tweezers. This can create exaggerated flexion at the distal interphalangeal joint (DIP) of the thumb and exaggerated index finger flexion at the middle interphalangeal (MIP) joint of the index finger while the DIP joint of the index finger extends. With such exaggerated flexion, the tips of the fingers squeeze and retract proximally, providing feedback or added pressure, i.e. "the feel", that an object is being supported by the hand. Maintaining this awkward position can also strain finger and wrist joints and ligaments, especially when they suffer pre-existing damage. Such awkward but common position of exaggerated flexion results from the forearm muscles and tendons contrasting the middle phalange of the index finger and distal phalange of the thumb. This typically requires significant force from the forearm muscles, which can add strain and pressure within the carpal tunnel (CT) where the tendons of the superficial flexor forearm muscles transmit direct pressure on the transverse carpal ligament (TCL) and median nerve. Thus, the strain and pressure in the CT from the tendons of the contracted superficial flexor forearm muscles resulting from such awkward position can lead to median nerve irritation and carpal tunnel syndrome (CTS). Furthermore, strain in the muscles in the hand and forearm can cause repetitive strain syndrome of the involved muscles.

A typical problem posed with common forceps and tweezers is that frequent use can cause pain in the hand, wrist and forearm and lead to CTS. This problem has not been solved because the common forceps or tweezers generally adapts a stylus-type tool to pinch small objects. Such stylus-type tools can force the hand into an uncomfortable position with the hand compensating for exaggerated finger flexion, as discussed above, leading to this problem.

Efficiency is reached when the parts of the hand work in harmony to perform a task. The goal of handle design for a forceps or tweezers, as well as an objective of the method and apparatus of the present invention is to promote such efficiency. An efficient handle design should maintain the hand in a comfortable position. A further goal of any handle or grip design, as well as a further objective of the present invention, is to facilitate the function of the hand and forearm muscles so they work in concert. Another goal of handle design, as well as a further objective of the method and apparatus of the present invention, is to facilitate the function of the joints in the hand and wrist to reduce ligament strain.

Furthermore, another goal of handle design for a forceps or tweezers, as well as an objective of the method and apparatus of the present invention, is to promote reduced pinch strength typically required for holding an object. When less pinch strength is required to hold objects, there is less strain to joints and their surrounding ligaments.

Therefore, what is needed is a handle for a forceps or tweezers, and a method and apparatus for designing such a handle for a forceps or tweezers, that fulfills the previously mentioned goals. Such a handle for a forceps or tweezers should promote a reduced incidence of repetitive strain disorder and joint injury.

Forceps and tweezers, such as surgical forceps and tweezers, generally fall into three common types. The first type has two side by side blade members hinged at one end and tips at the other respective end. The blade members move toward each other and the tips come together to grasp and hold. The blade members of this first type of forceps and tweezers can meet and cross and then extend like a scissors. The blade members of the second type of forceps and tweezers are oriented one on top of the other instead of side by side. In the second type, the handles extend perpendicular to the orientation of the blade members and typically the handles have rings to engage the fingers. The blade members in the second type meet the handles at a hinge. Moving the ring handles moves a pivoting member to open or close for grasping or cutting tissue. A third type of forceps and tweezers uses a lever or slide to actuate a mechanism that opens and closes the jaws of an instrument.

Examples of the side-by-side blades of the first type of forceps or tweezers include those in U.S. Pat. Nos. 288,096, 987,095 and 2,540,255, which are fruit pickers. U.S. Pat. No. 5,893,877 illustrates a forceps or tweezers which is a microsurgical cup forceps. U.S. Pat. No. 5,002,561 illustrates a protective hand forceps and U.S. Pat. No. 5,176,696 is related to handles for microsurgical instruments. The handles in U.S. Pat. No. 5,176,696 oppose the thumb to the index finger and middle finger.

Examples of the ring or second type of forceps or tweezers include those illustrated in the following U.S. patents, namely U.S. Pat. No. 4,043,343 illustrates forceps, U.S. Pat. No. 4,674,501 illustrates a surgical instrument, U.S. Pat. No. 5,160,343 illustrates a surgical instrument handle and forceps assembly, U.S. Pat. No. 5,211,655 illustrates multiple use forceps for endoscopy, U.S. Pat. No. 5,234,460 illustrates laparoscopy instrument, and U.S. Pat. No. 5,318,589 illustrates a surgical instrument for endoscopic surgery.

Examples of the lever or third type of forceps or tweezers include those illustrated in the following U.S. Patents, namely U.S. Pat. No. 4,644,651 illustrates an instrument for gripping or cutting, and U.S. Pat. No. 5,470,328 illustrates a surgical instrument handle and actuator means, in which both devices described press down a lever. Other examples of the lever or third type of forceps or tweezers include those illustrated in U.S. Pat. No. 5,147,380 which illustrates a biopsy forceps device having locking means and in U.S. Pat. No. 5,184,625 which illustrates a biopsy forceps device having improved handle, both having sliding locking devices. Another example of the lever or third type of forceps or tweezers is illustrated in U.S. Pat. No. 5,976,121 as a medical manipulator that has a lever that straddles a shaft that has a distal end with a grasping part.

What is needed is a forceps or tweezers allowing the hand to pinch with greater efficiency, improved stability and reduced joint and muscle strain and tension. The problem with many of the above examples of common forceps or tweezers is that their design and operation does not take advantage of the greater pinch strength available from opposing the thumb to the index finger and middle finger instead of opposing the thumb to the index finger. Furthermore, the above styles of handles for common forceps or tweezers do not efficiently utilize the palm of the hand to support the handle. In addition, the handles for common forceps and tweezers do not efficiently utilize the ring finger and small finger to hold and stabilize the handle of the forceps and tweezers.

SUMMARY OF THE INVENTION

The present invention provides handles for forceps/tweezers and method and apparatus for designing such handles.

Also, in the design method and apparatus for handles for forceps/tweezers of the present invention, the design method and apparatus includes embodiments and methods based on measurements made of the hand in a functional pinching position or Forceps Hand Position (FHP).

A method and apparatus for designing handles for forceps/tweezers and method and apparatus for designing such handles of the present invention is provided and is based on defined anatomical positions derived from the functional anatomy of a pinching hand. The method uses lines with respect to measurements made in the hand when the thumb opposes the space between the index and middle fingers. Apparatus, such as forceps and tweezers, produced from this method make efficient use of the hand.

An advantage of handles for forceps/tweezers and method and apparatus for designing such handles of the present invention of such design is that such handles do not contact the skin over the TCL. Therefore the TCL is not compressed and no pressure is transmitted to the contents of the CT region during pinching or using a handle of such design.

Another advantage of handles for forceps/tweezers and method and apparatus for designing such handles of the present invention is that the natural arcs of the fingers and palm are maintained. In conforming to the natural hand anatomy a handle of this design becomes more comfortable to hold.

Another advantage of handles for forceps/tweezers and method and apparatus for designing such handles of the present invention is that a larger part of the hand contacts the handle. Thus there is the addition of the much greater hand area contacting a handle of this design for pinching.

Another advantage is that using such handles for forceps/tweezers and method and apparatus for designing such handles of the present invention does not compromise or distort the arteries supplying the muscles in the hand. This is because such a handle does not touch either the TCL and underlying CT where the radial artery traverses Guyon's tunnel at the pisiform bone where the ulnar artery goes deep to supply the structures of the hand.

Another advantage of handles for forceps/tweezers and method and apparatus for designing such handles of the present invention is that they do not compromise, compress or distort the nerves that go to the hand.

Another advantage of using handles for forceps/tweezers and method and apparatus for designing such handles of the present invention is that there is less strain on contents of and pressure in the CT.

Another advantage of handles for forceps/tweezers and method and apparatus for designing such handles of the present invention is that there is less compression, distortion or irritation of the median nerve by the superficial flexor tendons, which are closer to the TCL and the median nerve in the CT.

The consummate advantage is that handles for forceps/tweezers and method and apparatus for designing such handles of the present invention based on the advantages noted above will reduce acute and chronic irritation, trauma and strain to the tendons, bursa, joints, hand muscles and median nerve. It is therefore expected that the result will be in a reduced incidence of CTS and repetitive strain syndrome for people who use forceps or tweezers of this design.

It is an objective of the present invention to provide a design method and apparatus for handles for forceps/tweezers of the present invention having greater contact with the supportive areas of the hand.

It is an objective of the present invention to provide a design method and apparatus for handles for forceps/tweezers and method and apparatus for designing such handles of the present invention to optimize use of the flexor hand muscles to the thumb and long fingers.

It is still another objective of the present invention to provide a design method and apparatus for handles for forceps/tweezers and method and apparatus for designing such handles of the present invention that utilizes reduced grip strength as compared to a common forceps/tweezers.

It is still another objective of the present invention to provide handles for forceps/tweezers and method and apparatus for designing such handles of the present invention of various sizes and shapes for various applications.

It is still another objective of the present invention to provide handles for forceps/tweezers and method and apparatus for designing such handles of the present invention related to various hand sizes to accomplish the above and other objectives of the present invention.

According to a further aspect of the present invention, the distal end of handles for forceps/tweezers and method and apparatus for designing such handles of the present invention can include an elevated surface or various surfaces acting as a reference or references for positioning of the fingers on the forceps/tweezers.

According to another aspect of the present invention, handles for forceps/tweezers and method and apparatus for designing such handles of the present invention can include those desirably having generally a "Y" shape, the "Y" shape desirably being of a generally asymmetric "Y" shape. The "Y" shape for such handle for forceps/tweezers has three ends with two upper arms and one leg, either as a single "Y" shape portion or having two "Y" shaped portions joined at their respective proximal ends. While the handles for forceps/tweezers of such aspect of the present invention will generally have the two "Y" shaped portions joined or meeting at their proximal end to perform a forceps/tweezers open and close pinching function, the handle for the forceps or tweezers can also be of a single "Y" portion, that can be adapted for various mechanisms and implements, such as for a motorized control function, such as for an implement, or as can be used for a shovel, spade or pick, for example. The uppermost or proximal arm of each "Y" meets and touches areas on the radial side and ulnar side of the palm of the hand. Each leg or distal end of the "Y" extends from the corresponding connection of the radial and ulnar proximal arms of the "Y" to end near the tips of the thumb, index finger and middle finger. The lower leg or distal end of each "Y" contacts the distal part of the thumb, index finger and middle finger of the hand. In embodiments having the two "Y" shaped portions, the proximal ends of the "Y" are connected and the distal end of each "Y" moves toward the other by the opposing movement of the thumb on one "Y" and the index finger and middle finger on the other "Y". A variety of working ends/working members attached to the distal members of the handle by various means can be used to grasp, bite or cut various objects. The present invention also provides for handles, such as for forceps/tweezers, and method and apparatus for designing such handles of the present invention to be made for a plurality of hand sizes by adjusting the dimensions of the proximal arm and the dimensions of the distal leg.

According to another aspect of the present invention, handles for forceps/tweezers and method and apparatus for designing such handles of the present invention desirably provide for the thumb to oppose both the index and middle fingers, which is in contrast to the thumb opposing the index finger alone as in the common forceps or tweezers.

According to a further aspect of the present invention, handles for forceps/tweezers and method and apparatus for designing such handles of the present invention desirably provide greater stabilization because the handle for forceps/tweezers is supported at areas within the hand, rather than resting on the middle finger and the portion of the hand between the base of the thumb and index finger.

According to another aspect of the present invention, handles for forceps/tweezers and method and apparatus for designing such handles of the present invention desirably provide for maintaining the ring finger and the small finger in the T Position.

Furthermore, handles for forceps/tweezers and method and apparatus for designing such handles of the present invention desirably optimize the position for the joints of the thumb, index finger and middle finger so the respective MIP and DIP joints cannot flex excessively. Therefore, the handles for the forceps/tweezers of the present invention promote reduced demands on the forearm muscles and the hand muscles, when used for pinching.

According to a further aspect of the present invention, handles for forceps/tweezers and method and apparatus for designing such handles of the present invention can reduce or prevent injury to joints, muscles, tendons and the median nerve in the CT compartment.

According to a further aspect of the present invention, handles and method and apparatus for designing such handles of the present invention provide for power pinch that can utilize all of the digits of the hand for pinch and not the first three digits of the hand. Stress is thereby reduced at the metacarpal-carpal joint of the thumb when the thumb meets the wrist bones, as compared to when the thumb only opposes the index finger. When the thumb opposes the space at the middle of the long fingers, this position directs the stress across the four metacarpal-phalangeal joints of the index, middle, ring and small fingers. Directing stress across MP joints of the index, middle, ring and small fingers enlists more muscles for pinching.

An object of the present invention is to desirably provide handle designs that utilize the appropriate muscles to enhance pinch.

Another object of the present invention is to desirably provide handle designs that utilize the appropriate muscles for delicate pinch.

A further object of the present invention is to desirably provide handle designs that stabilize a handle within the hand.

An additional object of the present invention is to desirably provide handle designs that position the thumb to oppose the space between the index and middle fingers Moreover, another object of the present invention is to desirably provide handle designs that keep the hand in the T position where the tips of the ring finger and small finger are substantially aligned.

Likewise, an object of the present invention is to desirably provide handle designs that reduce muscle and joint tension.

Another object of the present invention is to desirably provide handle designs that limit flexion at the PIP joints of the opposing thumb, index finger and middle finger of the hand.

A further object of the present invention is to desirably provide handle designs that contact the horizontal crease on the radial side of the hand.

An additional object of the present invention is to desirably provide handle designs that contact the hypothenar muscle area between the horizontal crease on the ulnar side of the hand and the pisiform bone on the ulnar side of the hand.

It is an object of the present invention to desirably provide handle designs that position the handle in the hand by having the ring and small fingers wrap around the ulnar member of the handle.

It is another object of the present invention to desirably provide handle designs that use the flexed ring finger and small finger to pull the handle of the present invention toward the radial side and ulnar side of the palm of the hand when the hand is in the Forceps Hand Position (FHP).

It is also an object of the present invention to desirably provide handle designs that have the ring finger and the small finger direct (push/pull) the proximal part of the forceps/tweezers handle against the radial side and the ulnar side of the hand.

Moreover, it is an object of the present invention to desirably provide handle designs that prevent the handle from slipping within the hand.

Additionally, it is an object of the present invention to desirably provide handle designs that stabilize such handles used with an apparatus within the hand.

Further, an object of the present invention is to desirably provide handle designs that make the shape of the ulnar section relate to the functional position of the ring and middle fingers when the hand is in the Forceps Hand Position (FHP).

Also, an object of the present invention is to desirably provide handle designs that use the flexed ring finger to lift the handle as it contacts the the proximal portion of the distal leg of the handle when the hand is in the Forceps Hand Position (FHP).

BRIEF DESCRIPTION OF THE DRAWINGS

The foregoing and additional features and characteristics of the present invention will become more apparent from the following detailed description considered with reference to the accompanying drawings in which like reference numerals designate like elements and wherein:

FIG. 2A shows the palmar surface view with the thumb, index finger and middle finger ending in the same plane. The tips of the ring finger and small finger end on the same line as in the T Position. FIG. 2B is a view of the hand in the Forceps Hand Position (FHP) from the perspective of the radial side of the hand.

FIG. 4A is three-dimensional view. FIG. 4B is a side or profile view. FIG. 4C is a top or radial view.

FIG. 5A is a palmar view of the hand holding a forceps/tweezers handle and FIG. 5B is a radial view of the hand holding a forceps/tweezers handle.

FIG. 6A shows a palmar view of the hand with the lines to be measured. FIG. 6B shows a radial view of the hand with the lines to be measured.

FIGS. 9A and 9B illustrate variations at the ulnar arm. FIGS. 9C and 9D illustrate variations at the contact area where the thumb, index finger and middle finger can manipulate a handle of the present invention. FIGS. 9E, 9F and 9G illustrate extensions added to a handle of the present invention to adjust the handle of the present invention for a plurality of hand sizes.

FIGS. 10A and 10B illustrate an elastic means, such as a spring, to keep the handle in an open position. FIGS. 10C, 10D and 10E illustrate different views of a clamp to maintain a handle from a fully open to a fully closed position. FIGS. 10F and 10G illustrates ring members to receive the ends of corresponding fingers in a handle.

FIG. 19A illustrates a unitary handle of the present invention having a single "Y" configuration. FIG. 19B illustrates an embodiment of a generally unitary handle of the present invention having an implement attached by a suitable connection means to a handle of the present invention. FIG. 19C illustrates an embodiment of a generally unitary handle of the present invention that incorporates a motor driving means for rotation or movement of a working end or an implement. FIG. 19D illustrates an embodiment of a generally unitary handle of the present invention having a motor driving means for opening and closing a working end or ends of an implement.

DESCRIPTION OF THE PREFERRED EMBODIMENTS

In order to more clearly and concisely describe the subject matter of the present invention, the following definition for the T Position is intended to provide guidance as to the meanings of specific terms used in the following written description. In addition, it is to be understood that the phraseology or terminology employed herein is for the purpose of description and not to be construed in a limiting sense. The following discussion relates to areas of the hand in relation to the present invention with reference to FIG. 1.

T Position

Figure 1:
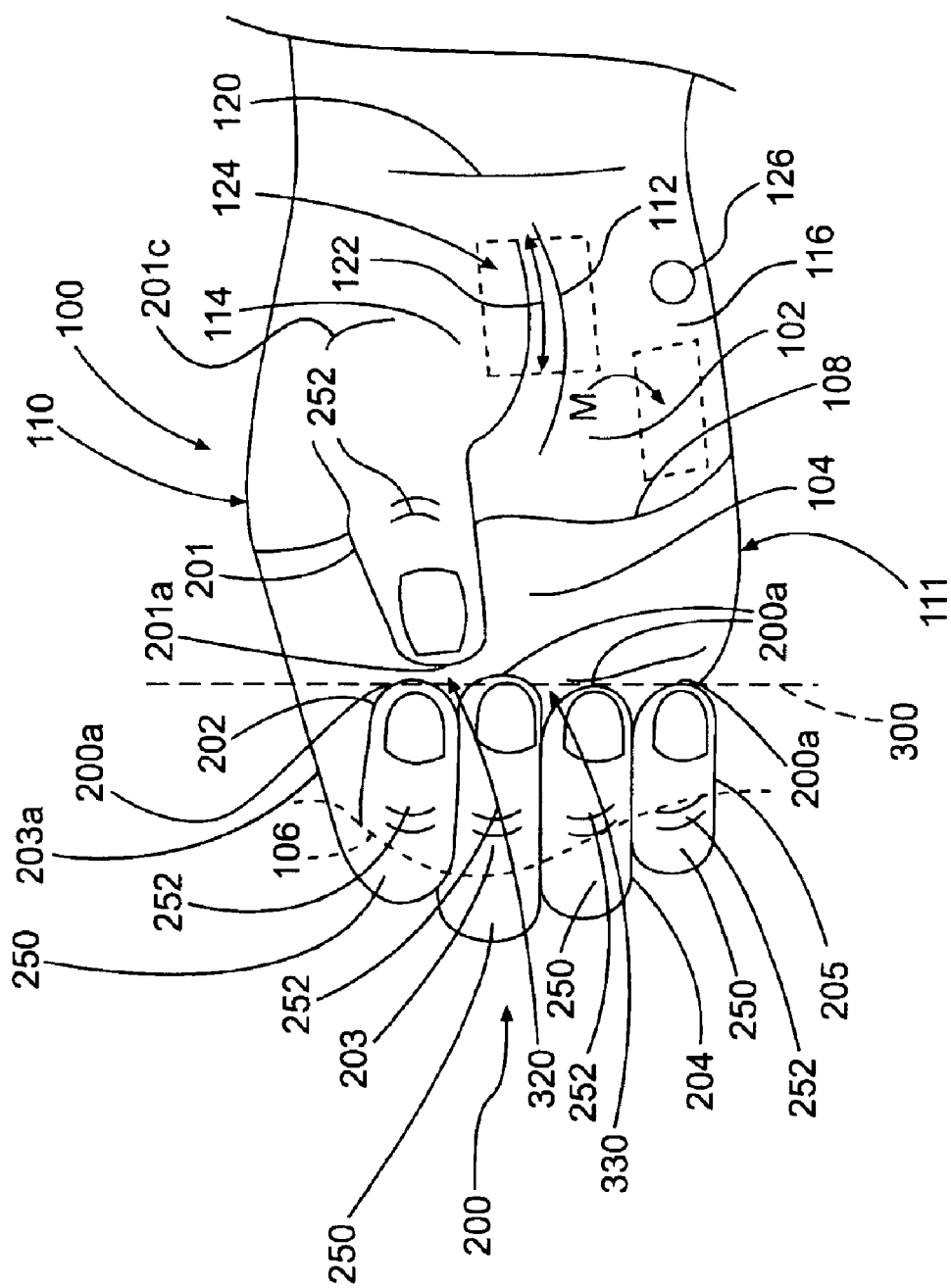
FIG. 1 is a view of the palmar side of the hand when the hand is in the T Position illustrating the long fingers ending in the same line and the thumb opposing the space between the index finger and middle finger.

FIG. 1 illustrates the hand 100 to the T Position. The T Position is the position the hand 100 assumes when the tips 200a of the long fingers 200 are aligned and the tip 201a of the thumb 201 opposes the space 320 between the index finger 202 and middle finger 203. In this position the area that crosses the palm 102 of the hand 100 known as the palmar arch 104 is concave. The finger cup 106, shown as a dotted line, is the concave area made by the long fingers 200 when the tips 200a of the long fingers 200 are aligned and the long fingers 200 are flexed. The horizontal creases 108 of the palm 102 appear as a skin fold and aligns with the palmar arch 104. On the radial side 110 of the hand 100 the horizontal crease 108 is hidden by the thumb 201. The longitudinal creases 112 also appear as a skin fold because the palm 102 of the hand 100 is not flat when the hand 100 is in the T Position. The MIP joints 250 of the long fingers 200 lie adjacent to each other. The MIP joint 250 of the middle finger 203 is furthermost away from the line 300 than the other MIP joints 250 of the other long fingers 200 are from the line 300. The MIP joint 250 of the small finger 205 is closer to the line 300 than MIP joints 250 of the other long fingers 200.

Continuing with reference to FIG. 1, the hypothenar muscle area 116 extends from the horizontal crease 108 of the ulnar side 111 of the hand 100 to the wrist 120 at the level of the pisiform bone 126. The pisiform bone 126 of the wrist 120 is at the area on the ulnar side 111 of the hand 100 where the ulnar nerve and ulnar artery enter the palm 102 under the hypothenar muscle area 116. The transverse carpal ligament (TCL) 122 covers the carpal tunnel (CT) 124. The thenar muscle area 114 is on the radial side 110 of the hand 100 and radial to the CT 124. The hypothenar muscle area 116 is on the ulnar side 111 of the hand 100 and ulnar to the CT 124. The CT 124 contains the median nerve, four tendons from the superficial flexor muscle of the forearm and four tendons from the deep flexor muscle of the forearm. The superficial tendons are closer to the inner surface of the TCL 122 than the deep tendons. This places the superficial tendons next to the median nerve.

Forceps Hand Position (FHP)

Figure 2A:
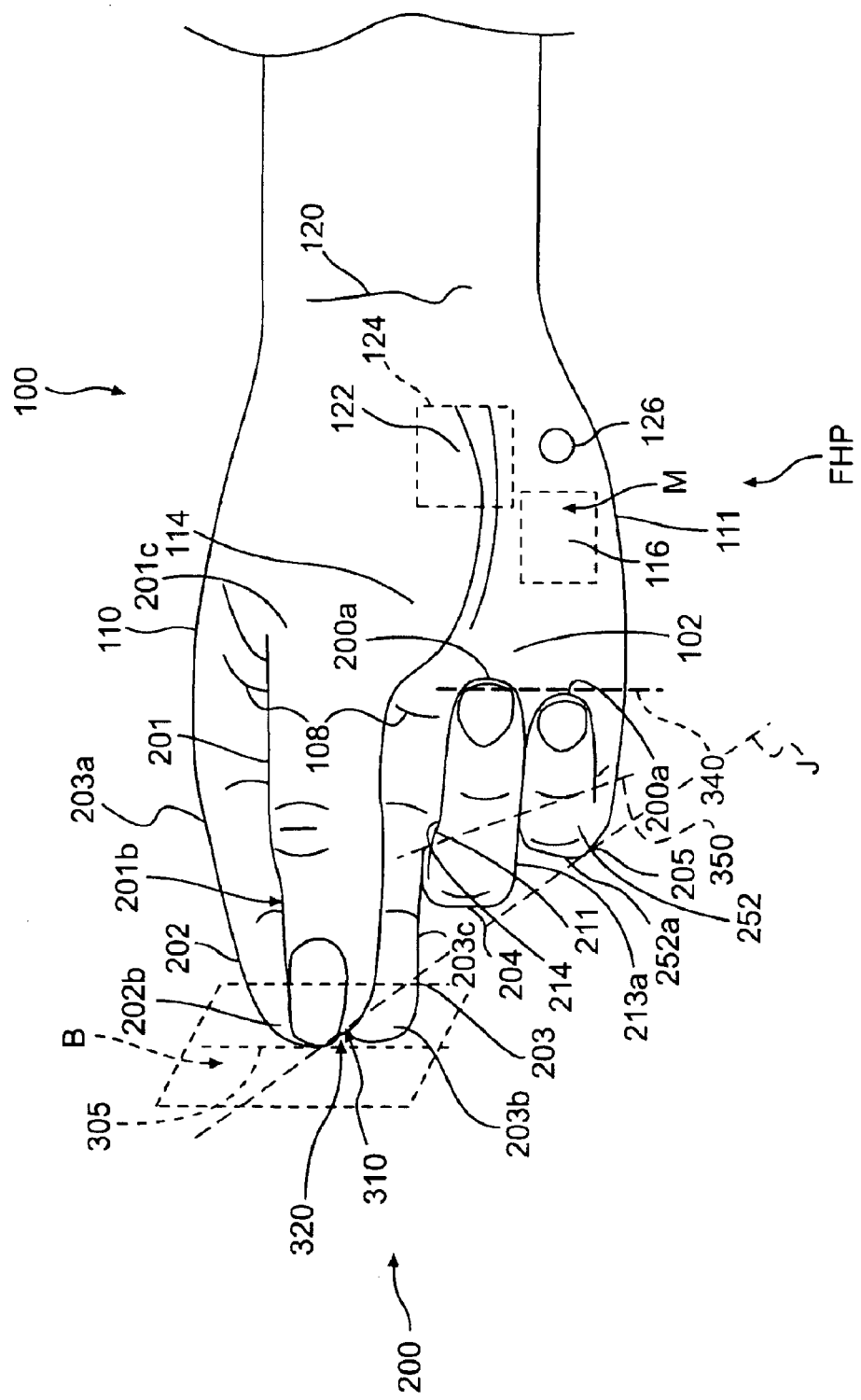
FIG. 2A and FIG. 2B are views of the hand in the Forceps Hand Position (FHP).
Figure 2B:
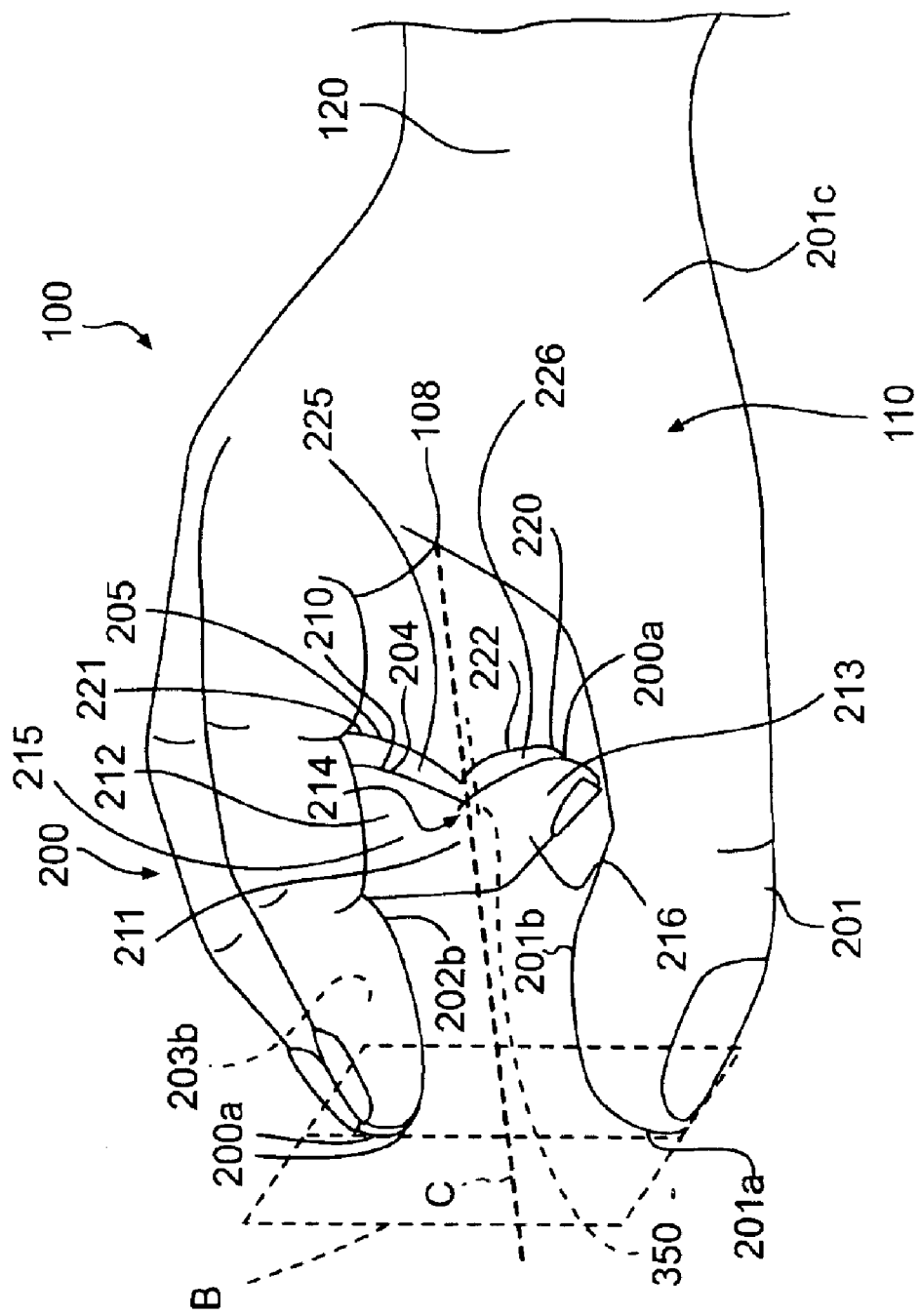

There can be variations to the T position. FIG. 2A and FIG. 2B show an adaptation of the T Position to the position of the hand 100 in the Forceps Hand Position (FHP). As shown in FIG. 2A and FIG. 2B, when the hand 100 is in the Forceps Hand Position (FHP), the thumb 201, index finger 202 and middle finger 203 are partially extended from the T Position. However, the ring finger 204 and small finger 205 remain in the T Position. In the Forceps Hand Position (FHP) the tip 201a of the thumb 201 opposes the space 320 between the tip 200a of the index finger 202 and the tip 200a of the middle finger 203 as it does in the T Position. Also note the tip 200a of the ring finger 204 and the tip 200a of the small finger 205 end at the same line 340 relative to the T Position for the hand 100. FIG. 2B illustrates a view of the radial side 110 of the hand 100 with the hand 100 in the Forceps Hand Position (FHP). When the hand 100 is in the Forceps Hand Position (FHP), as shown by the dashed line 305, the tip 201a of the thumb 201 is in substantial alignment with the tip 200a of the index finger 202 and the tip 200a of the middle finger 203.

Continuing with reference to FIG. 2A, the horizontal crease 108 as shown in FIG. 1, crosses the palm 102 of the hand 100 and is hidden by the base of the thumb 201 until the horizontal crease 108 reaches the radial side 110 of the hand 100. The location of the radial end of the horizontal crease 108 is seen on the radial side 110 of the hand 100 in FIG. 2B. FIG. 1 also shows the location of the horizontal crease 108 on the ulnar side 111 of the hand 100.

Referring to FIGS. 2A and 2B, Plane C, as seen in FIG. 2B, illustrates the relationship of the hand to the center line of a handle of the present invention. Plane C passes through the radial side 110 of the hand 100 to the ulnar side 111 of the hand 100 when the hand 100 is in the Forceps Hand Position (FHP). On the radial side 110 of the hand 100 Plane C extends through the horizontal crease 108 to bisect the space made between the thumb 201 and the index finger 202 and middle finger 203. On the ulnar side 111 of the hand 100 Plane C passes through an area M about half way between the horizontal crease 108 and the pisiform bone 126 of the wrist 120. Plane C then continues to pass through the DIP joints 252 of the ring finger 204 and small finger 205 when the ring finger 204 and small finger 205 are in the T Position.

Figure 3A:
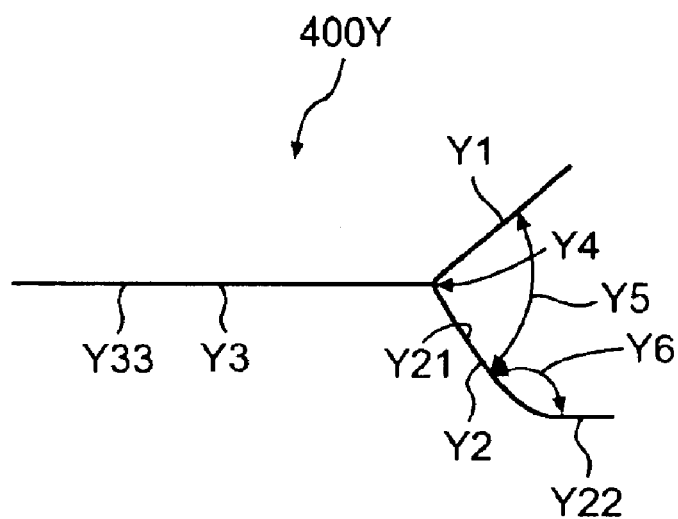
FIG. 3A and FIG. 3B are schematic views illustrating embodiments of handles of the present invention of a generally "Y"-shaped configuration.
Figure 3B:
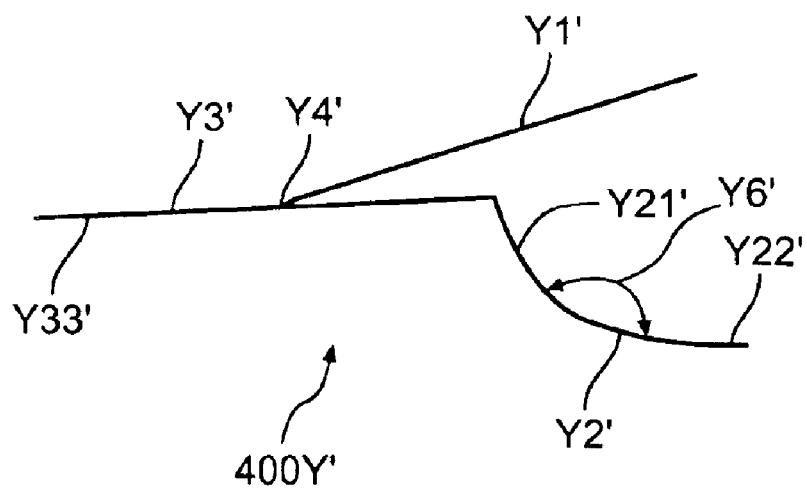

For illustrative purposes, with reference to FIG. 3A and FIG. 3B, schematic representations of handles of the present invention, are illustrated as schematic 400Y and schematic 400Y'. As illustrated in FIGS. 3A and 3B by the schematics 400Y and 400Y', handles of the present invention, such as for use as a forceps/tweezers, are generally of a "Y"-shaped configuration or desirably of a generally asymmetrical "Y"-shaped or "slingshot"-shaped configuration. A handle of the present invention, such as illustrated by the schematics 400Y and 400Y' can be considered to have two (upper) arms and one (lower) leg. In this regard, handles of the present invention can have two arms Y1, Y1' and Y2, Y2' that can be considered the proximal part of the schematics 400Y and 400Y' corresponding to a handle of the present invention. The two arms represented by Y1, Y1' and Y2, Y2' extend to the palm 102 of the hand 100. The leg Y3, Y3' corresponds to a distal leg of a handle of the present invention.

One arm Y1, Y1' of the schematics 400Y and 400Y' corresponds to the arm of a handle that contacts the radial side 110 of the palm 102 of the hand 100 and can be called the radial arm Y1, Y1' of the schematic 400Y, 400Y'. The second arm Y2, Y2' of the schematic 400Y, 400Y' corresponds to the arm of a handle that contacts the ulnar side 111 of the palm 102 of the hand 100 and can be called the ulnar arm Y2, Y2' of the schematic 400Y, 400Y'. The leg Y3, Y3' of the schematics 400Y and 400 Y' corresponds to the distal leg of a handle that extends to meet the thumb 201, index finger 202 and middle finger 203 when the hand 100 is in the Forceps Hand Position (FHP).

In the schematic 400Y of a handle of the present invention, the radial arm Y1, the ulnar arm Y2 and distal leg Y3 can meet at a common point Y4. Alternately, as illustrated in the schematic 400Y' of a handle of the present invention, the radial arm Y1' can meet the distal leg Y3' at another point Y4' along the distal leg Y3'. However, it is generally preferable to have the radial arm Y1, ulnar arm Y2 and distal leg Y3 meet at a common point Y4, as illustrated in the schematic 400Y.

The ulnar arm Y2, Y2' of the schematics 400Y and 400Y' has two sections, which are called the finger section Y21, Y21' of the ulnar arm Y2, Y2' and the palmar section Y22, Y22' of the ulnar arm Y2, Y2'. The finger section Y21, Y21' of the ulnar arm Y2, Y2' starts where the radial side 110 of the DIP joint 252 of the ring finger 204 meets the palmar side 221 of the DIP joint 252 of the ring finger 204 when the hand 100 is in the Forceps Hand Position (FHP).

The finger section Y21, Y21' of the ulnar arm Y2, Y2' ends at the ulnar side 111 of the DIP joint 252 of the small finger 205 when the hand 100 is in the Forceps Hand Position (FHP). The finger section Y21, Y21' of the ulnar arm Y2, Y2' follows the line 350 made by connecting the volar (inside) surfaces of the ring finger 204 and the small finger 205 at their respective DIP joints 252. However, the palmar section Y22, Y22' of the ulnar arm Y2, Y2' ends at area M on the hypothenar muscle area 116 between the horizontal crease 108 on the ulnar side 111 of the hand 100 and the pisiform bone 126 of the wrist 120. The palmar section Y22, Y22' of the ulnar arm Y2, Y2' ends at the ulnar side 111 of the DIP joint 252 of the small finger 205 when the hand 100 is in the Forceps Hand Position (FHP). The finger section Y21 in the schematic 400Y of the ulnar arm Y2 and the palmar section Y22 of the ulnar arm Y2 meet to form an angle Y6, such as an obtuse angle.

The distal leg Y3, Y3' of the schematics 400Y and 400Y' also originates at the DIP joint 252 where the palmar surface 210 of ring finger 204 meets the radial surface 211 of the DIP joint 252 of the ring finger 204 when the hand 100 is in the Forceps Hand Position (FHP). The distal leg Y3 ends at Plane B made by the tip 201a of the thumb 201, the tip 200a of the index finger 202 and the tip 200a of the middle finger 203 of the hand 100.

The junction 214 corresponds to the common point Y4. The junction 214 is defined at the meeting of the palmar surface 210 of the DIP joint 252 of ring finger 204 with the radial surface 211 of the DIP joint 252 of the ring finger 204 when the hand 100 is in the Forceps Hand Position (FHP). Therefore, the junction 214 determines the location on the schematic 400Y where the radial arm Y1, the ulnar arm Y2 and distal leg Y3 meet.

The radial arm Y1, Y1' can be straight or curved. The ulnar arm Y2, Y2' angles or curves to conform to the angle Y6, Y6', such as an obtuse angle. In the schematic 400Y the angle Y5, such as an obtuse angle, is formed where the radial arm Y1 and the ulnar arm Y2 meet as illustrated. The distal leg Y3, Y3' can be straight or curved and has a distal end Y33, Y33'. The length of the radial arm Y1, Y1' will vary with hand size. The length of the ulnar arm Y2, Y2' will likewise vary with hand size. The length of the distal leg Y3, Y3' will also vary with hand size.

Figure 4A:
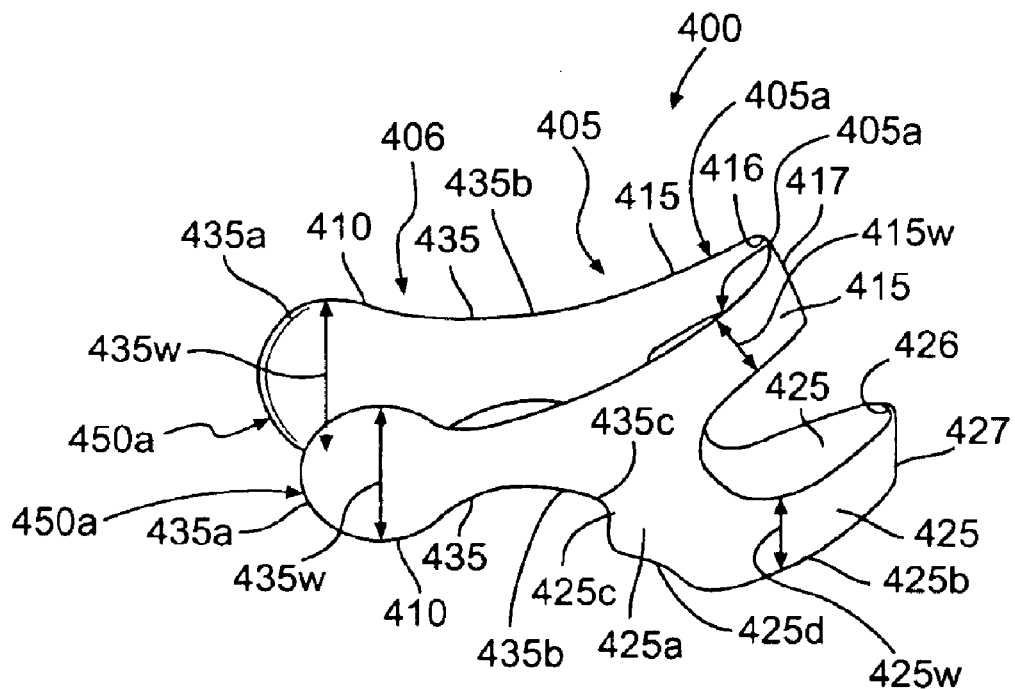
FIG. 4A, FIG. 4B and FIG. 4C are views illustrating a forceps/tweezers handle of the present invention.
Figure 4B:
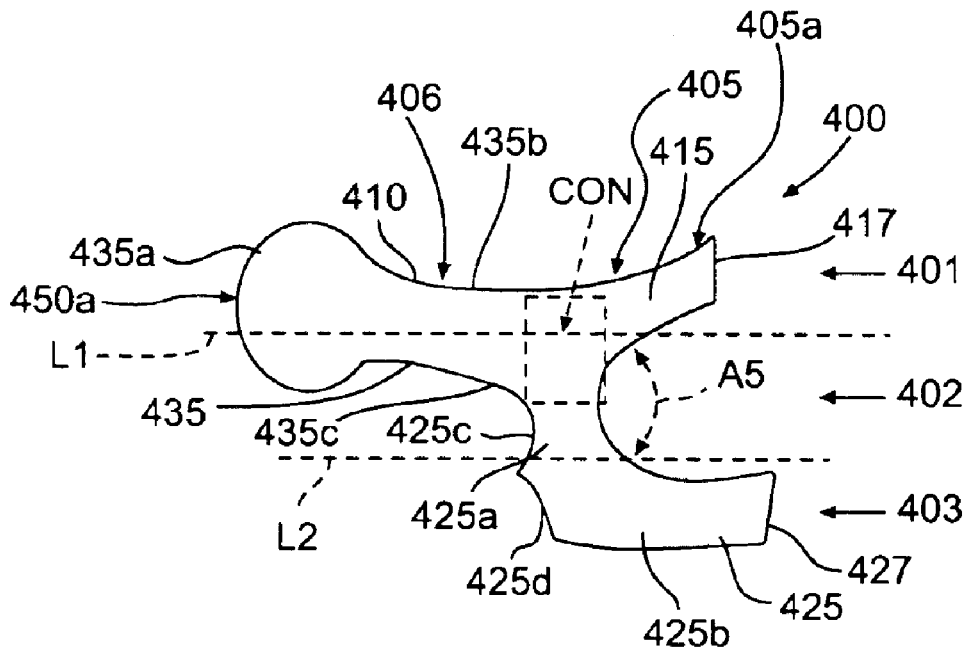
Figure 4C:
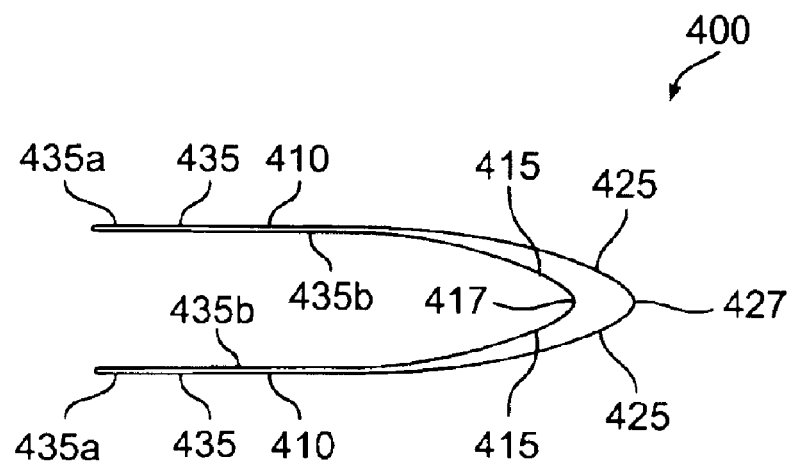

As illustrated in FIG. 4A, FIG. 4B and FIG. 4C, the embodiment of the forceps/tweezers handle 400 of the present invention is shaped in the form of a generally asymmetrical Y or slingshot shape. The forceps/tweezers handle 400 of the present invention has two opposing blades 410. Each opposing blade 410 of the forceps/tweezers handle 400 of the present invention can be a mirror image of the other. Each opposing blade 410 of the forceps/tweezers handle 400 of the present invention has a central connection area CON from which extend a radial arm 415k an ulnar arm 425 and a distal leg 435. The proximal part 405 of the forceps/tweezers handle 400 of the present invention is supported by the hand 100. The distal part 406 of the forceps/tweezers handle 400 of the present invention performs the work of grasping, pinching and other mechanical actions including cutting.

The proximal part 405a of each opposing blade 410 has a radial arm 415 and an ulnar arm 425. The radial arm 415 and ulnar arm 425 of each opposing blade 410 meet the connection area CON. The ulnar arm 425 of each opposing blade 410 of the forceps/tweezers handle 400 of the present invention has a finger section 425a and a palmar section 425b. The finger section 425a and the palmar section 425b meet at angle Y5 as discussed above in the section related to the ulnar arm Y2 of the schematic 400Y of FIG. 3A.

The palmar end 417 of the radial arm 415 of each opposing blade 410 meets to form a radial hinge 416. The palmar end 427 of the ulnar arm 425 of each opposing blade 410 meets to form an ulnar hinge 426. The hinges 416 and 426 can be made so one blade 410 continues or is formed integrally into the other blade 410. The hinges 416 and 426 can also be made of a mechanical connection means, such as a hinge arrangement. The radial hinge 416 and the ulnar hinge 426 allow the opposing blades 410 to move toward and away from each other.

The distal leg 435 of each opposing blade 410 extends from the connection area CON. The proximal section 435b of the distal leg 435 of each opposing blade 410 is attached to the connecting area CON. The distal end 435a of the distal legs 435 of each opposing blade 410 extends from the forceps/tweezers handle 400. The distal end 435a of each distal leg 435 can be an integrated working end 450a, tip or have multiple varied attachments for performing various suitable tasks or functions, such as grasping, pinching or cutting.

The width 415w of the radial arm 415 approximates the width of base of the index finger 202. The width 425w of the ulnar arm 425 approximates the width of base of the small finger 205. The width 435w of the distal end 435a of the distal leg 435 approximates the combined width of the distal pad 202b of the index finger 202 and the distal pad 203b of the middle finger 203.

The palmar end 417 of the radial arm 415 can be consistent with the corresponding surface of the palm 102 of the radial side 110 of the hand 100. The palmar end 427 of the ulnar arm 425 can be consistent with the corresponding surface of the palm 102 of the ulnar side 111 of the hand 100. Alternately the palmar end 417 of the radial arm 416 and the palmar end 427 of the ulnar arm 425 can be parallel to each other.

Also, as illustrated in FIG. 4B, the forceps/tweezers handle 400 of the present invention can have three sections. There is the radial section 401, the middle section 402 and the ulnar section 403. The radial section 401 of the forceps/tweezers handle 400 of the present invention is related to the radial side 110 of the hand 100 and can make contact with the thumb 201, the index finger 202 and the thenar area 114 of the palm 102 of the hand 100. The middle section 402 includes the area of the forceps/tweezers handle 400 of the present invention that can make contact with the middle finger 203 and ring finger 204 and without contacting the region over the CT 124. The ulnar section 403 includes the area of the forceps/tweezers handle 400 of the present invention that can make contact with the small finger 205 and the hypothenar muscle area 116 on the palm 102 on the ulnar side 111 of the hand 100. The forceps/tweezers handle 400 of the present invention can be used with right hand 100 or left hand 100.

Figure 5A:
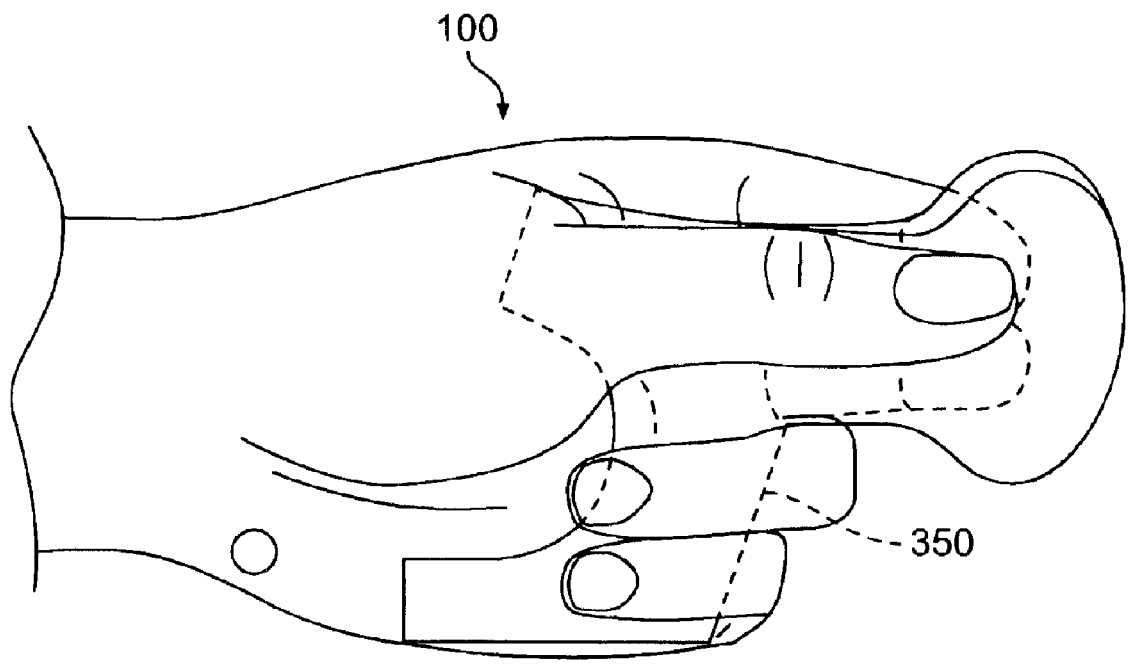
FIG. 5A and FIG. 5B are views illustrating a hand in the Forceps Hand Position (FHP) with the hand holding a forceps/tweezers handle of the present invention.
Figure 5B:
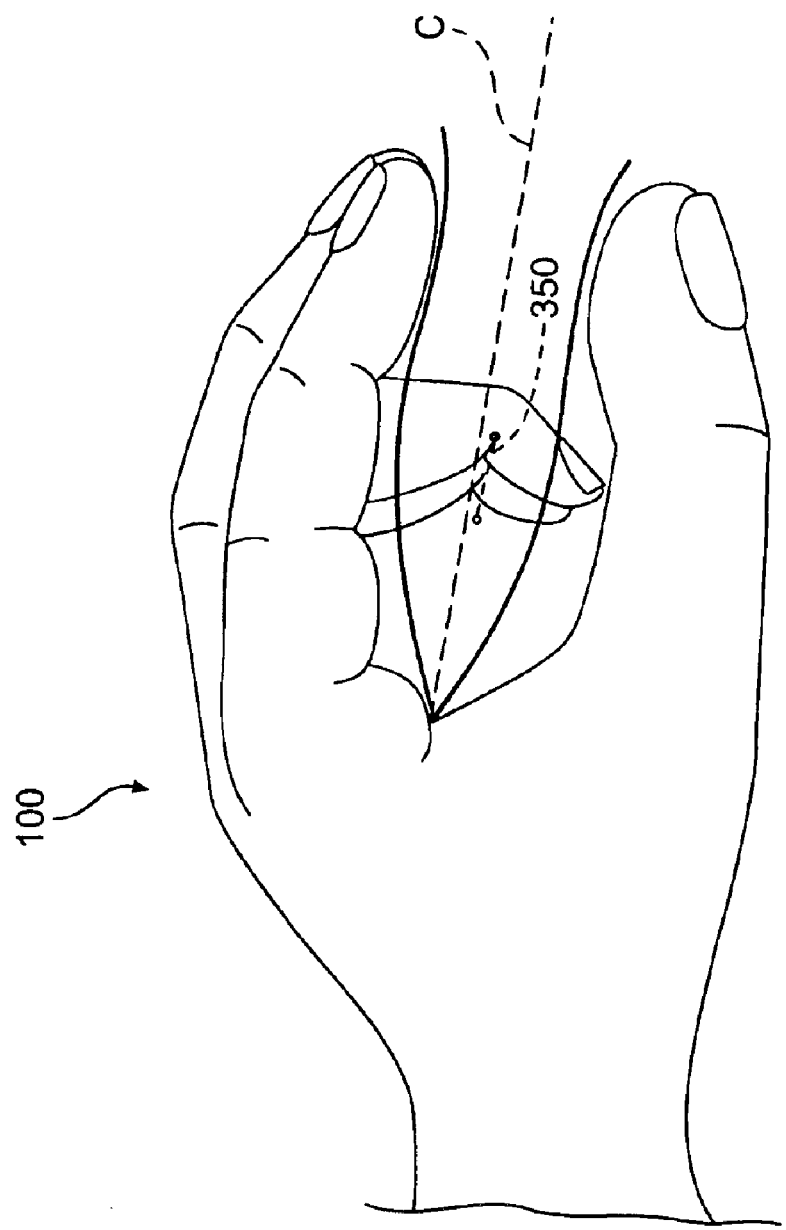

FIG. 5A and FIG. 5B illustrate a hand in the Forceps Hand Position (FHP) with the hand holding a forceps/tweezers handle of the present invention. FIG. 5A is a palmar view of the hand holding a forceps/tweezers handle and FIG. 5B is a radial view the hand holding a forceps/tweezers handle. With reference to FIG. 5A the horizontal crease 108 on the radial side 110 of the hand 100 contacts the radial hinge 416 at the palmar end 417 of the radial arm 415 of each opposing blade 410 of the forceps/tweezers handle 400 of the present invention. Area M on the palm 102 between the horizontal crease 108 on the ulnar side 111 of the hand 100 and the pisiform bone 126 of the wrist 120 contacts the ulnar hinge 426 of the palmar end 427 of the ulnar arm 425 of each opposing blade 410 of the forceps/tweezers handle 400 of the present invention.

Continuing with reference to FIGS. 1 through 5B, the palmar surface 210 of the middle phalange 215 of the ring finger 204 and the palmar surface 210 of the distal phalange 216 of the ring finger 204 contact the ring finger contact areas 425c of the finger section 425a of the ulnar arm 425 of the opposing blades 410 of a handle of the present invention, such as a forceps/tweezers handle 400 of the present invention. The palmar surface 220 of the middle phalange 225 of the small finger 205 and the palmar surface 220 of the distal phalange 226 of the small finger 205 contact the small finger contact areas 425d of the finger section 425a of the ulnar arm 425 of the opposing blades 410 of the forceps/tweezers handle 400 of the present invention. The radial side surface 211 of the middle phalange 215 of the ring finger 204 and the radial side surface 211 of the distal phalange 216 of the ring finger 204 contact the proximal section 435b of the distal leg 425 of the forceps/tweezers handle 400 of the present invention.

The distal pad 201b of the thumb 201 contacts the distal end 435a of the distal leg 435 of one opposing blade 410 of the forceps/tweezers handle 400 of the present invention and distal pad 202b of the index finger 202 and the distal pad 203b of the middle finger 203 contacts the mirror image blade 410 of the forceps/tweezers handle 400 of the present invention.

The hand 100 desirably supports a handle of the present invention, such as the forceps/tweezers handle 400 of the present invention, at five contact locations. The first support location is where the radial side 110 of the horizontal crease 108 of the hand 100 contacts the palmar end 417 of the radial arm 415 of each opposing blade 410 of the forceps/tweezers handle 400 of the present invention. The second support location can be where the ulnar side 111 of the horizontal crease 108 of the hand 100 contacts the palmar end 427 of the ulnar arm 425 of each opposing blade 410 of the forceps/tweezers handle 400 of the present invention. However, the optimal second support location is where the palmar end 425b of the ulnar arm 425 of each opposing blade 410 of the forceps/tweezers handle 400 of the present invention contacts area M. Area M is approximately located between the ulnar side 111 of the horizontal crease 108 and the pisiform bone 126 of the wrist 120 on the ulnar side 111 of the hand 100. The third support location is where the palmar surface 210 of the middle phalange 215 of the ring finger 204 and the palmar surface 210 of the distal phalange 216 of the ring finger contact area 425c contacts section 425a of each ulnar arm 425 of the opposing blades 410 of the forceps/tweezers handle 400 of the present invention.

The fourth support location is on the radial side surface 211 of the middle phalange 215 of the ring finger 204 and on the radial side surface 211 of the distal phalange 216 of the ring finger 204 which contacts the ring finger contact area 435c of the proximal section 435b of the distal leg 435 of the forceps/tweezers handle 400 of the present invention. The fifth support location is on the palmar surface 220 of the middle phalange 225 of the small finger 205 and on the palmar surface 220 of the distal phalange 226 of the small finger 205 which contacts the small finger contact area 425d of the finger section 425a of each ulnar arm 425 of the opposing blades 410 of the forceps/tweezers handle 400 of the present invention.

Support and stabilization within the hand 100 for a handle of the present invention, such as the forceps/tweezers handle 400 of the present invention, is enhanced by deep flexor forearm muscle contraction on the distal phalange 216 of the ring finger 204 and the superficial flexor forearm muscle contraction on the middle phalange 215 of the ring finger 204 and by deep flexor forearm muscle contraction on the distal phalange 226 of the small finger 205 and the superficial flexor forearm muscle contraction on the middle phalange 225 of the small finger 205 on the finger section 425a of the ulnar arms 425 of the opposing blades 410. Such contraction pulls the forceps/tweezers handle 400 of the present invention against the horizontal crease 108 of the palm 102 at the radial side 110 of the hand 100 and against a location within area M of the palm 102 at the ulnar side 111 of the hand 100. Support for lifting objects held by a handle of the present invention, such as the forceps/tweezers handle 400 of the present invention, by the hand 100 is enhanced by contact at the radial surface 211 of the ring finger 204 with the ring finger contact area 435c of the proximal section 435b of the distal leg 435 of the forceps/tweezers handle 400 of the present invention.

The distal ends 435a of the distal legs 435 of the opposing blades 410 are moved to pinch the forceps/tweezers handle 400 of the present invention. Pinch is the function of forceps or tweezers. Closing the distal pad 201b of the thumb 201 and the distal pad 202b of index finger 202 can contribute to support when using the common forceps or tweezers. However, the thumb 201, index finger 202 and middle finger 203 are not necessarily needed for support of the forceps/tweezers handle 400 of the present invention. The thumb 201, index finger 202 and middle finger 203 are only involved with pinch. When using a forceps/tweezers handle 400 of the present invention, the thumb 201, index finger 202 and middle finger 203 are not generally used to support the forceps/tweezers handle 400 of the present invention. Therefore, using the forceps/tweezers handle 400 of the present invention can reduce strain on the muscles flexing the thumb 201, index finger 202 and middle finger 203 for fine or gross pinch.

Hand Measurements

One of the goals in developing the proposed forceps/tweezers handle 400 of the present invention is to have it fit the hand. As recognized in the shoe industry feet have a range of lengths and widths. The same is true of hands. The length from wrist 120 to the tips 200a of the long fingers 200 and width from the radial side 110 of the hand 100 to the ulnar side 111 of the hand 100 vary such that hands can be short and long, short and narrow, long and wide and long and narrow. In general, male hands are longer and wider than female hands.

It is possible to develop one size for a handle of the present invention, such as the forceps/tweezers handle 400 of the present invention, to span many hands. However, holding a forceps/tweezers handle 400 of the present invention will require less muscular effort, be more comfortable and have greater stability if it is made in various sizes for the hand 100 in the Forceps Hand Position (FHP). The sizes for a handle of the present invention, such as the forceps/tweezers handle 400 of the present invention, will depend on measurements taken with the hand in the Forceps Hand Position (FHP) as shown in FIG. 2A and FIG. 2B.

Figure 6A:
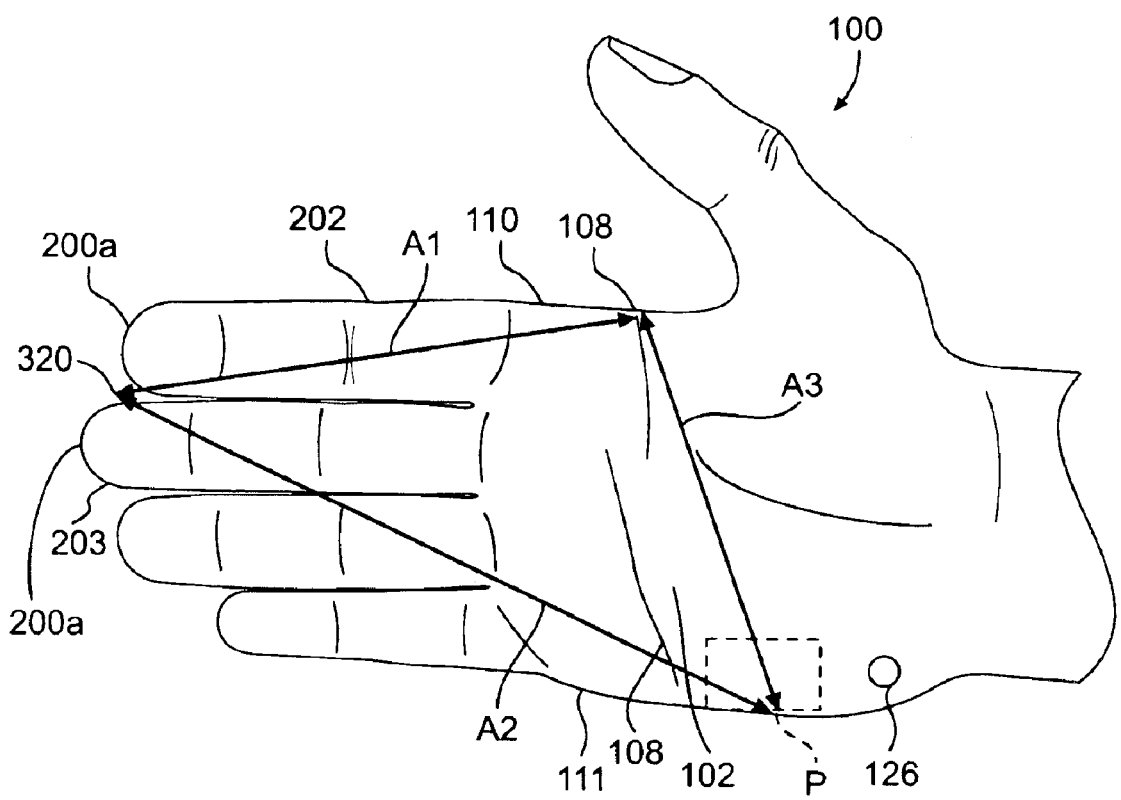
FIG. 6A and FIG. 6B illustrate lines for measurement to determine the dimensions of a forceps/tweezers handle of the present invention.
Figure 6B:
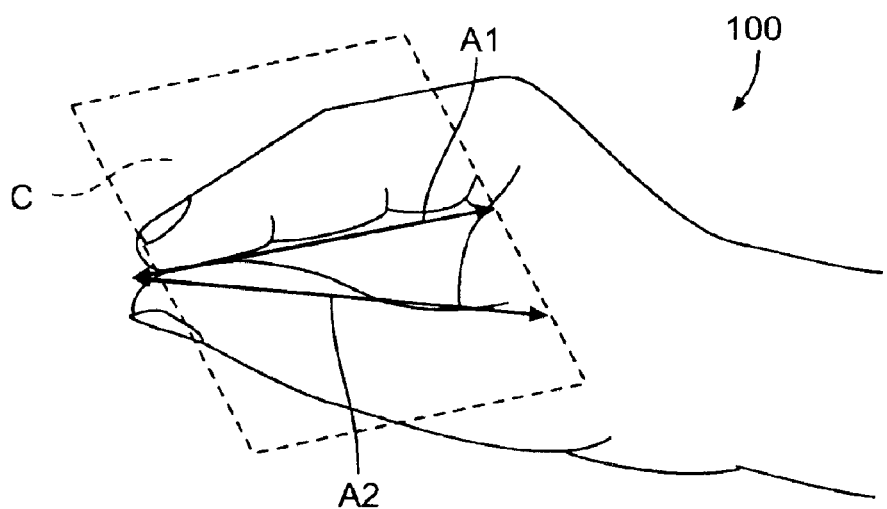

With reference to FIG. 6A and FIG. 6B, Line A1, Line A2 and Line A3 are used to determine the range of sizes of a handle of the present invention, such as the forceps/tweezers handle 400 of the present invention, for the human hand. Line A1 is the distance from the space 320 between the tip 200a of the index finger 202 and the tip 200a of the middle finger 203 extending to the radial side 110 of the horizontal crease 108 of the palm 102 of the hand 100. Line A2 is the distance from the space 320 between the tip 200a of the index finger 202 and the tip 200a of the middle finger 203 extending to Point P, which is in Area M at approximately one half the distance between the horizontal crease 108 and the pisiform bone 126 on the ulnar side 111 of the palm 102 of the hand 100.

The distances Line A1 and Line A2 are measured with the tip 201a of the thumb 201 opposing the tip 200a of the index finger 202 and the tip 200a of the middle finger 203 as shown in FIG. 2A and FIG. 2B and the hand 100 as shown in FIG. 6B. Line A3 is the distance from the radial side 110 of the horizontal crease 108 of the palm 102 of the hand 100 to Point P in area M on the hypothenar muscle area 116 on the ulnar side 111 of the palm 102 of the hand 100.

Figure 7:
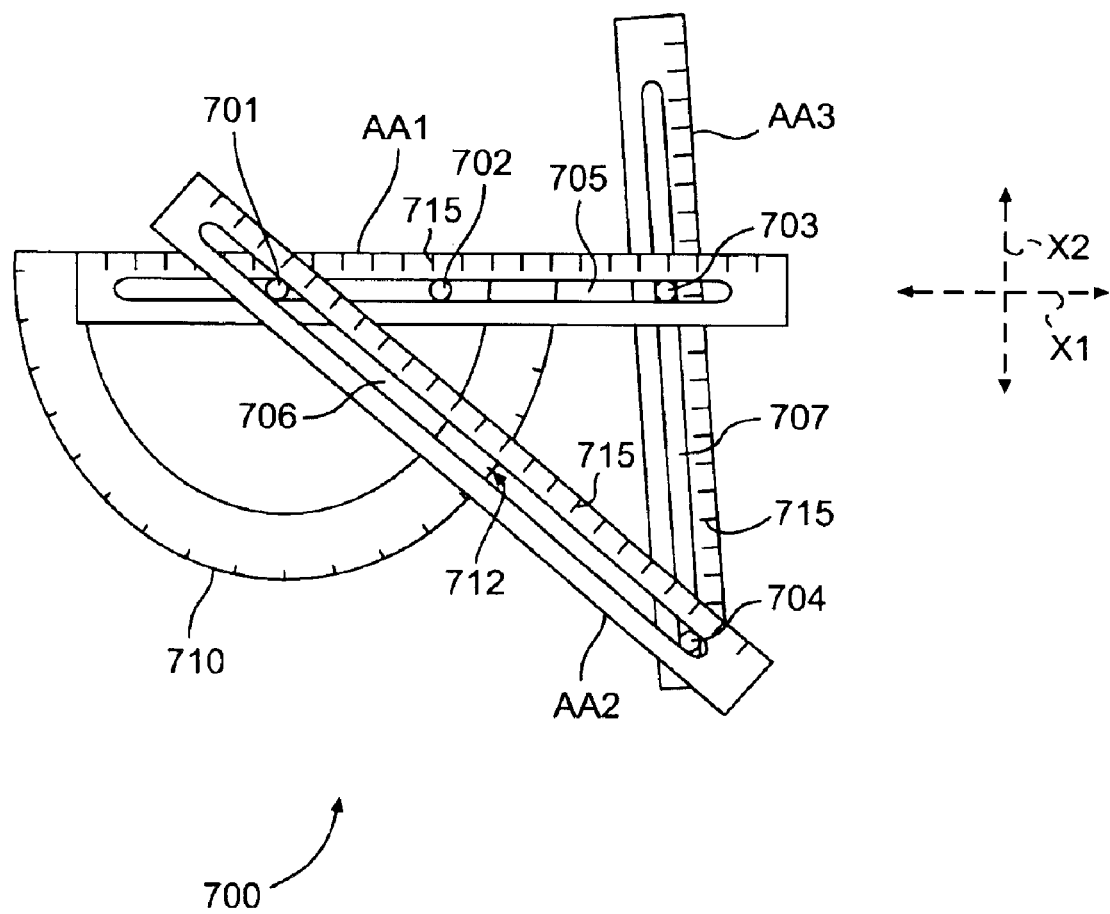
FIG. 7 illustrates a protractor measuring device used to measure the hand to determine angles and sizes for a handle of the present invention.

Individual measurements for a handle of the present invention, can be taken, with the protractor measuring device 700 illustrated in FIG. 7, for a right hand 100 or left hand 100 in the Forceps Hand Position (FHP). The protractor measuring device includes a protractor 710 and a triangular measuring member made from measuring members, such as rulers AA1, AA2 and AA3. Each ruler has a slot, with a slot 705 in ruler AA1, a slot 706 in ruler AA2 and a slot 707 in ruler AA3. Fastening members, such as rivets pass through the slots to connect the rulers so each ruler can slide along the other. Rivet 701 connects Ruler AA1 and Ruler AA2 to the center of protractor 710 where the zero degree axis X1 meets the ninety degree axis X2. Ruler AA1 is also connected to the protractor 710 along the zero degree axis X1 of the protractor 710 by rivet 702. Ruler AA1 and AA2 can move along rivet 701. Ruler AA3 is moveably connected to Ruler AA1 at rivet 703. Ruler AA3 is also moveably connected to Ruler AA2 at rivet 704.

The distances for line A1, line A2 and line A3 are desirably measured in centimeters along ruler AA1, ruler AA2 and ruler AA3. The measurements for line A1 start at the horizontal crease 108 on the radial side 110 of the hand 100 on ruler AA1. The measurements for line A2 start at Point P in Area M between the horizontal crease 108 on the ulnar side 111 of the hand 100 and the pisiform bone 126 on ruler AA2. The measurements for line A1 and line A2 end at rivet 701. Ruler AA3 slides along ruler AA1 and ruler AA2 to touch the palm 102 of the hand 100. The measurement for line A3 is read at the gradation marks 715 where ruler AA3 crosses ruler AA1 to the gradation marks 715 where ruler AA3 crosses the gradation marks 715 of ruler AA2. The angular degree reading area 712 on the protractor 710 is read in the slot 706 of ruler AA2 to determine the angle between Line Al and Line A2.

Measurements were made on the right hands of fifty males and forty females. The height of the males in this group ranged between 5'6" to 6'4". Female height ranged from 4'11" to 6'0". The measurement for line A1 in the male hand ranged from 7 to 9.5 cm. The measurement for line A1 in the female hand ranged from 7 to 8.5 cm. The measurement for line A2 in the male hand ranged from 9 to 11.5 cm. The measurement for line A2 in the female hand ranged from 9 to 11 cm. The measurement for line A3 in the male hand ranged from 6.5 to 8 cm. The measurement for line A3 in the female hand ranged from 6 to 7.5 cm. The angular degree reading from the angular degree reading area 712 for males averaged 45 degrees and the angular degree reading from the angular degree reading area 712 for females averaged 40 degrees. As expected, the male hand is longer and wider than the female hand. This data can be analyzed to develop groups of sizes for the proposed forceps/tweezers handle 400 of the present invention.

Alternate Measuring Device

Figure 8A:
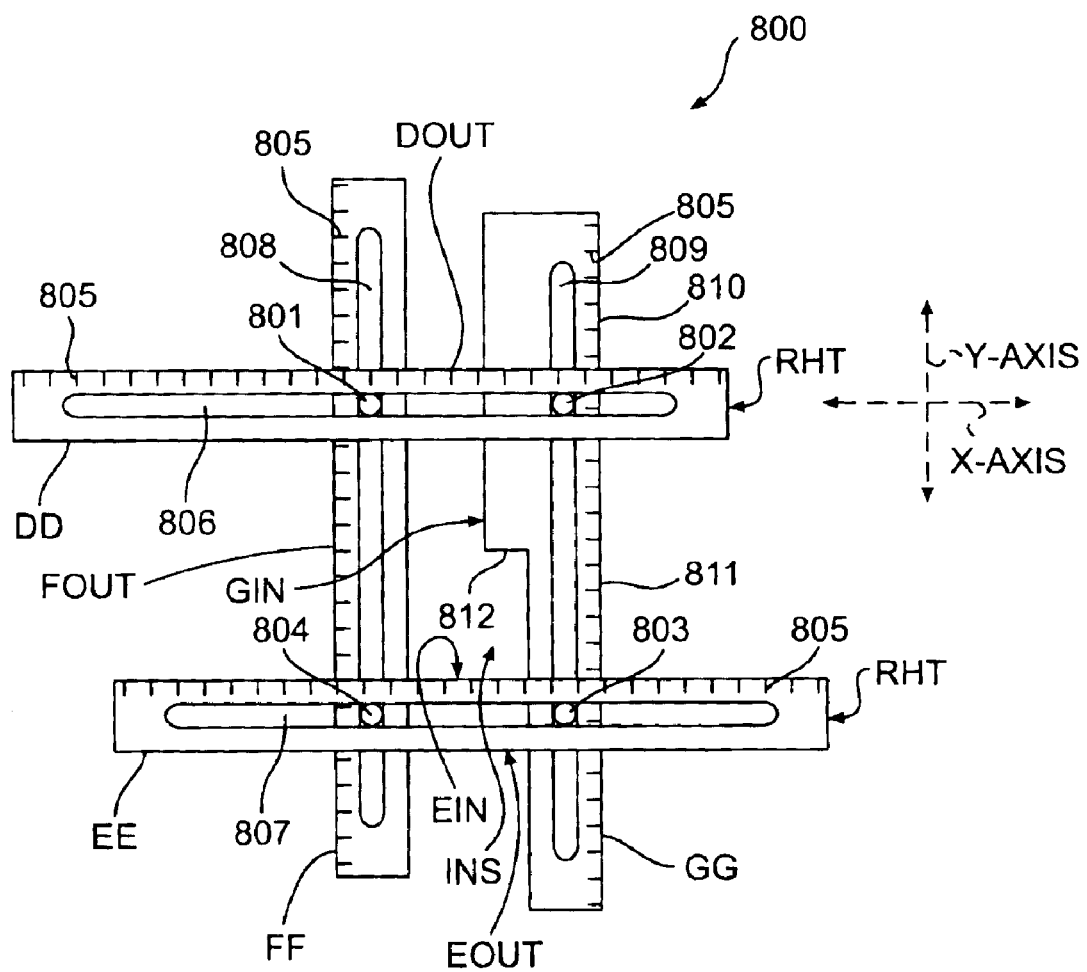
FIG. 8A and FIG. 8B illustrate a rectangular measuring device used as an alternate to the protractor measuring device of FIG. 7 to measure the hand for determining measurements and locations of lines related to the measurements for producing sizes for a handle of the present invention, with FIG. 8C and FIG. 8D illustrating the arrangement, measurements and locations of such lines used to produce a handle of the present invention.

A rectangular measuring device 800 for measuring the hand 100 such as can be used for determining sizes and shapes of handles of the present invention, such as the forceps/tweezers handle 400, is desirably made of measuring members such as four rulers, as illustrated in FIG. 8A, and can also be used when the hand 100 is in the Forceps Hand Position (FHP) to measure sizes for the forceps/tweezers handle 400 of the present invention. The rulers or measuring members are respectively indicated by the letters DD, EE, EF and GG, with ruler DD as a first measuring member, with ruler EE as a second measuring member, with ruler EF as a third measuring member and ruler GG as a fourth measuring member. Each ruler DD, EE, FF, GG is set at right angles to each other. Ruler DD and ruler EE are generally parallel and in the X-axis direction, as illustrated in FIG. 8A. Ruler FE and GG are generally parallel and in the Y-axis direction, as illustrated in FIG. 8A. Each ruler DD, EE, FE, GG has a corresponding slot 806, 807, 808, 809 along the center of its length and has corresponding gradation marks 805. The rulers DD, EE, FF, GG are connected by fastening members, such as rivets 801,802,803,804, or other desirable fasteners, such that the rulers DD, EE, FF, GG are loosely connected within the rectangular measuring device 800. The loose connection at rivets 801,802,803,804 allows each ruler DD, EE, FF, GG to slide along in the X-axis direction and/or the Y-axis direction. The dimensions, length and width, of Rulers DD, EE, and FF can generally be the same whereas ruler GG can generally have a wider portion, such as a five millimeter wide segment 810, starting at elevation 812 at approximately half the length of ruler GG. The other half of ruler GG is a standard ruler or other suitable measuring device and is identified as the narrow segment 811 of ruler GG. Measurements start at the right end of ruler DD and EE indicated by RHT in FIG. 8A. Measurements start near ruler DD for ruler FF. Measurements start near ruler EE for ruler GG. The wide segment of Ruler GG faces the inside INS of the rectangular arrangement or rectangular measuring device 800.

Figure 8B:
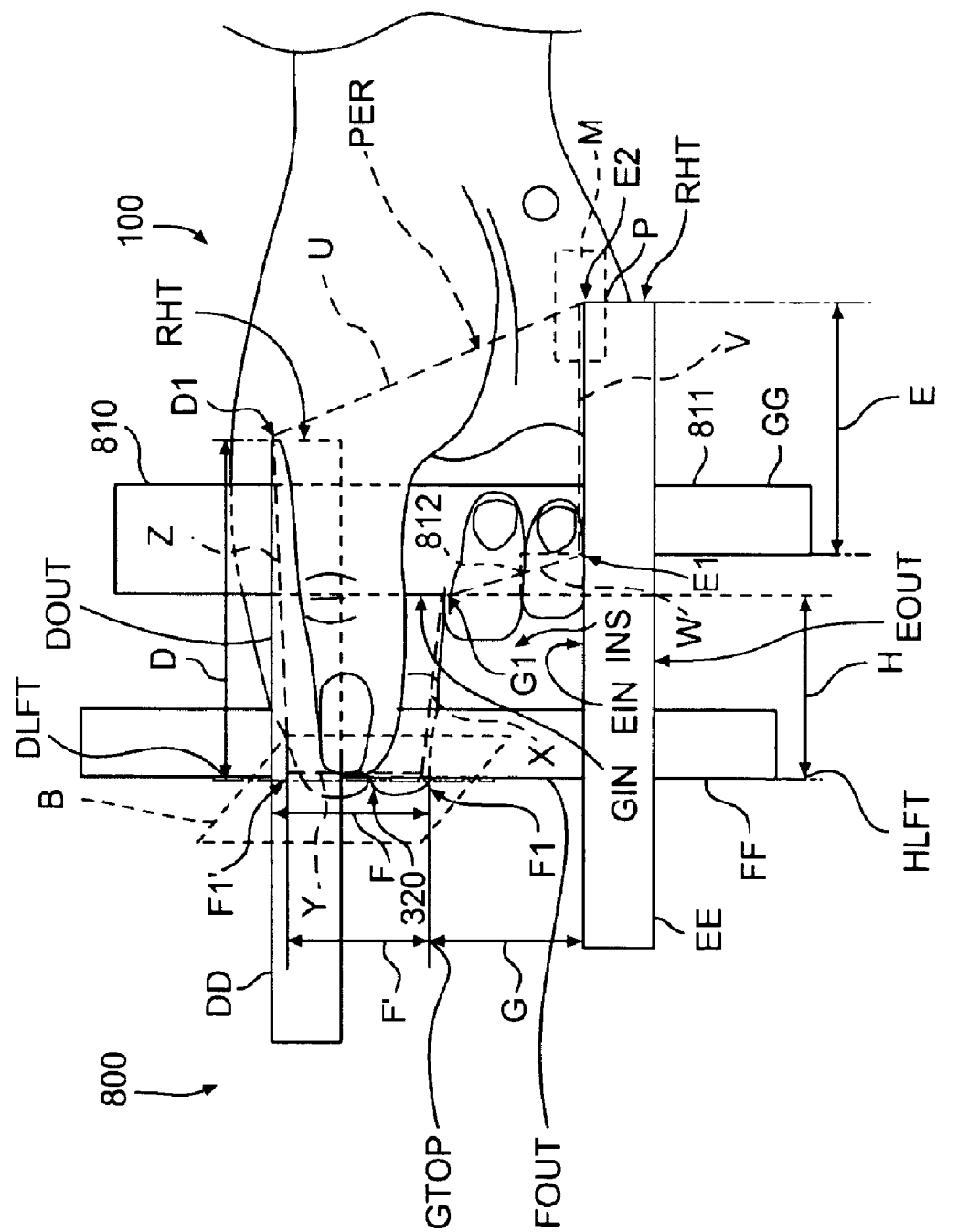

Referring to FIGS. 8A and 8B, the rectangular measuring device 800 is positioned along Plane C (see FIGS. 2B and 6B) to measure the right hand 100 in the Forceps Hand Position (FHP). The right end side RHT of ruler DD touches the horizontal crease 108 on the radial side 110 of the palm 102 of the hand 100. The right end side RHT of ruler EE is placed at Point P in Area M of the palm 102 on the ulnar side 111 of the hand 100. As illustrated in FIG. 8A and FIG. 8B, ruler FF moves in the X-axis direction along ruler DD and in the X-axis direction along ruler EE until the outside edge FOUT of ruler FF is at the Plane B (see FIGS. 2A and 8B) where the tip 201a of the thumb 201 opposes the space 320 between the tip 200a of the index finger 202 and the tip 200a of the middle finger 203. Ruler GG is moved in the X-axis direction along both ruler DD and ruler EE until the narrow segment 811 of ruler GG touches the palmar surface 220 at the DIP joint 252 of the small finger 205. Ruler GG is then moved in the Y-axis direction until the elevation 812 on ruler GG contacts the radial side 110 of the DIP joint 252 of the small finger 205. The wide segment 810 now touches the palmar surface 210 of the ring finger 204. This completes positioning of rulers DD, EE, FF and GG for measuring a hand size.

Continuing with reference to FIGS. 8A through 8D, measurements are taken along measurement distances D, E, F, F', G and H. Measurement distance D, as a first measurement distance, is measured on the outer side DOUT from the right end side RHT of ruler DD of the rectangular measuring device 800 from the horizontal crease 108 on the radial side 110 of the hand 100 to the outer side FOUT of ruler FF of the rectangular measuring device 800. Measurement distance E, as a second measurement distance, is measured along the inner side EIN of ruler EE on the rectangular measuring device 800 from the Point P in area M on the ulnar side 111 of the hand 100 to the palmar surface 220 of the small finger 205, when the small finger 205 is touching the narrow segment 811 of ruler GG and the hand 100 is in the Forceps Hand Position (FHP). Measurement distance F, as a third measurement distance, is measured along the outer side FOUT of ruler FF on the rectangular measuring device 800 from the outer side DOUT of ruler DD to the ulnar side 203c of the middle finger 203 when the hand 100 is in the Forceps Hand Position (FHP). Measurement distance F', as a fourth measurement distance, is measured along the outer side FOUT of ruler FF from the radial side 203a of the index finger 202 to the ulnar side 203c of the middle finger 203. Measurement distance G, as a fifth measurement distance, is measured along ruler GG on the inner side INS of the rectangular measuring device 800 from the inner side EIN of ruler EE to the radial side 110 of the ring finger 204 when the hand 100 is in the Forceps Hand Position (FHP). Measurement distance H, as a sixth measurement distance, is measured along ruler DD from the outer side FOUT of ruler FF to the wide segment 810 on the inner side GIN of ruler GG on the rectangular measuring device 800.

Continuing with reference to FIGS. 8A through 8D, measurement lines oriented and arranged to correspond to a hand in the Forceps Hand Position (FHP) are drawn from the corresponding first through sixth measurement distances D, E, F, F', G and H and are desirably recorded on a medium such as on grid paper. These measurement lines are used to produce corresponding outline lines for an outline for a handle shape, with the outline formed by these outline lines for a handle shave being illustrated in FIGS. 8C and 8D, and also being indicated in FIG. 8B, such as for the forceps/tweezers handle 400, of the present invention. First, a first measurement line corresponding to the second measurement distance E is drawn in the X-axis direction. Then, a second measurement line corresponding to the fifth measurement distance G is drawn in the Y-axis direction starting at a preselected distance, typically five millimeters (consistent with the elevation 812), to the left of the line drawn corresponding to the second measurement distance E. Next, a third measurement line corresponding to the sixth measurement distance H is drawn in the X-axis direction starting at the top GTOP of the second measurement line drawn for the fifth measurement distance G. Then a fourth measurement line corresponding to the third measurement distance F is drawn in the Y-axis direction. A fifth measurement line corresponding to the fourth measurement distance F' is then drawn on the same fourth measurement line as the third measurement distance F. Next, a sixth measurement line corresponding to the first measurement distance D is drawn in the X-axis direction. Furthermore, an end of the sixth measurement line for the first measurement distance D is on the same Y-axis direction line as the left end HLFT of the third measurement line for the sixth measurement distance H, and the fourth measurement line for the third measurement distance F is drawn in the Y-axis direction with an end of the fourth measurement line starting at the left end DLFT of the sixth measurement line for the first measurement distance D.

Figure 8C:
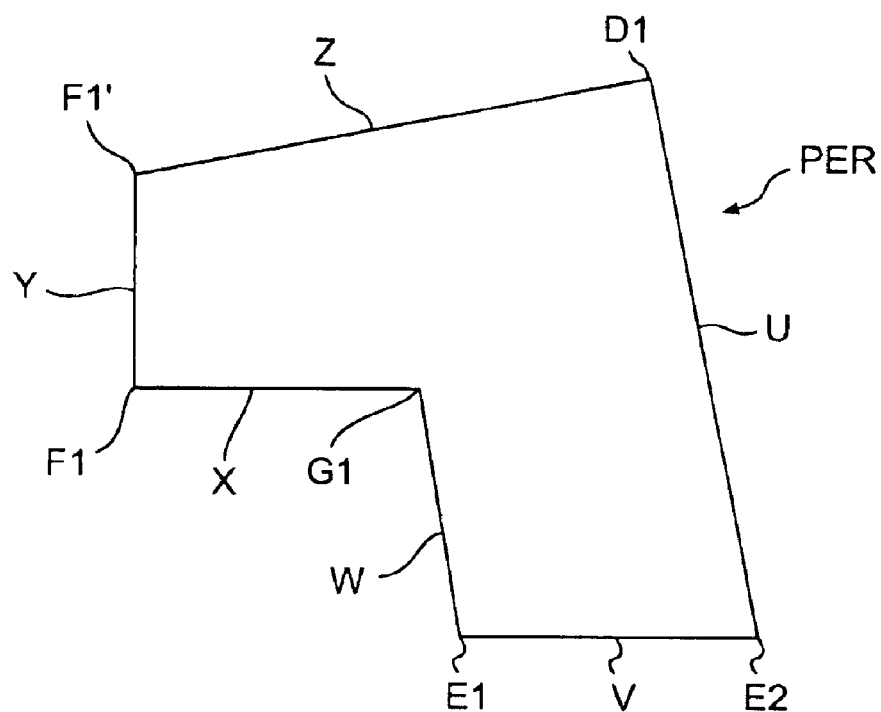
Figure 8D:
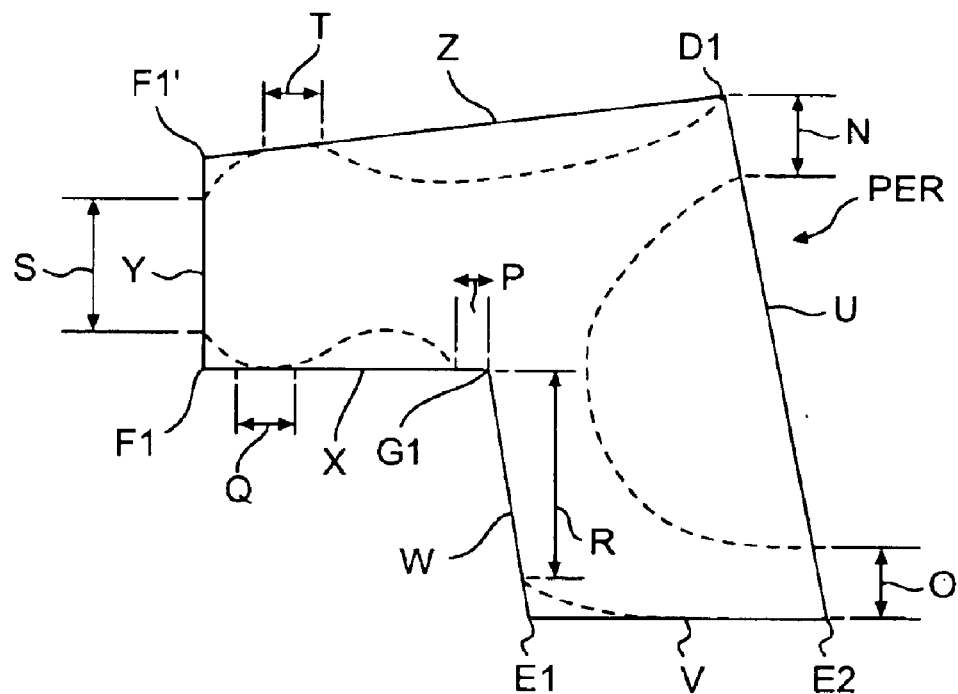

As discussed above, a handle, such as the forceps/tweezers handle 400, of the present invention can come in a plurality of sizes. The sizes of forceps/tweezers handles 400 of the present invention can be compiled by drawing point to point outline lines Z, Y, X, W, V and U to connect end points D1, F1', F1, G1, E1 and E2 on the measurement lines corresponding to measurement distances D, E, F, F', G and H as illustrated in FIGS. 8B, 8C and 8D. As illustrated in FIGS. 8A through 8D, the first point to point outline line is line Z, which connects end point D1 on the sixth measurement line corresponding to the first measurement distance D to end point F1' on the fifth measurement line corresponding to the fourth measurement distance F'. The second point to point outline line is line Y connecting end point F1' on the fifth measurement line corresponding to the fourth measurement distance F' to end point F1 on the fourth measurement line corresponding to the third measurement distance F, with the end point F1 also corresponding to the same end point on the third measurement line corresponding to the sixth measurement distance H. Then the third point to point outline line X connects end point F1 on the fourth measurement line corresponding to the third measurement distance F, which also corresponds to the same end point on the third measurement line corresponding to the sixth measurement distance H, to end point G1 on the second measurement line corresponding to the fifth measurement distance G, which is followed by the fourth point to point outline line W connecting end point G1 on the second measurement line corresponding to the fifth measurement distance G to end point E1 on the first measurement line corresponding to the second measurement distance E. The fifth point to point outline line V next connects end point E1 on the first measurement line corresponding to the second measurement distance E to end point E2 on the first measurement line corresponding to the second measurement distance E. Finally, the sixth point to point outline line U is drawn from end point D1 on the sixth measurement line corresponding to the first measurement distance D to end point E2 on the first measurement line corresponding to the second measurement distance E to complete the perimeter PER incorporating the outline lines Z, Y, X, W and V for measurements for a handle, such as the forceps/tweezers handle 400 of the present invention. Perimeters PER for various hand sizes are compared to produce a range of sizes for handles of the present invention. As discussed above, the forceps/tweezers handle 400 of the present invention can therefore contact the hand 100 at the following locations: at the horizontal crease 108 of the palm 102 on the ulnar side 111 of the hand 100, at a location in area M of the palm 102 on the ulnar side 111 of the hand 100, the palmar surface 210 of the ring finger 204 with the palmar surface 220 of the small finger 205, at the radial side surface 211 of the ring finger 204, at the distal pad 201*b* of the thumb 201, at the distal pad 202*b* of the index finger 202 and at the distal pad 203*c* of the middle finger 203.

The sizes of the forceps/tweezers handle 400 of the present invention are determined by plotting or recording measurements of the perimeter PER. However, the shape of the forceps/tweezers handle 400 of the present invention is related to those areas on the perimeter PER which touch, the hand 100 at certain areas. Referring to FIGS. 8C and 8D, sections of various outline lines of the perimeter PER forming the contact areas for handle measurements are indicated by double-arrowed lines for corresponding contact areas with a hand 100. A first section N on the sixth outline line U is a first limited contact area on the perimeter PER for contacting an area of the hand related to the horizontal crease 108 of the palm 102 on the radial side 110 of the hand 100. A second section O on the sixth outline line U is a second limited contact area on the perimeter PER for contacting an area of the hand related to area M of the palm 102 on the ulnar side 111 of the hand 100. A third section R on the fourth outline line W is a third limited contact area on the perimeter PER for contacting an area of the hand related to the palmar surface 210 of the ring finger 204 and the palmar surface 220 of the small finger 205. A fourth section P on the third outline line X is a fourth limited contact area on the perimeter PER for contacting an area of the hand related to the radial side surface 211 of the ring finger 204. The combination of a fifth section Q on the third outline line X, a sixth section S on the second outline line Y and a seventh section T on the first outline line Z are respectively fifth, sixth and seventh limited contact areas on the perimeter PER for contacting areas of the hand related to the distal pad 202*b* of the index finger 202 and the distal pad 203*b* of the middle finger 203. The combination of the fifth section Q on the third outline line X, the sixth section S on the second outline line Y and the seventh section T on the first outline line Z is duplicated on the distal ends 435*a* of the opposing blades 410 of a handle, such as forceps/tweezers handle 400, of the present invention and can relate to an area for the distal pad 201*b* of the thumb 201.

Therefore, the segments or sections of the respective sixth through first outline lines U, V, W, X, Y and Z that are not on the first section N on the sixth outline line U, the second section O on the sixth outline line U, the fourth section P on the third outline line X, the fifth section Q on the third outline line X, the third section R on the fourth outline line W, the sixth section S on the second outline line Y and the seventh section T on the first outline line Z on the perimeter PER can have any curve or shape because those areas generally do not contact parts of the hand 100 on a handle, such as the forceps/tweezers handle 400 of the present invention.

Variations of the Handle

Figure 9A:
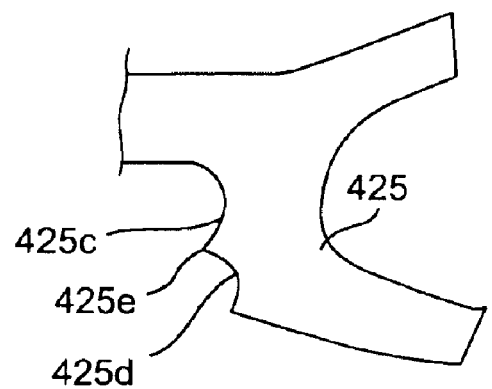
FIGS. 9A through 9G illustrate variations of a handle of the present invention.
Figure 9B:
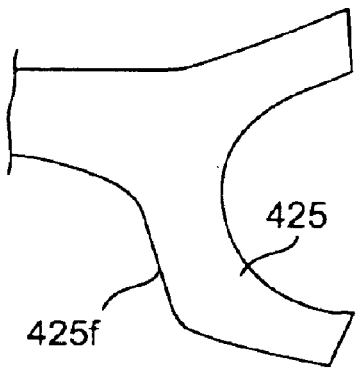

Referring now to FIGS. 9A and 9B, variations can be placed at the ring finger Contact area 425*c* and the small finger contact area 425*d* of the ulnar arm 425 of a handle, such as the forceps/tweezers handle 400, of the present invention, such as illustrated in FIG. 9A and FIG. 9B. A step 425*e* can be incorporated into the finger section 425*a* of the ulnar arm 425 between the ring finger contact area 425*c* and the small finger contact area 425*d* to conform with the palmar surface 210 of the ring finger 204 and the palmar surface 220 of the small finger 205 when the hand 100 is in the Forceps Hand Position (FHP). Furthermore, the ulnar arm 425 of a handle, such as the forceps/tweezers handle 400, of the present invention can have a straight portion 425*f* to meet the palmar surface 210 of the ring finger 204 and the palmar surface 220 of the small finger 205 when the hand 100 is in the Forceps Hand Position (FHP).

Figure 9C:
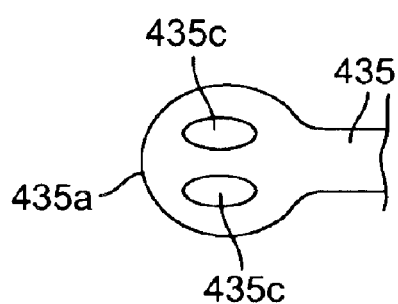
Figure 9D:
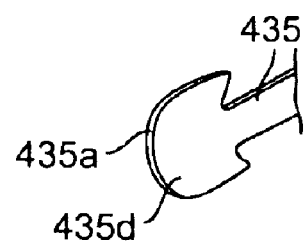

As illustrated in FIG. 9C and FIG. 9D, the distal end 435*a* of the distal legs 435 of the opposing blades 410 of a handle, such as the forceps/tweezers handle 400, of the present invention can have apertures 435*c*, concave portions 435*d*, be convex or have other means to reference the distal pad 201*b* of the thumb, the distal pad 202*b* of the index finger 202 and the distal pad 203*b* of the middle finger 203. The width of the distal end 435*a* of the distal legs 435 of the opposing blades 410 of a handle, such as the forceps/tweezers handle 400, of the present invention can be limited to allow contact with the central parts of the distal pad 202*b* of the index finger and of the distal pad 203*b* of the middle finger 203 of the hand 100.

Figure 9E:
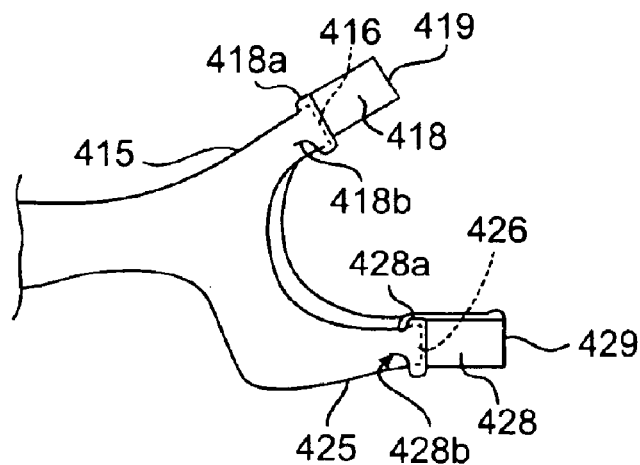
Figure 9F:
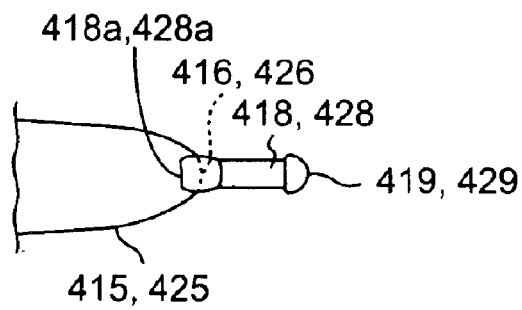

A handle, such as the forceps/tweezers handle 400, of the present invention can be made in one size or various sizes based on above described measurements with reference to FIGS. 7 through 8D. An alternative to making multiple sizes of the forceps/tweezers handle 400 of the present invention is to add extensions 418, 428 to adapt a handle, such as the forceps/tweezers handle 400, of the present invention to a range of hand sizes. As shown in FIG. 9E and FIG. 9F, for example, an extension 418 can be added to the radial hinge 416 of the radial arm 415 and an extension 428 can be added to the ulnar hinge 426 of the ulnar arm 425 of forceps/tweezers handle 400 of the present invention.

Figure 9G:
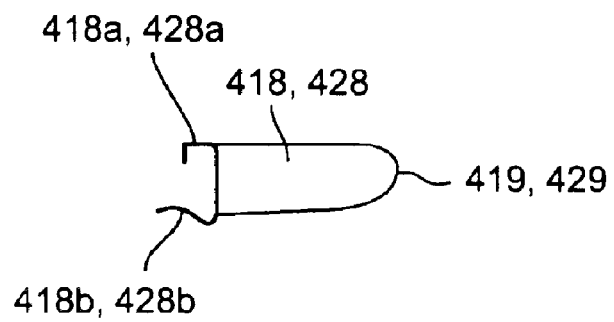

As illustrated in FIG. 9F, the extension 418,428 can have a collar 418*a*, 428*a* and a spring mechanism 418*b*, 428*b* to attach to the edges of the radial hinge 416 of the radial arm 415 and the ulnar hinge 426 of the ulnar arm 425 of the opposing blades 410 of the forceps/tweezers handle 400 of the present invention. Furthermore, as illustrated in FIG. 9G, the palmar end 419, 429 of the extension 418, 428 of the forceps/tweezers handle 400 of the present invention can have a generally round shape.

Figure 10A:
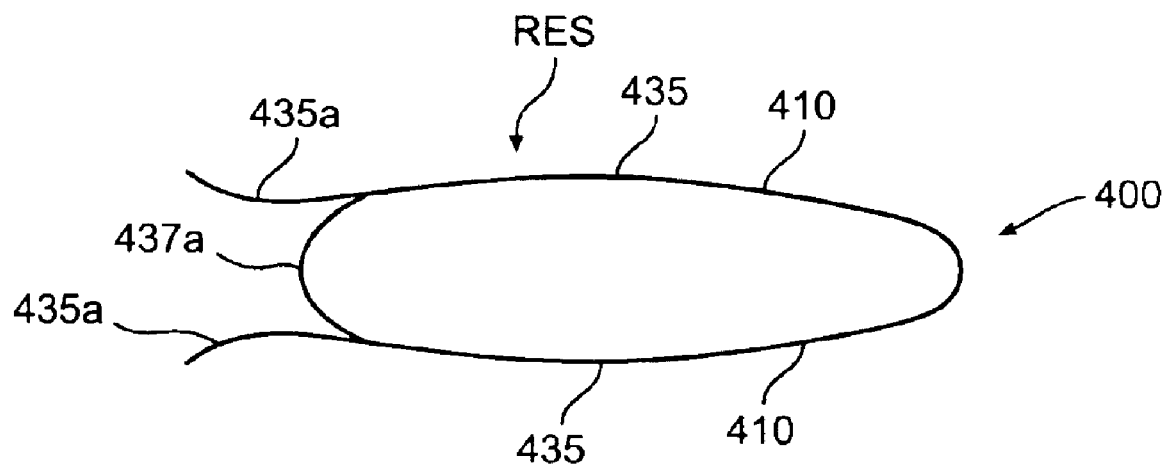
FIGS. 10A through 10G illustrate additions to a handle of the present invention near the distal end of a handle.
Figure 10B:
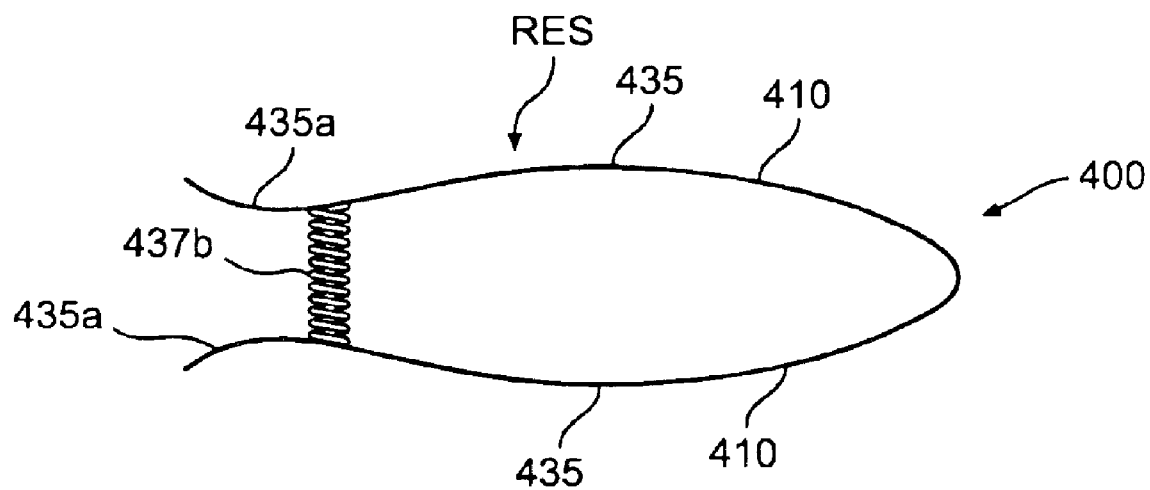

In some instances, when pinch is relaxed, it is desirable to maintain a resting distance corresponding to a distance when pinch is relaxed between the distal ends 435*a* of the distal legs 435 of the opposing blades 410 of a handle, such as the forceps/tweezers handle 400, of the present invention. FIG. 10A and FIG. 10B illustrate spring mechanisms 437*a*, 437*b* inserted between distal ends 435*a* of the distal legs 435 of the opposing blades 410 of the forceps/tweezers handle 400 of the present invention to maintain a resting position RES, illustrated in FIGS. 10A and 10B for the forceps/tweezers handle 400 of the present invention. Such a spring member 437*a* as shown in FIG. 10A can also maintain alignment of the distal ends 435*a* so the working ends 450 can meet and not be subject to excessive drift with respect to each other.

When using a handle, such as the forceps/tweezers handle 400, of the present invention it can be desirable to maintain closure or partial closure of the working ends 450 attached to the distal ends 435*a* of the distal legs 435 of the opposing blades 410 of a handle, such as the forceps/tweezers handle 400 of the present invention. FIG. 10G, FIG. 10D and FIG. 10E illustrate a clamping mechanism 438 inserted between distal ends 435*a* of the distal legs 435 of the opposing blades 410 of the forceps/tweezers handle 400 of the present invention to maintain such a closed or partially closed position for a handle, such as the forceps/tweezers handle 400, of the present invention.

Figure 10C:
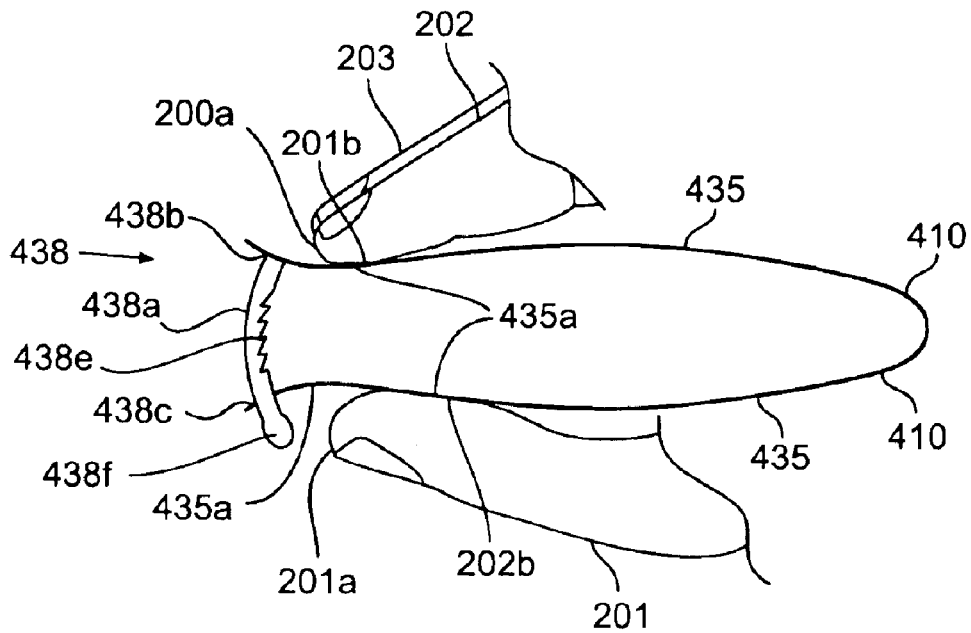
Figure 10D:
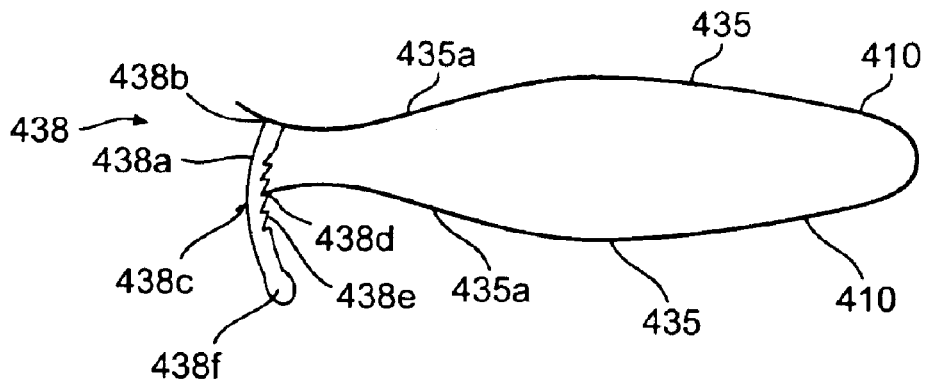
Figure 10E:
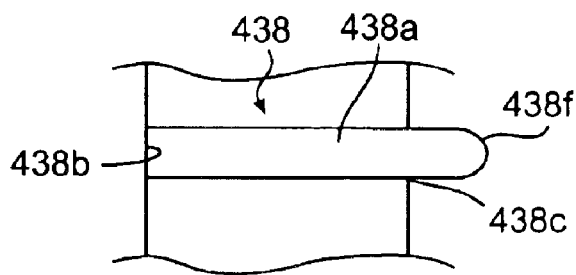

As illustrated in FIG. 10C, the clamping mechanism 438 includes a clamping post 438*a* attached via an attachment 438*b* to the distal end 435*a* of the distal leg 435 of a corresponding one of the opposing blades 410 of a handle, such as the forceps/tweezers handle 400, of the present invention. FIG. 10D illustrates a generally closed position of the forceps/tweezers handle, such as the forceps/tweezers handle 400, of the present invention with the clamping mechanism 438. FIG. 10E illustrates a front view of the clamping mechanism 438 with a handle, such as the forceps/tweezers handle 400, of the present invention in a generally open position.

The clamping post 438*a* extends through an aperture 438*c* on the other distal end 435*a* of the distal legs 435 of the opposing blades 410 of a handle, such as the forceps/tweezers handle 400, of the present invention. The clamping post 438*a* has a locking plate 438*d* that engages with the teeth 438*e* to maintain the working ends 450 of the distal ends 435*a* of the distal legs 435 of the opposing blades 410 of a handle, such as the forceps/tweezers handle 400, of the present invention in the closed position. The distal end 438*f* of the clamping post 438*a* can be pushed by the tip 201*a* of the thumb 201 or the tip 200*a* of the index finger 202, when a handle, such as the forceps/tweezers handle 400, of the present invention is used by a left hand 100, to release the clamping post 438*a* from the locking plate 438*d* and open the forceps/tweezers handle 400 of the present invention.

Figure 10F:
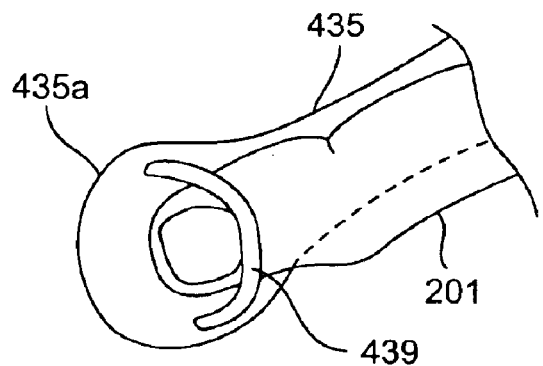
Figure 10G:
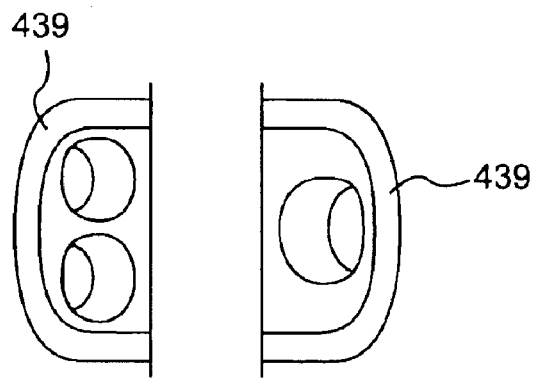

In another variation, as shown in FIGS. 10F and 10G, rings 439 for the thumb 201, index finger 202 and middle finger 203 can be attached to the distal ends 435*a* of the distal legs 435 of the opposing blades 410 of a handle, such as the forceps/tweezers handle 400, of the present invention to spread apart the working ends 450 of the forceps/tweezers handle 400 of the present invention.

Figure 11A:
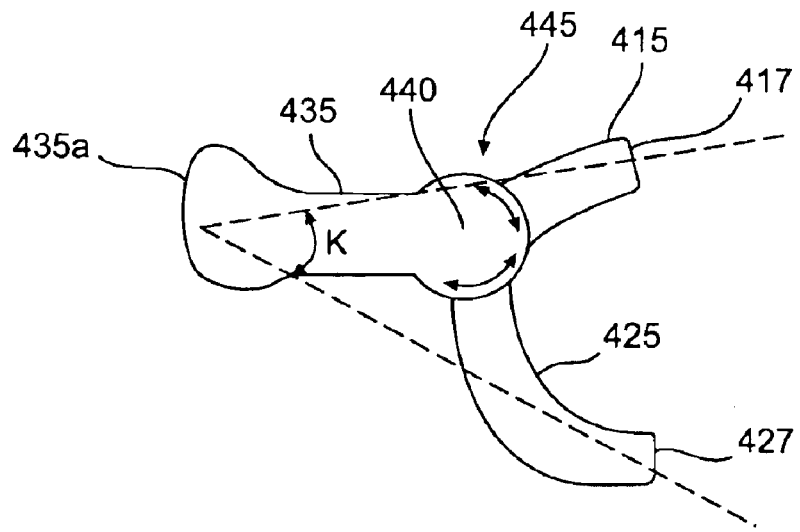
FIGS. 11A, 11B and 11C illustrate various views of a rotating mechanism located at a connecting area allowing rotation of the radial arm and ulnar arm in a handle of the present invention.
Figure 11B:
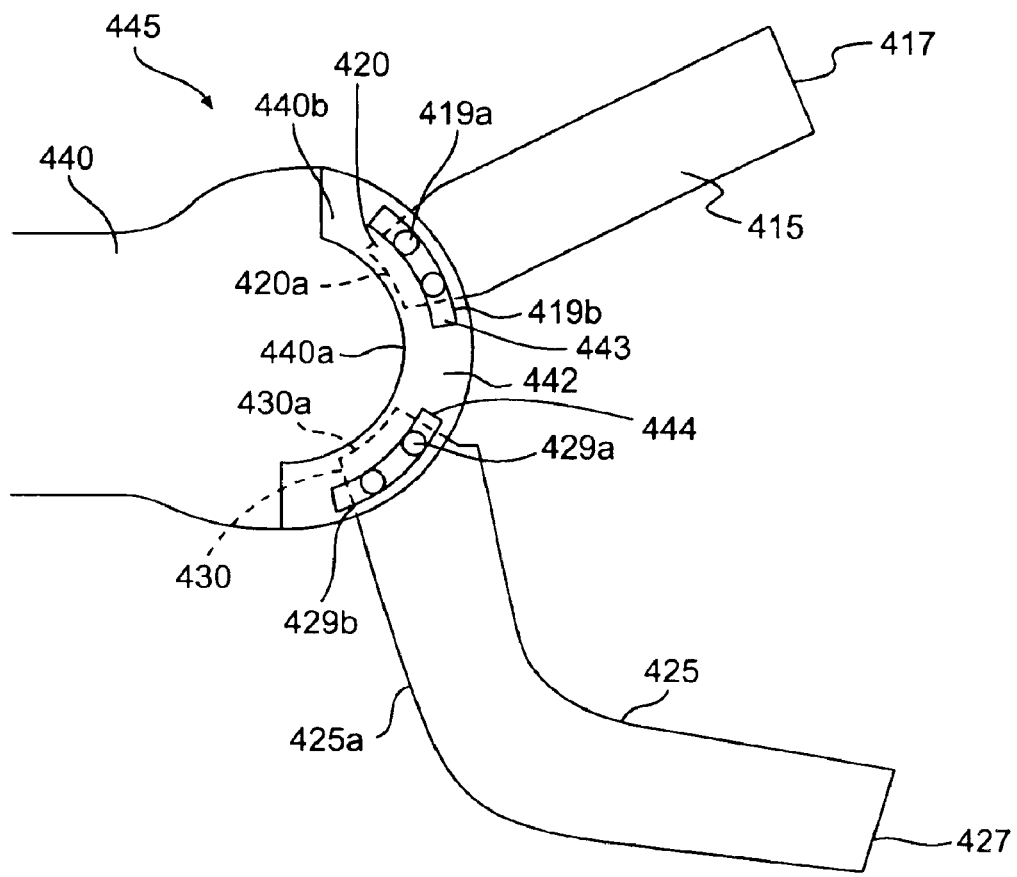
Figure 11C:
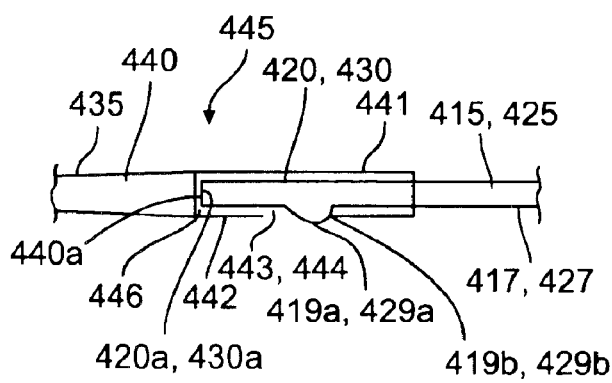

FIG. 11A, FIG. 11B and FIG. 11C illustrate another variation at the central connection area 440 (designated in FIG. 4 as CON) of a handle, such as the forceps/tweezers handle 400, of the present invention. The central connection area 440 can have a rotating mechanism 445 allowing angular movement of the attached radial arm 415 and ulnar arm 425 of a handle, such as the forceps/tweezers handle 400, of the present invention. Such rotational movement can adjust the position of the palmar end 417 of the radial arm 415 and the palmar end 427 of the ulnar arm 425 of a handle, such as the forceps/tweezers handle 400, of the present invention to a user's comfort when the handle contacts the horizontal crease 108 on the radial side 110 of the palm 102 of the hand 100 for multiple hand 100 sizes. Angle K illustrated in FIG. 11A corresponds to the angular degree reading 710 on the protractor measuring device 700 illustrated in FIG. 7. As discussed previously, the angular degree reading 710 corresponding to angle K determined for female hands was typically 40 degrees and the angular degree reading 710 determined for male hands was typically 45 degrees. Thus, the range of rotational movement of a rotating mechanism 445 at the central connection area 440 of a handle, such as the forceps/tweezers handle 400, of the present invention can be set to maintain the angle K, illustrated in FIG. 11A, typically between 35 to 50 degrees to account for overlap among handle sizes. Furthermore, each radial arm 415 and each ulnar arm 425 of a handle, such as the forceps/tweezers handle 400, of the present invention can be made in different sizes or have extensions 419,429 such as illustrated in FIG. 9E, FIG. 9F and FIG. 9G.

FIG. 11B and FIG. 11C illustrate a proposed rotating mechanism 445 at the central connection area 440 of a handle, such as the forceps/tweezers handle 400, of the present invention. The central connection area 440 splits to form a generally semicircular channel 446 bounded by a generally semicircular inner sleeve 441 and a generally semicircular outer sleeve 442. Also, a radial slot 443 and an ulnar slot 444 are respectively located in the outer sleeve 442 of the central connection area 440.

The distal section 420 of the radial arm 415 and the distal section 430 of the ulnar arm 425 can be of a generally tapered configuration. The distal end 420*a* of the distal section 420 of the radial arm 415 and the distal end 430a of the distal section 430 of the ulnar arm 425 meet at the inside margin 440a of the semicircular channel 446 of the rotating mechanism 445 of the central connection area 440.

For a handle, such as the forceps/tweezers handle 400, of the present invention two cams 419a, 429a are attached to the outer surface of the distal section 420 of the radial arm 415 and the distal section 430 of the ulnar arm 425. The cams 419a, 429a are elevated at edges 419b, 429b of the slots 443, 444. The cams 419a, 429a are designed to engage the slots 443, 444 in the semicircular outer sleeve 442 when the distal section 420 of the radial arm 415 and the distal section 430 of the ulnar arm 425 are advanced into the semicircular channel 446 between the semicircular inner sleeve 441 and the semicircular outer sleeve 442 of the rotating mechanism 445 of the central connection area 440. The cams 419a, 429a are designed to slide in the radial slot 443 and the ulnar slot 444 to retain the radial arm 415 and ulnar arm 425 in the semicircular channel 446. The radial slot 443 and the ulnar slot 444 are designed to allow rotation of the radial arm 415 and the ulnar arm 425 in a range of approximately 35 to 50 degrees in relation to the angle K.

Figure 12A:
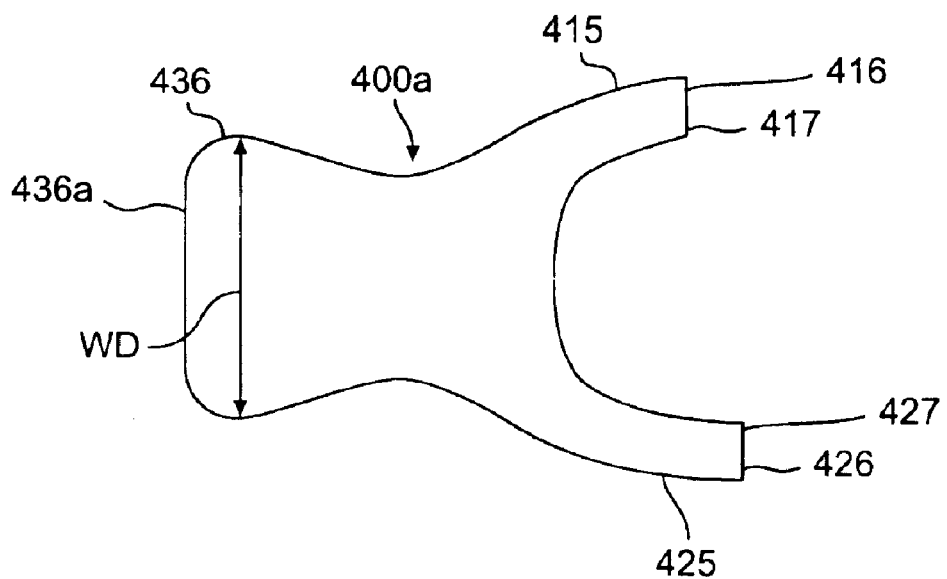
FIGS. 12A and 12B illustrate views of an embodiment of a handle of the present invention having a widened distal end.
Figure 12B:
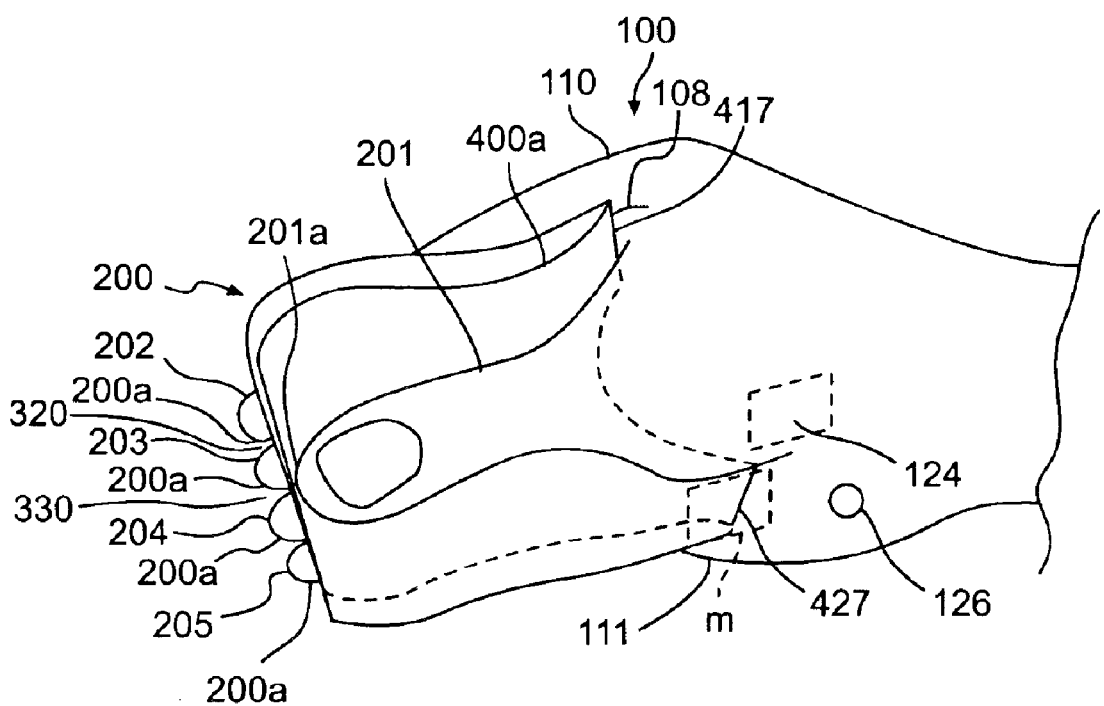

Another variation of the forceps/tweezers handle 400, handle 400a, of the present invention is illustrated in FIG. 12A and FIG. 12B. This variation is related to the width WD of the distal ends 436a of the distal arms 436 of the opposing blades 410 of handles, such as the forceps/tweezers handle 400, of the present invention. The variation on FIGS. 12A and 12B is based on achieving the highest attainable pinch strength that can be produced when the tip 201a of the thumb 201 opposes the center of the tips 200a of the long fingers 200 as discussed in the background information.

As illustrated in FIGS. 1 through 2B, when the hand 100 is in the T Position, the tip 201a of the thumb 201 opposes the space 320 between the tip 200a of the index finger 202 and the tip 200a of the middle finger 203 and the tips 200a of the long fingers 200 end in a line 300. However, in the Forceps Hand Position (FHP), the thumb 201, index finger 202 and middle finger 203 are almost fully extended to meet at Plane B while the ring finger 204 and the small finger 205 are flexed to end at the line 300 as in the T position. In the present variation handle 400a illustrated in FIG. 12B, with the hand 100 in the T Position, the tip 201a of the thumb 201 is repositioned toward the ulnar side 111 of the hand 100 from the space 320 between the tip 200a of the index finger 202 and the tip 200a of the middle finger 203 to the space 330 between the tip 200a of the middle finger 203 and the tip 200a of the ring finger 204.

Therefore, in the variation handle 400a, as illustrated in FIG. 12B, the width WD of the distal end 436a and the distal leg 436 are similar to the width across the long fingers 200 when the hand is in the T Position. The relationship of the radial hinge 416 of the radial arm 415 to the horizontal crease 108 on the radial side 110 of the hand 100 and the relationship of the ulnar hinge 426 of the ulnar arm 425 to area M on the ulnar side 111 of the hand 100 are similar in this variation handle 400a to such relationships in the forceps/tweezers handle 400 of the present invention. Also, the variation handle 400a does not contact the CT area 124 of hand 100.

The variation handle 400a of the forceps/tweezers handle 400 of the present invention has the potential to produce the highest pinch strength at the working end 450. However, generally less pinch strength is necessary to hold an object because typically the thumb 201 and all the long fingers 200 of the hand 100 are used to pinch the distal end 436a of the distal leg 436 of the variation handle 400a of the forceps/tweezers handle 400 of the present invention.

Figure 13A:
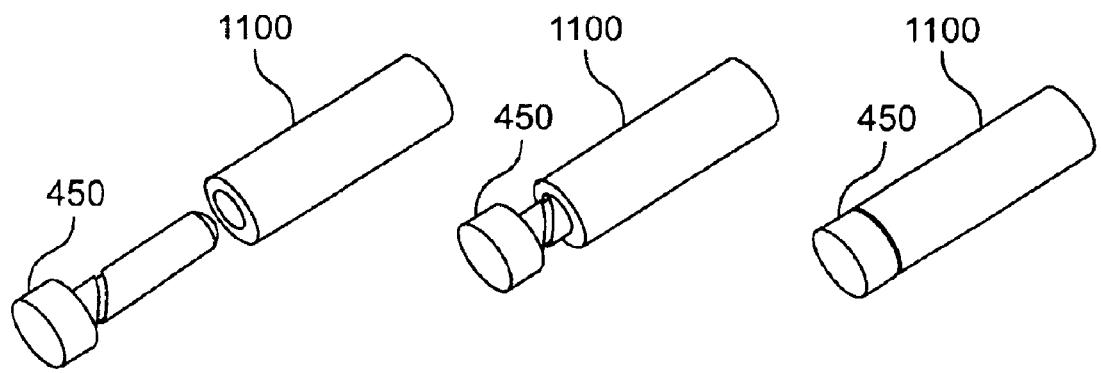
FIGS. 13A through 13K illustrate various connection means at the distal end of a handle of the present invention for connecting various implements to the handle.
Figure 13B:
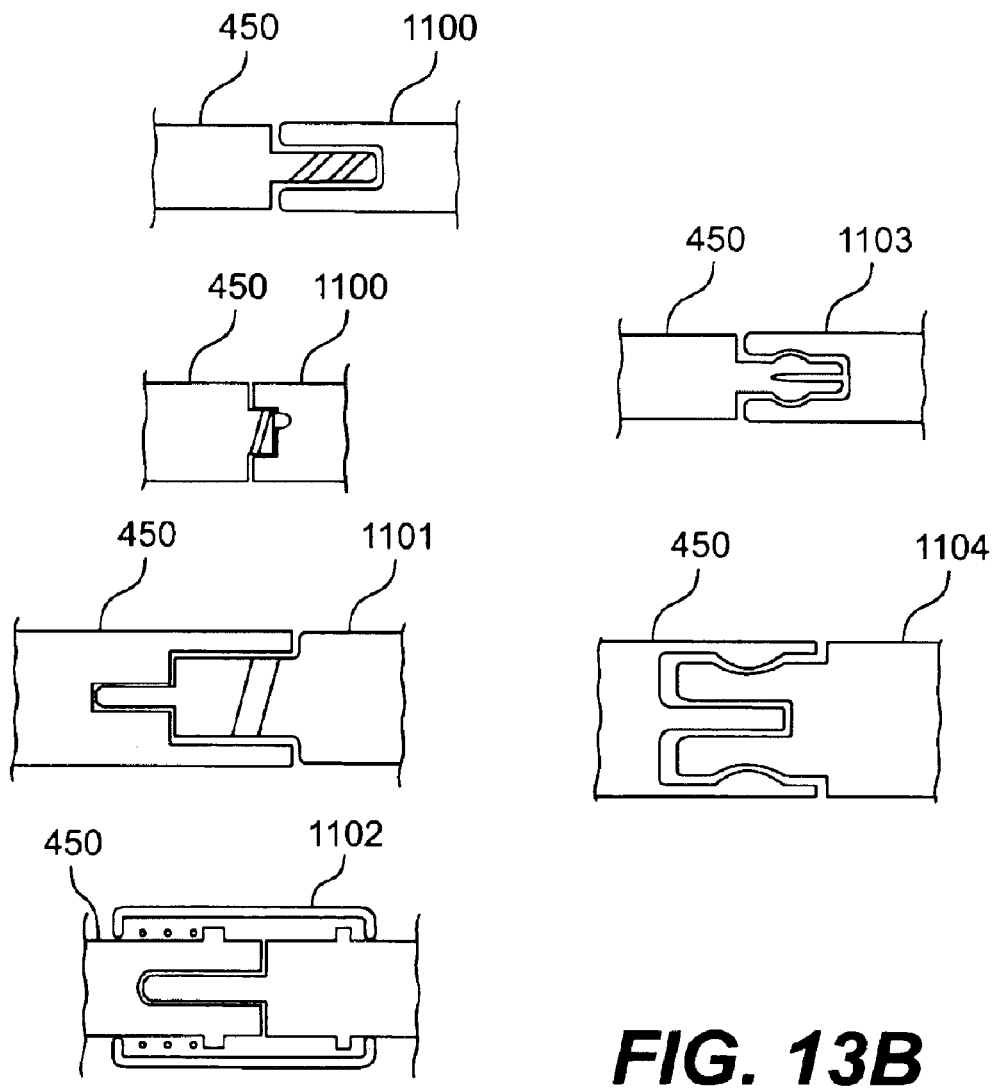
Figure 13C:
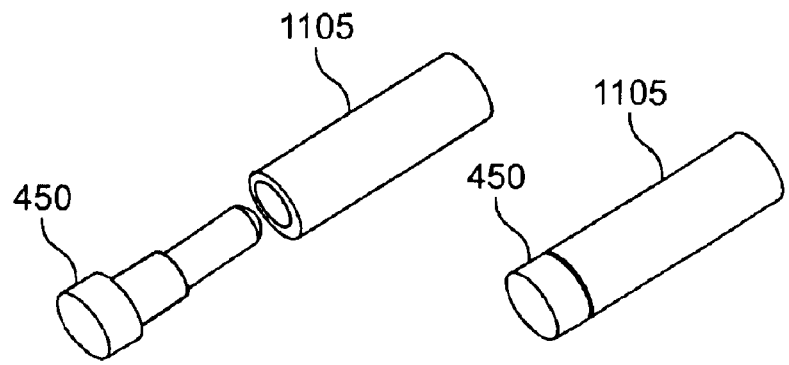
Figure 13D:
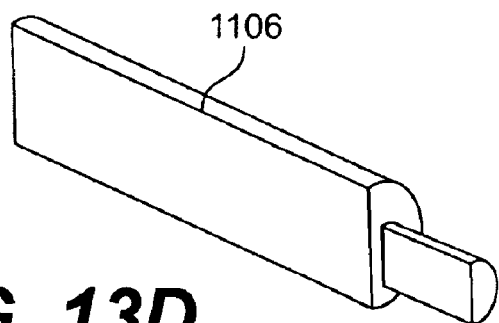
Figure 13E:
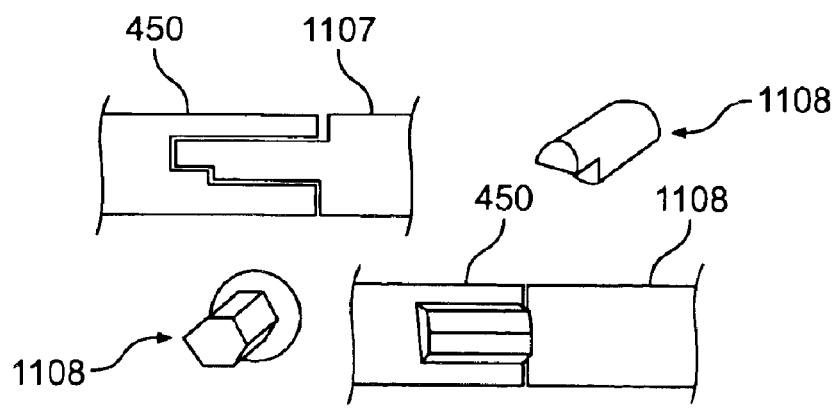
Figure 13F:
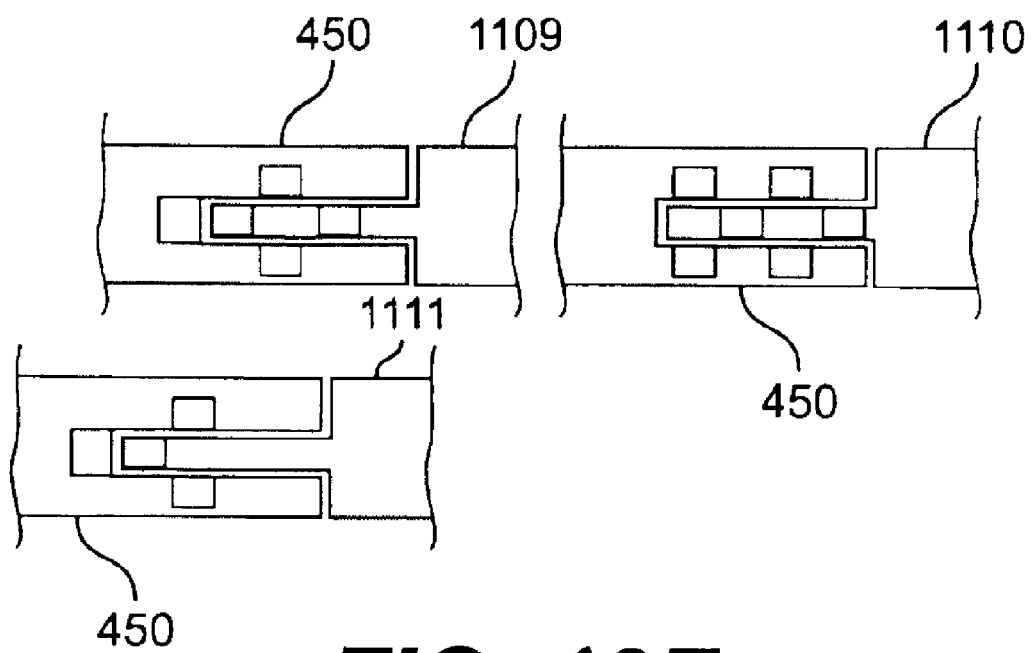
Figure 13G:
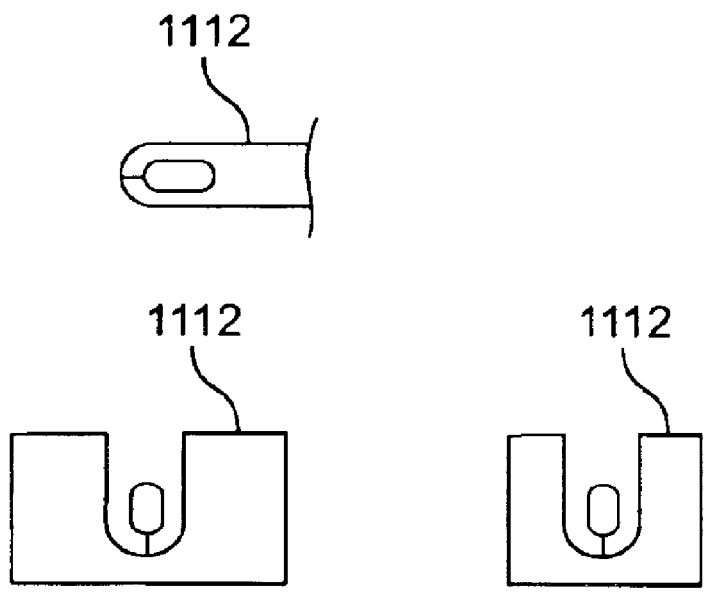
Figure 13H:
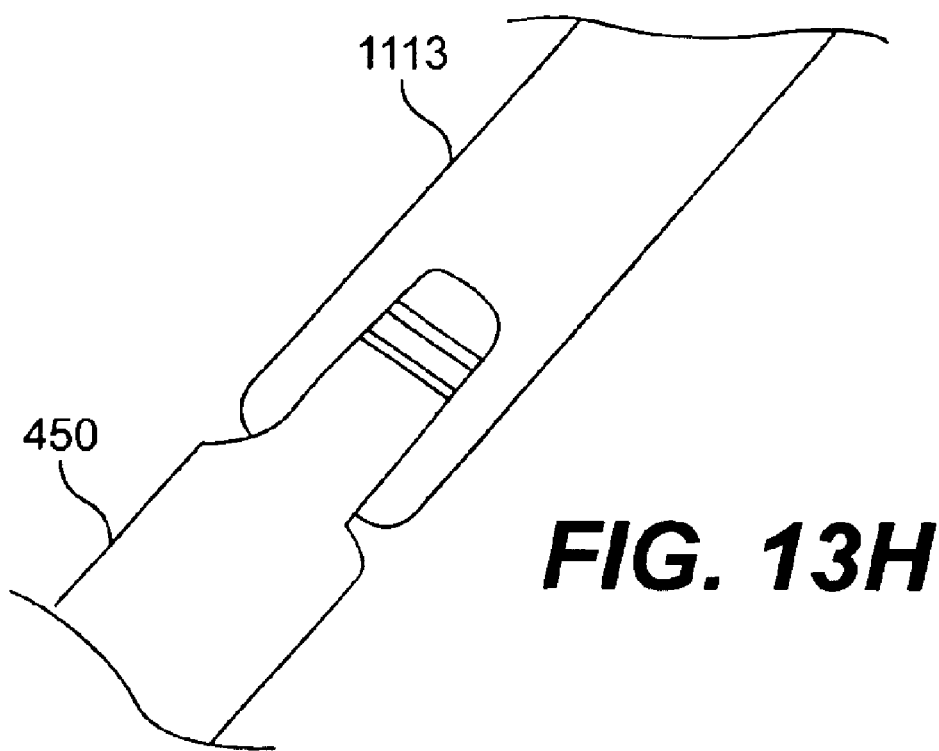
Figure 13I:
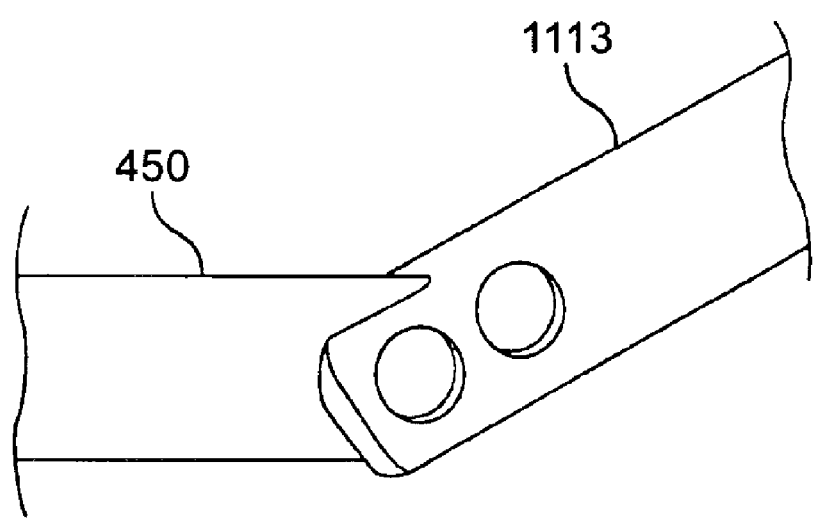
Figure 13J:
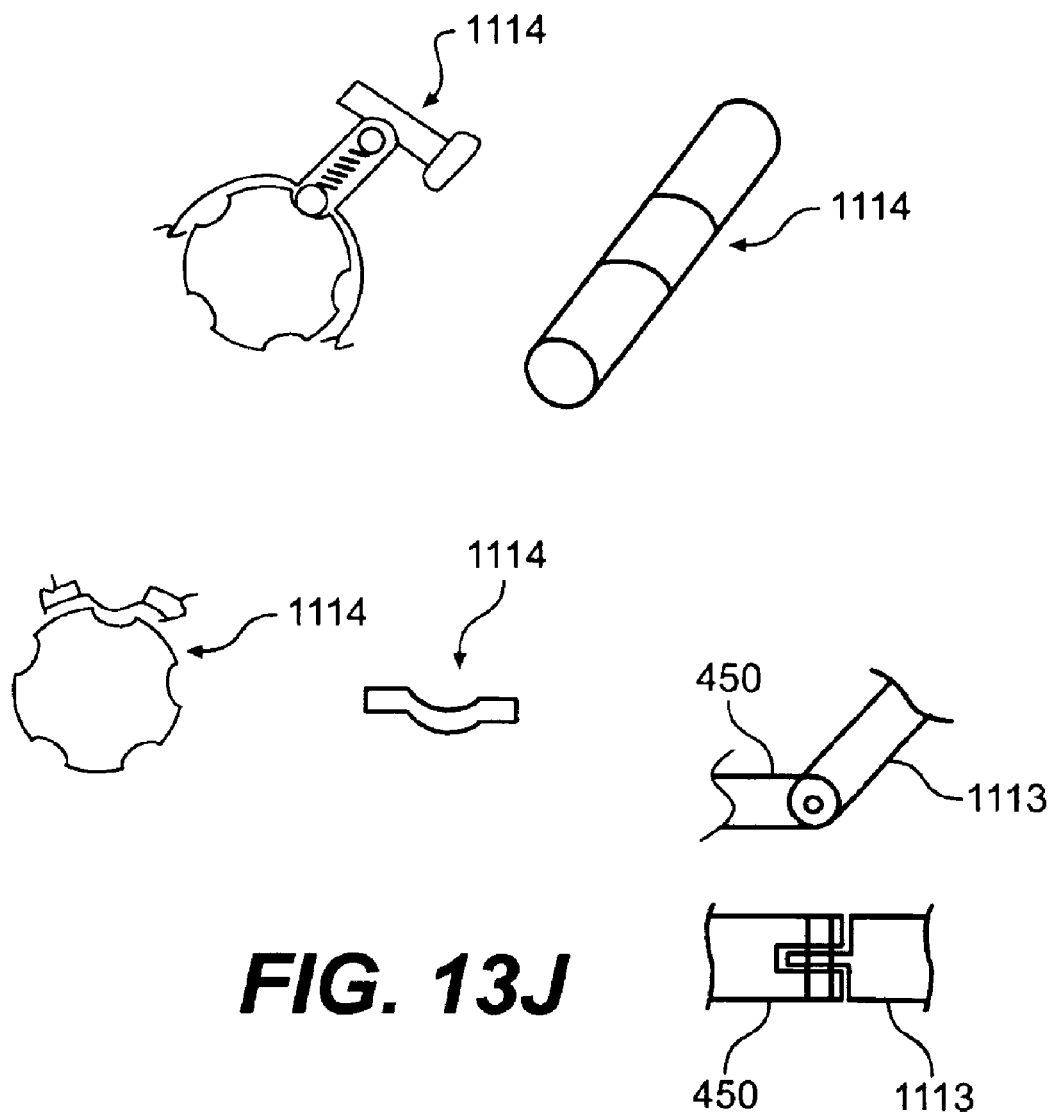
Figure 13K:
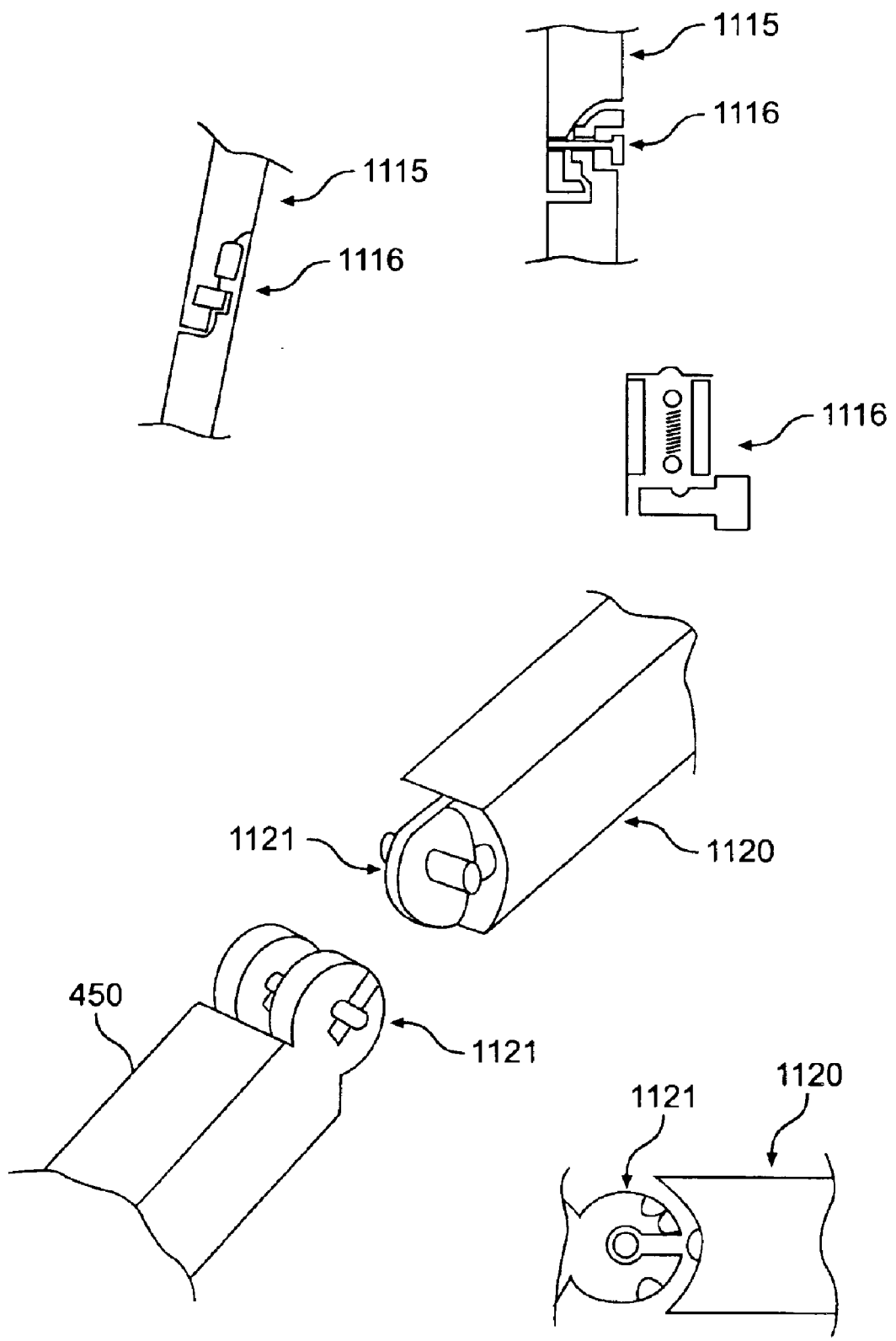

FIGS. 13A through 13K illustrate various connection means joined to or integrated at the distal end 435a, 436a in various embodiments of the handles of the present invention, such as handles 400, 400a, 400b, 400c and 400d of the present invention, for connecting various implements to the handle. For example, FIG. 13A illustrates views of a screw type connecting means 1100 for implements of working ends 450. FIG. 13B illustrates views of screw type connecting means 1100, 1101 and snap-in type connecting means 1102, 1103, 1104 for implements of working ends 450. FIGS. 13C, 13D, 13E, 13F and 13G illustrate views of various magnetic type connecting means 1105, 1106, 1107, 1108, 1109, 1110, 1111, 1112 for implements of working ends 450.

Also, for example, FIGS. 13H through 13K illustrate views of rotating type connecting mechanisms 1113, 1115, 1120, with working parts 1114 for the working mechanism 1113, with working parts 1116 for the working mechanism 1115, and with working parts 1121 for the working mechanism 1120, for working ends 450 of implements, which allow various changes in the position of the working ends 450 of various implements relative to the handle.

Another handle variation 400b of the present invention that changes the direction of motion at the working end 450 of the handle 400b of the present invention is illustrated in FIG. 14A, FIG. 14B, FIG. 14C, FIG. 14D, FIG. 14E, FIG. 15A and FIG. 15B. For example, the direction of movement at the tips of a common forceps is generally parallel to the opposing motion of the thumb 201 to the index finger 202 and middle finger 203. In the variation handle 400b, the motion of the working end/working member 450 of such a handle 400b can be perpendicular to the opposing motion of the thumb 201 to the index finger 202 and the middle finger 203. This changes the motion at the working end/working member 450 of the handle 400b from a side to side motion to an up and down motion in this variation handle 400b of the forceps/tweezers handle 400 of the present invention.

A common example of a surgical instrument used with an up and down opening and closing motion for cutting or biopsy of tissue is a pituitary rongeur. Opening and closing the ring handles of the common pituitary rongeur position the thumb 201 and a long finger 200 of the hand 100 in a proximal and distal relationship to each other. The proximal-distal motion of the thumb 201 and a lone finger 200 activates a sliding member to move in the proximal-distal direction. The sliding member activates the working member to open and close. Using such an instrument in which the thumb 201 and a long finger 200 of the hand 100 move in a proximal and distal direction typically is not as comfortable for the hand 100 as using the side to side opposing motion utilized in the variation handle 400b of the forceps/tweezers handle 400 of the present invention.

Figure 14A:
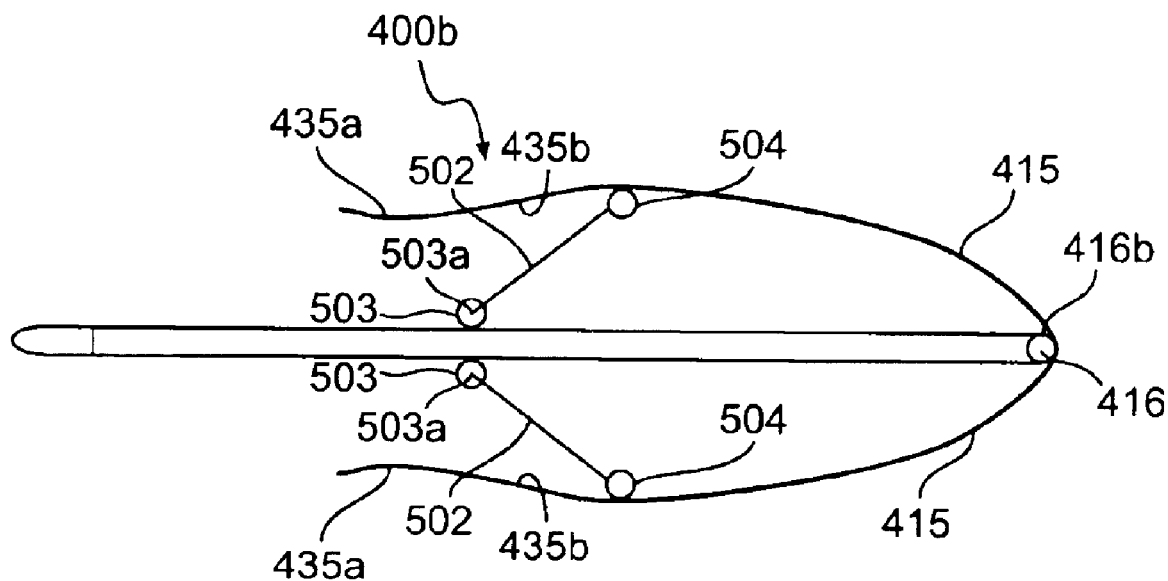
FIGS. 14A through 14E illustrate embodiments of mechanisms to change the direction and orientation of pinch with respect to a handle of the present invention, such as from a side-to-side horizontal direction to an up and down vertical direction in relation to a handle.
Figure 14E:
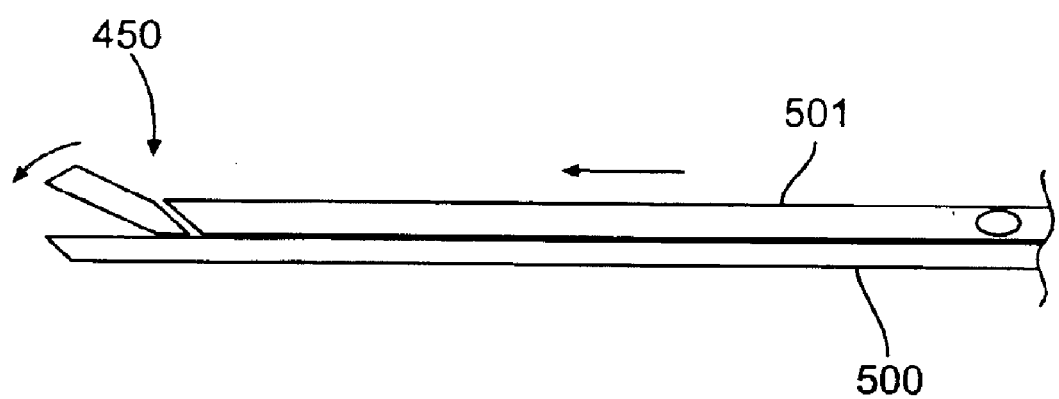
Figure 14B:
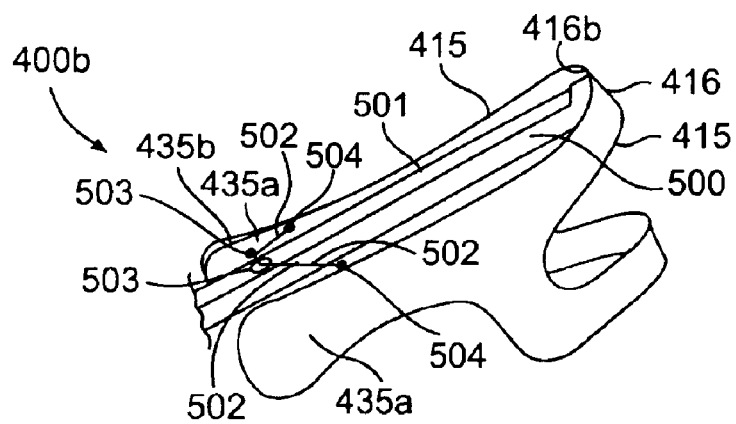
Figure 14C:
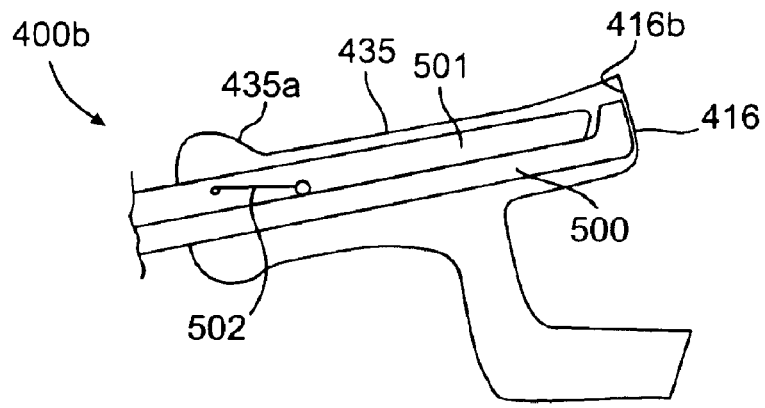
Figure 14D:
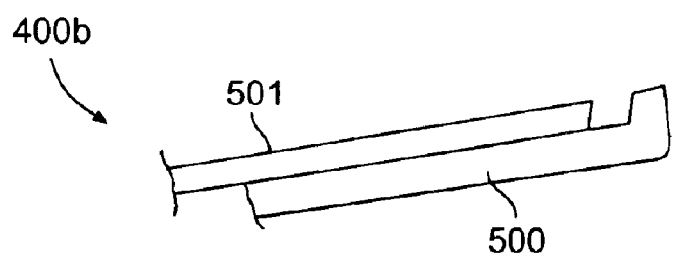

In this variation handle 400b illustrated in FIG. 14A, FIG. 14B, FIG. 14C, FIG. 15B, FIG. 15C and FIG. 15D, a fixed member 500 is attached to the inside 416b of the radial hinge 416 of the radial arm 415 of the variation handle 400b of forceps/tweezers handle 400 of the present invention. Above the fixed member 500 is a sliding member 501 that activates the working end/working member 450 to open and close as illustrated in FIG. 14E. Brace members 502 connect the sliding member 501 to the inside aspect 435b of the distal ends 435a of the distal legs 435. Sliding member hinges 503 attach the ends 503a of the brace members 502 to the sliding members 501 and hinges 504 attach brace members 502 to the inner aspect 435b of the distal ends 435a of the distal legs 435 of variation handle 400b of the present invention.

Pinching the distal ends 435a of the distal legs 435 of the variation handle 400b of the present invention moves the brace members 502 at the hinges 503, 504 to move the sliding member 501. Furthermore, the fixed member 500 can rotate the working end/working member 450 when a rotating mechanism is attached to the inside 416b of the radial hinge 416.

Squeezing the distal ends 435a of the distal legs 435 of the variation handle 400b of the forceps/tweezers handle 400 of the present invention when the sliding member hinges 503 of the brace members 502 are placed distal on the sliding member 501 push the sliding member 501 away from the hand 100. However, as illustrated in FIG. 15C, squeezing the distal ends 435a of the distal legs 435 of the variation handle 400b of the forceps/tweezers handle 400 of the present invention, when the sliding member hinges 503 attach at ends 503b of the brace members 502 and the sliding member hinges 503 are placed proximal on the sliding member 501, moves the sliding member 501 toward the hand 100. Moving the sliding member 501 can actuate any of a variety of mechanisms, as the working end/working member 450, attached to the end of the sliding member 501, such as to close a fine scissors or other mechanism, such as illustrated in FIG. 14E.

Also, referring to FIGS. 14A through 14E, the variation handle 400b of the present invention can also be utilized in conjunction with various endoscopic or surgical tools, as well as other types of working tools that work at a distance from the operator.

In various embodiments of the forceps/tweezers handle 400 of the present invention, the gap between the distal ends 435a of the distal legs 435 can be wider than the distance between the working ends 450 of the forceps/tweezers handle 400 of the present invention. The gap between the distal ends 435a of the distal legs 435 also depends on the inherent spring qualities of the material used to make the opposing blades 410 of a handle, such as the forceps/tweezers handle 400, of the present invention. The gap between the distal ends 435a of the distal legs 435 for surgical forceps and surgical instruments using the forceps/tweezers handle 400 of the present invention should generally remain between one and two centimeters. A smaller gap can increase flexion and can add strain to the PIP joints of the long fingers 200 and can increase flexion and can add strain to the metacarpal phalangeal joint 201c of the thumb 201. A larger gap also requires more gross than fine motor skills to pinch.

Figure 15A:
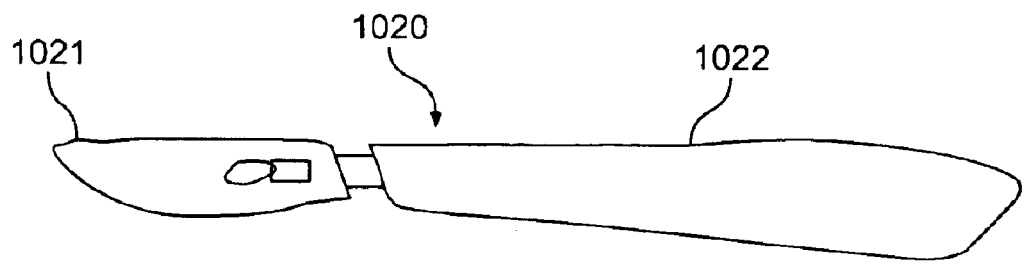
FIGS. 15A, 15B, 15C and 15D illustrate a spring loaded mechanism, such as for a surgical scalpel guard, integrated with a handle of the present invention to provide for retraction and extension of an implement for use with a handle.
Figure 15B:
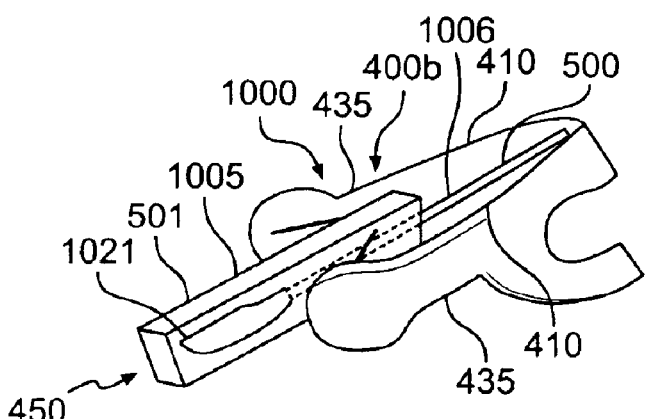
Figure 15C:
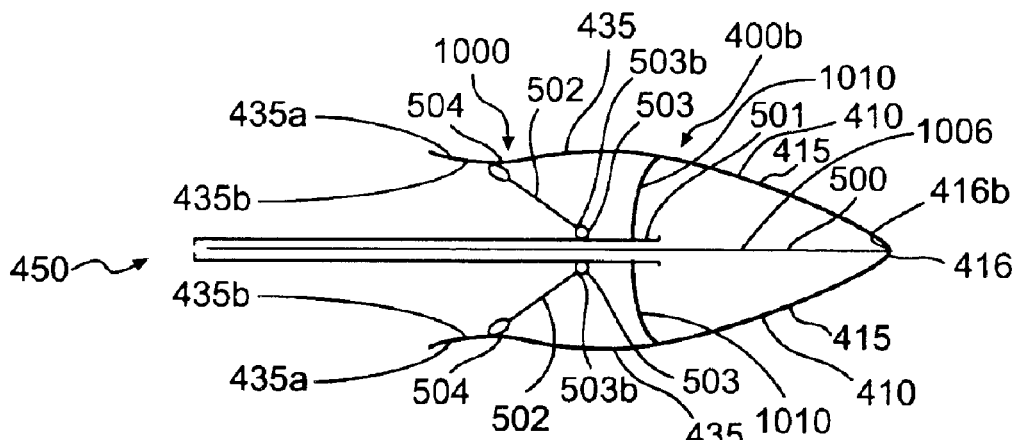

Continuing with reference to FIGS. 15A through 15D, the standard scalpel 1020, illustrated in FIG. 15A, is in the shape of a stylus and is a fixture in surgery. During the course of surgery, a scalpel blade 1021 can contact pathogens harboring in the patient's serum. One problem associated with the standard scalpel handle 1022 is penetrating wounds to operating room personnel. Inadvertent sharp wounds can transmit diseases to the assisting personnel. An automatic retractable blade guard could prevent sharp wounds.

Figure 15D:
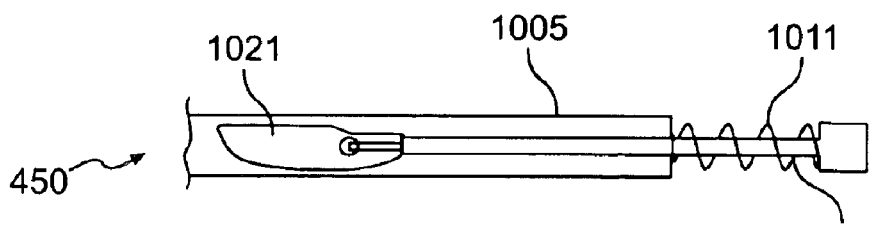

As previously discussed, variation handle 400b of the forceps/tweezers handle 400 of the present invention can move a sliding member 501 in relation to a fixed member 500. FIG. 15B illustrates a retractable scalpel 1000, as the working end!working member 450, with the sliding member 501 including a retractable sliding guard 1005 that surrounds a fixed scalpel member 1006, as the fixed member 500, including an attached scalpel blade 1021. FIG. 15B illustrates a flat spring member 1010, as a first spring member, attached to the opposing blades 410 and the retractable sliding guard 1005. Alternately, a coil spring member 1011, as a second spring member, can be attached to the fixed scalpel member 1006 and the retractable sliding guard 1005 as shown in FIG. 15D. When the distal ends 435a of the distal legs 435 of the opposing blades 410 of the fixed scalpel member 1006 of variation handle 400b of the forceps/tweezers handle 400 of the present invention are squeezed, the brace members 502 push the proximal hinges 503 to move the retractable sliding guard 1005 toward the hand of the operator to expose the scalpel blade 1021. When the distal ends 435a of the distal legs 435 are released, the retractable sliding guard 1005 automatically covers the scalpel blade 1021.

One advantage of the retractable scalpel 1000 with the forceps/tweezers handle variation handle 400b of the present invention is promoting protection from sharp injury in the operating room. Another advantage is that the retractable scalpel 1000 is based on the anatomic Forceps Hand Position (FHP), which can make the retractable scalpel 1000 more comfortable for the hand 100 to hold and manipulate.

Figure 16A:
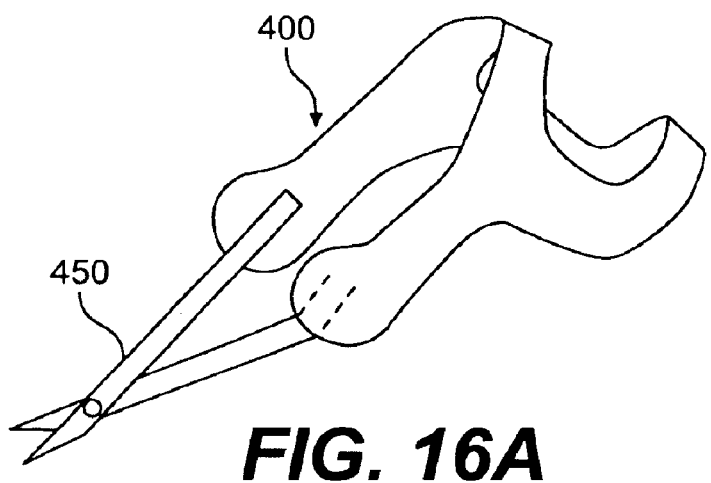
FIGS. 16A and 16B illustrate working ends attached to a handle of the present invention with the working end of FIG. 16A being a microscissors and the working end of FIG. 16B being a reverse tweezers.
Figure 16B:
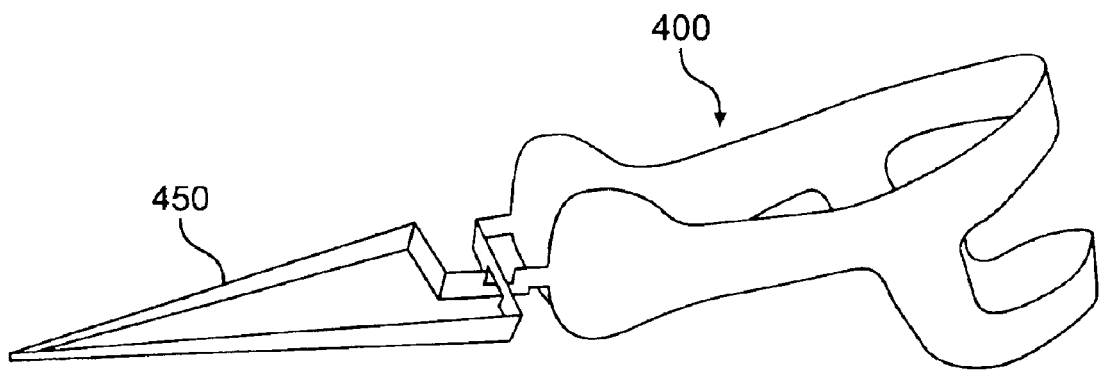

FIGS. 16A and 16B illustrate working ends 450 attached to a forceps/tweezers handle 400 of the present invention with the working end 450 of FIG. 16A being a microscissors and the working end 450 of FIG. 16B being a reverse tweezers.

Figure 17:
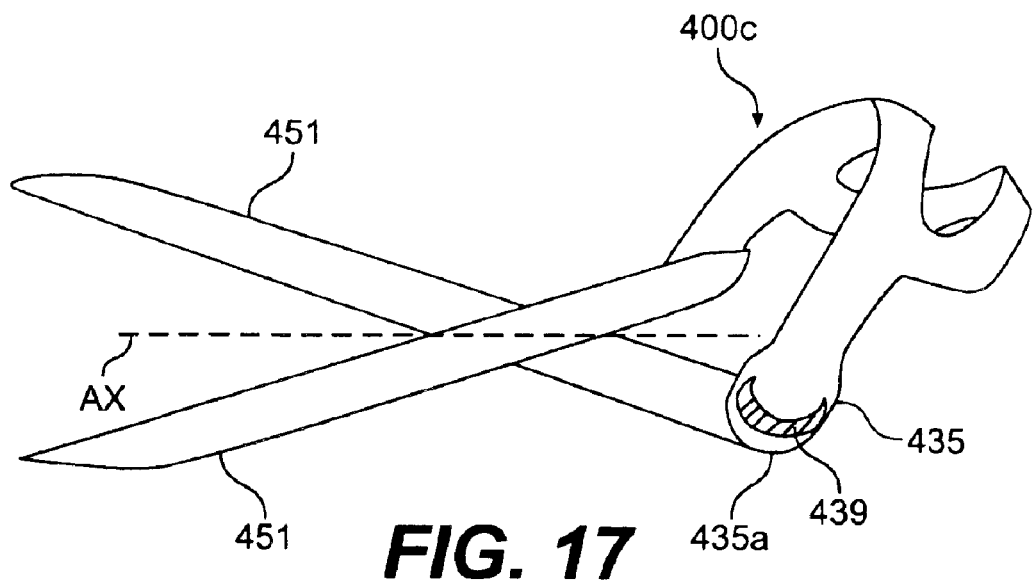
FIG. 17 illustrates of an embodiment of a handle of the present invention attached to a standard size scissors.

FIG. 17 illustrates a standard size scissors variation handle 400c of the forceps/tweezers handle 400 of the present invention. Attachments of working ends 450 of many surgical instruments, such as the microscissors attachment 450, illustrated in FIG. 16A, generally extend from the distal end 435a of the distal legs 435 of the opposing blades 410 in the same general direction as the thumb 201, index finger 202 and middle finger 203 when the hand 100 is in the Forceps Hand Position (FHP). In the standard size scissors variation handle 400c of the forceps/tweezers handle 400 of the present invention, illustrated in FIG. 17, the standard size scissors variation handle 400c attaches to a standard size scissors blades 451.

However, the relationship of the hand 100 to the standard size scissors blades 451 of the standard size scissors variation handle 400c is typically not in the same general direction as the thumb 201, index finger 202 and middle finger 203 when the hand 100 is in the Forceps Hand Position (FHP). The direction of the standard size scissors blades 451 of the standard size scissors variation handle 400c in relation to the hand 100 is related to the relationship of the hand 100 to line J illustrated in FIG. 2A. Line J connects the space 310 between tip 202b of the index finger 202 and tip 203b of the middle finger 203 and the dorsal surface 252a of the DIP joint 252 of the small finger 205 when the hand 100 is in the Forceps Hand Position (FHP). The attachment of the blades 451 of a standard scissors to the standard size scissors variation handle 400c is such that the axis AX passes centrally through the blades 451 and the axis AX is parallel to line J.

The rings 439 on distal end 435a of distal legs 435 of the standard size scissors variation handle 400c allow the opposing thumb 201, index finger 202 and middle finger 203 to open the blades 451 of a standard scissors for the standard size scissors variation handle 400c. The distal pad 201b of the thumb 201, the distal pad 202b of the index finger 202 and the distal pad 203b of the middle finger 203 oppose to close the blades 451 of a standard scissors for the standard size scissors variation handle 400c.

In common scissors, the fingers of the hand 100 meet the ring like extensions of the scissors blades. The thumb 201 opposes the index finger 202 and the middle finger 203 and they enter ring handles to open and close the common scissors. Typically, in such common scissors, hand support is generally poor. Also, closing the scissors places the thumb 201 uncomfortably close to the opposing index finger 202 and the hand 100 is generally not integrated into the handle.

The standard size scissors handle variation 400c of the forceps/tweezers handle 400 of the present invention has advantages over a common scissors. These advantages are related to contact with the hand 100 at the horizontal crease 108 on the radial side 110 of the hand 100, at area M on the ulnar side 111 of the hand 100, at the palmar surface 210 of the ring finger 204 and at the palmar surface 220 of the small finger 205. Furthermore, the ring finger 204 and the small finger 205 pull the handle 400c into the hand. These features add to support, given the scissors variation handle 400c adapted to the forceps/tweezers handle 400 of the present invention, and integrate the hand 100 into the scissors variation handle 400c adapted to the forceps/tweezers handle 400 of the present invention. These areas of contact with the standard size scissors variation handle 400c, adapted to the forceps/tweezers handle 400 of the present invention, integrate the entire hand 100 and not only the thumb 201, index finger 202 and middle finger 203 to open, close and hold a scissors.

Figure 18A:
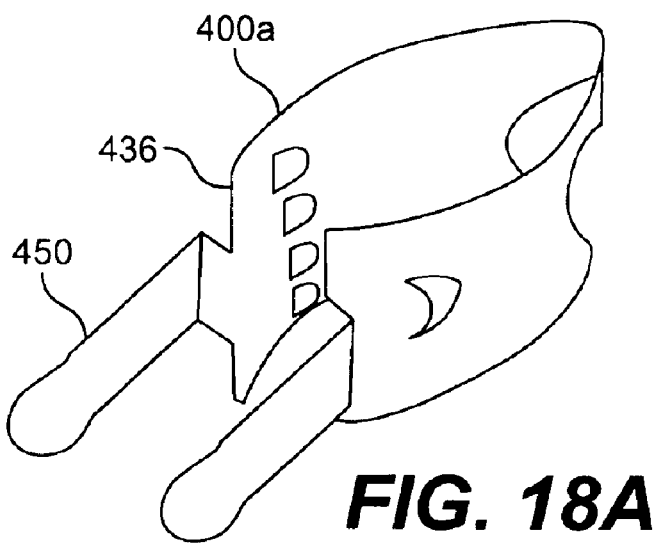
FIGS. 18A, 18B and 18C illustrate views of an embodiment of a handle of the present invention that has a wider distal end, with a working end positioned at the wider distal end, such as for retrieving items such as files from a file cabinet or loose items on a surface.
Figure 18B:
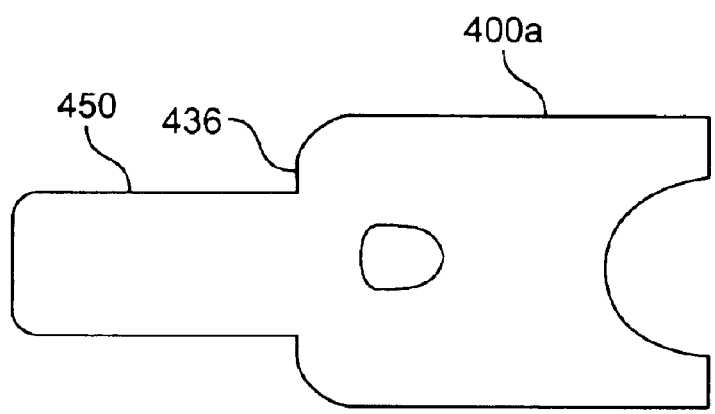
Figure 18C:
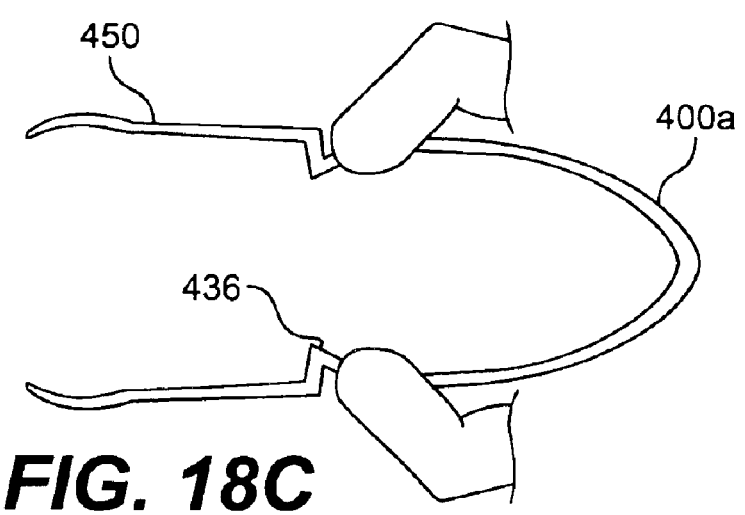

FIGS. 18A, 18B and 18C illustrate views of an embodiment of the handle 400a of FIGS. 12A and 12B of the present invention that has a wider distal end 436, with a working end 450, the working end 450 including an implement, positioned at the wider distal end 436, such as for retrieving items such as files from a file cabinet or loose items on a surface.

Figure 19A:
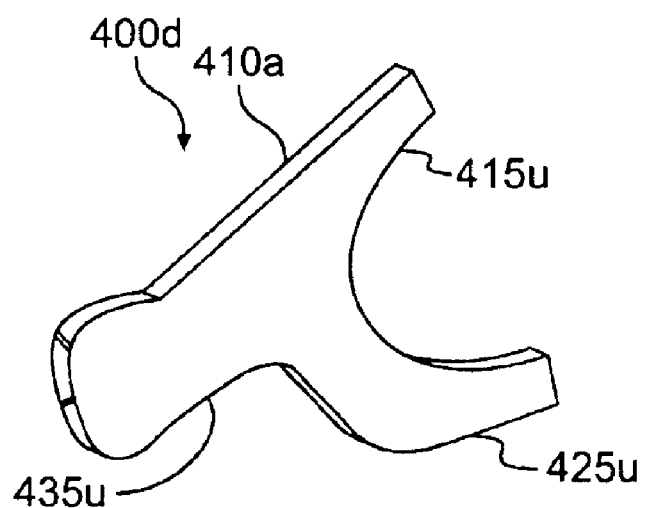
FIGS. 19A, 19B, 19C and 19D illustrate various embodiments of a handle of the present invention that can have devices integrated with a handle.
Figure 19B:
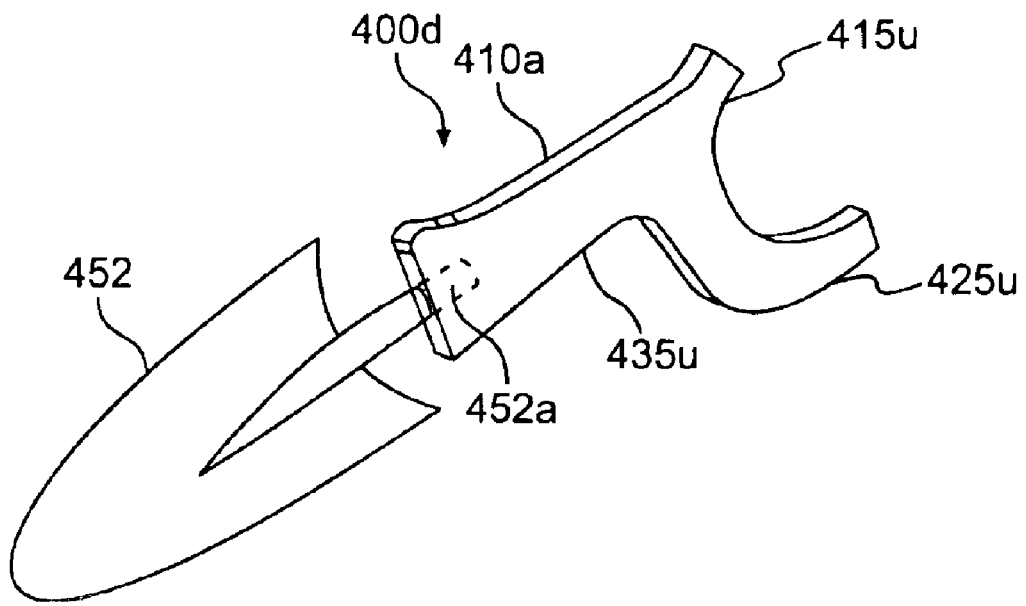
Figure 19C:
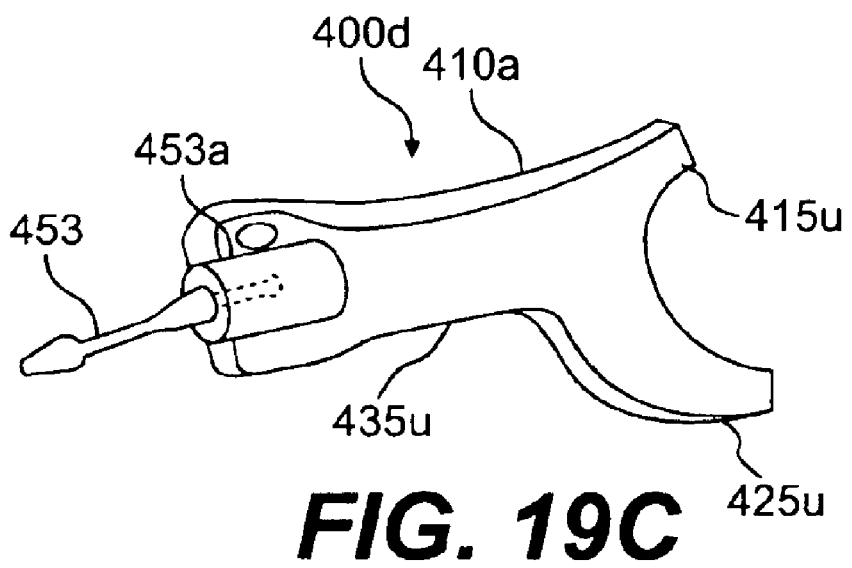
Figure 19D:
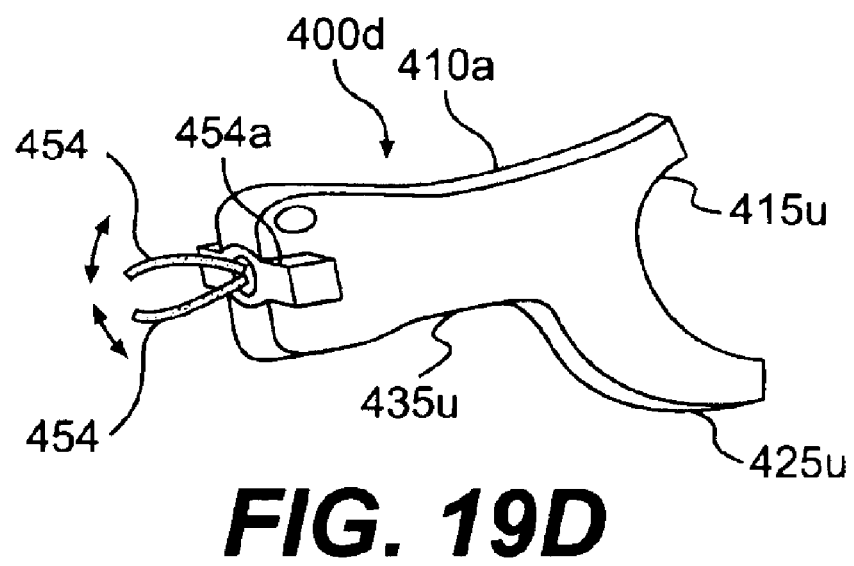

FIGS. 19A, 19B, 19C and 19D illustrate various embodiments of a unitary handle 400d of the present invention that can have devices integrated with a handle. FIGS. 19A through 19D illustrate embodiments of the unitary handle 400d of the present invention having a single "Y" configuration with a unitary blade 410a, rather than a pair of opposing blades 410. The unitary radial arm 415u and the unitary ulnar arm 425u and the unitary distal leg 435u engage corresponding portions of the hand 100 as the forceps/tweezers handle 400 of the present invention as previously described. FIG. 19B illustrates an embodiment of the unitary handle 400d of the present invention having an implement 452 attached by a suitable connection means 452a to the handle 400d. FIG. 19C illustrates an embodiment of the unitary handle 400d of the present invention that incorporates a motor driving means 453a for rotation or movement of a working end 453 or an implement 453, such as a drill bit or screwdriver attachment. FIG. 19D illustrates an embodiment of the unitary handle 400d of the present invention having a motor driving means 454a for opening and closing a working end 454 or multiple working ends 454 of an implement, such as motorized tweezers.

In summary, handles of a design according to the present invention can be molded or formed into and contiguous with any of many types of equipment commonly held by a hand. Furthermore, handles based on the design method of the present invention can be attached to or integrated into objects that can be lifted, rotated, moved, carried, etc. Such handles of the present invention can advantageously be attached or integrated into or with an object or working end. Additionally, such handles of the present invention can be designed to swivel and/or rotate on various axes at a location of attachment. For example, the handle can be attached to a shaft by an extension member, such as for turning.

Also, in the handles of the present invention, various materials can be used for fabrication of the handles as, for example, various woods, metals, plastics, composites, rubber compounds, latex's and organic or inorganic materials, suitable for the particular application of a handle of the present invention. Further, various materials can be added to augment and personalize the fit of a handle of the present invention.

The principles, preferred embodiments and modes of operation of the present invention have been described in the foregoing specification. However, the invention which is intended to be protected is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A forceps type apparatus for use with a hand, comprising:

a radial section, the radial section including a pair of radial arms meeting at a radial hinge portion, the radial hinge portion for engaging a portion of the radial side of the palmar surface of the band;

a middle section, the middle section adjoining the radial section without placing substantial pressure on a surface of the hand located over the carpal tunnel;

an ulnar section, the ulnar section adjoining the middle section, and with the ulnar section including a pair of ulnar arms meeting at an ulnar hinge portion, the ulnar hinge portion for engaging a portion of the ulnar side of the palmar surface of the hand; and a pair of opposing blades, with each opposing blade extending from at least one of the radial section, the middle section and the ulnar section, wherein the radial hinge portion and the ulnar hinge portion engage respective portions of the palmar surface of the hand so as to position the forceps type apparatus within the hand without placing substantial pressure on a surface of the hand located over the carpal tunnel.

2. The forceps type apparatus according to claim 1, wherein the forceps type apparatus is made of a material such that the forceps type apparatus has a spring-like nature so as to selectively open after closing.

3. The forceps type apparatus according to claim 1, further comprising a working end at the end of at least one of the pair of opposing blades.

4. The forceps type apparatus according to claim 3, wherein an implement is selectively attached to or detached from the working end of a corresponding opposing blade.

5. The forceps type apparatus according to claim 4, wherein each implement is selectively attached to or detached from the working end of the corresponding opposing blade by a suitable connection means.

6. The forceps type apparatus according to claim 5, wherein the implement is for grasping, pinching or cutting.

7. The forceps type apparatus according to claim 1, wherein the radial hinge portion and the ulnar hinge portion engage respective portions of the palmar surface of the hand so as to position the forceps type apparatus within the hand without engaging a surface of the hand located over the carpal tunnel.

8. The forceps type apparatus according to claim 1, wherein the pair of opposing blades is for receiving the thumb and at least one of the long fingers of the hand.

9. The forceps type apparatus to claim 1, wherein the forceps type apparatus is generally of a Y shape, an asymmetrical Y shape or a sling-shot shape configuration.

10. The forceps type apparatus according to claim 1, further comprising a connection area where a corresponding radial arm, an ulnar arm and a blade meet.

11. The forceps type apparatus according to claim 10, wherein the connection area includes a rotational mechanism for rotational movement of the corresponding radial arm and the corresponding ulnar arm.

12. The forceps type apparatus according to claim 11, wherein the rotational mechanism provides an angular range for the rotational movement.

13. The forceps type apparatus according to claim 1, further comprising a rotational mechanism for rotational movement of at least one of the pair of radial arms and the pair of ulnar arms.

14. The forceps type apparatus according to claim 13, wherein the rotational mechanism provides an angular range for the rotational movement.

15. The forceps type apparatus according to claim 1, wherein the forceps type apparatus includes at least one support area for supporting the forceps type apparatus when the hand is holding the forceps type apparatus, with the at least one support area including a support area on at least one of the radial hinge portion for engaging the radial side of the palmar surface of the hand and the ulnar hinge portion for engaging the ulnar side of the palmar surface of the hand.

16. The forceps type apparatus according to claim 1, wherein the pair of ulnar arms includes at least one contact area for receiving at least one of the ring finger and the small finger of the hand.

17. The forceps type apparatus according to claim 1, wherein the pair of ulnar arms includes a ring finger contact area for receiving the ring finger of the hand and a small finger contact area for receiving the small finger of the hand.

18. The forceps type apparatus or handle according to claim 17, wherein a step portion is positioned on the pair of ulnar arms between the ring finger contact area and the small finger contact area to conform the palmar surface of the ring finger to the ring finger contact area and the palmar surface of the small finger to the small finger contact area.

19. The forceps type apparatus according to claim 1, wherein at least one of the pair of radial arms and the pair of ulnar arms includes an extension for adjusting the forceps type apparatus to correspond to a hand size.

20. The forceps type apparatus according to claim 19, wherein each extension is selectively added to a corresponding one of the pair of radial arms or the pair of ulnar arms for adjusting the forceps type apparatus to correspond to a hand size.

21. The forceps type apparatus according to claim 20, wherein each extension can include a plurality of shapes for respectively engaging a corresponding portion of the radial side of the palmar surface of the hand or for engaging a corresponding portion of the ulnar side of the palmar surface of the hand.

22. The forceps type apparatus according to claim 21, wherein the plurality of shapes for a corresponding extension can include a generally round shape.

23. The forceps type apparatus according to claim 1, further comprising a spring mechanism positioned between the pair of opposing blades, wherein the spring mechanism maintains the forceps type apparatus in a resting position.

24. The forceps type apparatus according to claim 1, further comprising a clamping mechanism engaging the pair of opposing blades, wherein the clamping mechanism selectively maintains a range of positions including an open position, a partially closed position and a closed position for the forceps type apparatus.

25. The forceps type apparatus according to claim 1, wherein the forceps type apparatus comprises at least one ring member for receiving a corresponding at least one of the thumb or at least one of the long fingers of the hand.

26. The forceps type apparatus according to claim 25, further comprising at least one ring member positioned on each of the pair of opposing blades, wherein each ring member on the pair of opposing blades enables the pair of opposing blades of the forceps type apparatus to maintain a spread apart position.

27. The forceps type apparatus according to claim 1, wherein the width of the distal end of at least one of the pair of opposing blades corresponds to the width across the long fingers of the hand.

28. The forceps type apparatus according to claim 1, wherein the width of the distal end of at least one of the pair of opposing blades corresponds to the width across the long fingers of the hand to maximize the pinch strength attainable when the thumb is positioned to centrally oppose the long fingers of the hand.

29. The forceps type apparatus according to claim 1, wherein a suitable connection means for selectively attaching or detaching a corresponding implement is located at the distal end of a corresponding opposing blade.

30. The forceps type apparatus according to claim 29, wherein the suitable connection means comprises a rotating type connecting mechanism for changing a position of a corresponding implement relative to the corresponding forceps type apparatus.

31. The forceps type apparatus according to claim 1, wherein the forceps type apparatus includes means for changing the motion of the opposing blades into another motion, wherein the means for changing the motion changes a side to side motion of the opposing blades into a direction of motion that is oriented perpendicular to the side to side motion of the opposing blades.

32. The forceps type apparatus according to claim 1, wherein the forceps type apparatus includes means for changing the motion of the of the opposing blades into a motion for a working end of the forceps type apparatus.

33. The forceps type apparatus according to claim 32, wherein the forceps type apparatus includes means for rotational movement for rotating the position of the working end of the forceps type apparatus.

34. The forceps type apparatus according to claim 32, wherein the means for changing the motion comprises a fixed member positioned in extended relation from the radial hinge portion of the pair of radial arms, and a sliding member positioned adjacent to the fixed member, with the movement of the opposing blades moving the sliding member for activating the motion for the working end.

35. The forceps type apparatus according to claim 34, wherein the means for changing the motion further comprises at least one brace member for movement of the sliding member for activating the motion for the working end.

36. The forceps type apparatus according to claim wherein a corresponding brace member is attached to the forceps type apparatus by a corresponding hinge member and to the sliding member by a corresponding hinge member for moving the sliding member to activate the motion for the working end.

37. The forceps type apparatus according to claim 36, wherein the hinge member attached to the forceps type apparatus is positioned distally relative to the hinge member attached to the sliding member.

38. The forceps type apparatus according to claim 36, wherein the hinge member attached to the forceps type apparatus is positioned proximally relative to the hinge member attached to the sliding member.

39. The forceps type apparatus according to claim 36, wherein the means for changing the motion further comprises a first spring member attached to the sliding member and attached to the forceps type apparatus.

40. The forceps type apparatus according to claim 39, wherein the means for changing the motion further comprises a second spring member attached to the fixed member and attached to the sliding member of the forceps type apparatus.

41. The forceps type apparatus according to claim 40, wherein the hinge member attached to the forceps type apparatus is positioned distally relative to the hinge member attached to the sliding member.

42. The forceps type apparatus according to claim 41, wherein the working end comprises a scalpel, the scalpel comprises the fixed member, and the sliding member comprises a retractable guard for selectively retracting and exposing a blade of the scalpel.

43. The forceps type apparatus according to claim 40, wherein the working end comprises a surgical tool, the surgical tool comprises the fixed member, and the sliding member comprises a retractable guard for selectively retracting and exposing the surgical tool.

44. The forceps type apparatus according to claim 40, wherein the working end comprises a tool, the tool comprises the fixed member, and the sliding member comprises a retractable guard for selectively retracting and exposing the tool.

45. The forceps type apparatus according to claim 40, wherein the working end comprises the fixed member and the sliding member comprises a retractable guard for selectively surrounding and exposing the working end.

46. The forceps type apparatus according to claim 34, wherein the working end comprises a scalpel, the scalpel comprises the fixed member, and the sliding member comprises a retractable guard for selectively retracting and exposing a blade of the scalpel.

47. The forceps type apparatus according to claim 34, wherein the working end comprises a tool, the tool comprises the fixed member, and the sliding member comprises a retractable guard for selectively retracting and exposing the tool.

48. The forceps type apparatus according to claim 34, wherein the working end comprises the fixed member and the sliding member comprises a retractable guard for selectively surrounding and exposing the working end.

49. The forceps type apparatus according to claim 32, wherein the means for changing the motion comprises a fixed member positioned with the forceps type apparatus and a sliding member positioned adjacent to the fixed member, with the sliding member being linked with the working end for activating the motion for the working end.

50. The forceps type apparatus according to claim 49, wherein the working end comprises a scalpel, the scalpel comprises the fixed member, and the sliding member comprises a retractable guard for selectively retracting and exposing a blade of the scalpel.

51. The forceps type apparatus according to claim 49, wherein the working end comprises a tool, the tool comprises the fixed member, and the sliding member comprises a retractable guard for selectively retracting and exposing the tool.

52. The forceps type apparatus according to claim 32, wherein the forceps type apparatus comprises a surgical tool having a retractable guard for selectively surrounding and exposing the working end of the surgical tool.

53. The forceps type apparatus according to claim 1, wherein the forceps type apparatus comprises a tool having a retractable guard for selectively surrounding and exposing the tool.

54. The forceps type apparatus according to claim 1, wherein the forceps type apparatus comprises a tool.

55. The forceps type apparatus according to claim 1, wherein the forceps type apparatus comprises a surgical tool.

56. The forceps type apparatus according to claim 1, wherein the forceps type apparatus comprises an endoscopic surgical tool.

57. The forceps type apparatus according to claim 1, wherein the forceps type apparatus comprises a microscissors.

58. The forceps type apparatus according to claim 1, wherein the forceps type apparatus comprises a reverse tweezers.

59. The forceps type apparatus according to claim 1, wherein the forceps type apparatus comprises a scissors.

60. The forceps type apparatus according to claim 59, wherein a line extending between a space formed by the tip of the index finger and the tip of the middle finger and a dorsal surface of the distal interphalangeal joint (DIP) of the small finger of the hand, when the hand is in the Forceps Hand Position (FHP), is parallel to an axis passing centrally through the blades of the scissors.

61. A forceps type apparatus for use with a hand, comprising:
    a pair of radial arms including a radial end portion, the radial end portion for engaging a portion of the radial side of the palmar surface of the hand;
    a pair of ulnar arms including an ulnar end portion, the ulnar end portion for engaging a portion of the ulnar side of the palmar surface of the hand; and
    a pair of distal legs, with the pair of distal legs extending from at least one of the pair of radial arms and the pair of ulnar arms, and with the pair of distal legs for respectively receiving the thumb of the hand and at least one of the index finger of the hand and the middle finger of the hand, when the radial end portion of the pair of radial arms engages a portion of the radial side of the palmar surface of the hand and the ulnar end portion of the pair of ulnar arms engages a portion of the ulnar side of the palmar surface of the hand,
    wherein the radial end portion of the pair of radial arms and the ulnar end portion of the pair of ulnar arms engage corresponding portions of the radial side and the ulnar side of the palmar surface of the hand to position the forceps type apparatus within the hand without placing substantial pressure on a surface of the hand located over the carpal tunnel.

62. The forceps type apparatus according to claim 61, wherein the forceps type apparatus is made of a material such that the forceps type apparatus has a spring-like nature so as to selectively open after closing.

63. The forceps type apparatus according to claim 61, further comprising a working end at the distal end of at least one of the pair of distal legs.

64. The forceps type apparatus according to claim 63, wherein an implement is selectively attached to or detached from the working end of a corresponding distal leg.

65. The forceps type apparatus according to claim 64, wherein each implement is selectively attached to or detached from the working end of the corresponding distal leg by a suitable connection means.

66. The forceps type apparatus according to claim 64, wherein the implement is for grasping, pinching or cutting.

67. The forceps type apparatus according to claim 61, wherein the radial end portion and the ulnar end portion engage respective portions of the palmar surface of the hand so as to position the forceps type apparatus within the hand without engaging a surface of the hand located over the carpal tunnel.

68. The forceps type apparatus to claim 61, wherein the forceps type apparatus is generally of a Y shape, an asymmetrical Y shape or a sling-shot shape configuration.

69. The forceps type apparatus according to claim 61, further comprising a connection area from which extend the pair of radial arms, the pair of ulnar arms and the pair of distal legs.

70. The forceps type apparatus or handle according to claim 69, wherein the connection area includes a rotational mechanism for rotational movement of at least one of the pair of radial arms and the pair of ulnar arms.

71. The forceps type apparatus according to claim 70, wherein the rotational mechanism provides an angular range for the rotational movement.

72. The forceps type apparatus according to claim 61, wherein the forceps type apparatus includes at least one support area for supporting the forceps type apparatus when the hand is holding the forceps type apparatus, wherein the at least one support area includes a support area on at least one of the radial end portion for engaging the radial side of the palmar surface of the hand and the ulnar end portion for engaging the ulnar side of the palmar surface of the hand.

73. The forceps type apparatus according to claim 61, wherein the pair of ulnar arms includes at least one contact area for receiving at least one of the ring finger and the small finger of the hand.

74. The forceps type apparatus according to claim 61, wherein the pair of ulnar arms includes a ring finger contact area for receiving the ring finger of the hand and a small finger contact area for receiving the small finger of the hand.

75. The forceps type apparatus according to claim 74, wherein a step portion is positioned on the pair of ulnar arms between the ring finger contact area and the small finger contact area to conform the palmar surface of the ring finger to the ring finger contact area and the palmar surface of the small finger to the small finger contact area.

76. The forceps type apparatus according to claim 61, wherein at least one of the pair of radial arms and the pair of ulnar arms includes an extension for adjusting the forceps type apparatus to correspond to a hand size.

77. The forceps type apparatus according to claim 76, wherein each extension is selectively added to a corresponding one of the pair of radial arms or the pair of ulnar arms for adjusting the forceps type apparatus to correspond to a hand size.

78. The forceps type apparatus according to claim 76, wherein each extension can include a plurality of shapes for respectively engaging a corresponding portion of the radial side of the palmar surface of the hand or for engaging a corresponding portion of the ulnar side of the palmar surface of the hand.

79. The forceps type apparatus according to claim 78, wherein the plurality of shapes for a corresponding extension can include generally round shape.

80. The forceps type apparatus according to claim 61, further comprising a spring mechanism positioned between the pair of distal legs for maintaining the forceps type apparatus in a resting position.

81. The forceps type apparatus according to claim 61, further comprising a clamping mechanism engaging the pair of distal legs for selectively maintaining a range of positions for the forceps type apparatus.

82. The forceps type apparatus according to claim 61, wherein the forceps type apparatus comprises at least one ring member for receiving a corresponding at least one of the thumb or the long fingers of the hand.

83. The forceps type apparatus according to claim 82, further comprising at least one ring member positioned on each of the pair of distal legs for enabling the pair of distal legs of the forceps type apparatus to maintain a spread apart position.

84. The forceps type apparatus according to claim 61, wherein the width of the distal end of at least one of the pair of distal legs corresponds to the width across the long fingers of the hand for maximizing the pinch strength attainable when the thumb is positioned to centrally oppose the long fingers of the hand.

85. The forceps type apparatus according to claim 61, wherein the forceps type apparatus includes means for changing a side to side motion of the distal legs into a direction of motion that is oriented perpendicular to the side to side motion of the distal legs.

86. The forceps type apparatus according to claim 61, wherein the forceps type apparatus includes means for changing the motion of the distal legs into a motion for a working end of the forceps type apparatus.

87. The forceps type apparatus according to claim 86, wherein the means for changing the motion includes means for rotational movement for rotating the position of the working end of the forceps type apparatus.

88. The forceps type apparatus according to claim 86, wherein the means for changing the motion comprises a fixed member positioned in extending relation from the radial end portion of the pair of radial arms, and a sliding member positioned adjacent to the fixed member, with the movement of the distal legs moving the sliding member for activating the motion for the working end.

89. The forceps type apparatus according to claim 88, wherein the means for changing the motion further comprises at least one brace member for movement of the sliding member for activating the motion for the working end.

90. The forceps type apparatus according to claim 89, wherein a corresponding brace member is attached to the forceps type apparatus by a corresponding hinge member and to the sliding member by a corresponding hinge member for moving the sliding member to activate the motion for the working end.

91. The forceps type apparatus according to claim 90, wherein the hinge member attached to the forceps type apparatus is positioned distally relative to the hinge member attached to the sliding member.

92. The forceps type apparatus according to claim 90, wherein the hinge member attached to the forceps type apparatus is positioned proximally relative to the hinge member attached to the sliding member.

93. The forceps type apparatus according to claim 90, wherein the means for changing the motion further comprises a first spring member attached to the sliding member and attached to the forceps type apparatus.

94. The forceps type apparatus according to claim 93, wherein the means for changing the motion further comprises a second spring member attached to the fixed member and attached to the sliding member of the forceps apparatus.

95. The forceps type apparatus according to claim 94, wherein the hinge member attached to the forceps type apparatus is positioned distally relative to the hinge member attached to the sliding member.

96. The forceps type apparatus according to claim 94, wherein the working end comprises a scalpel, the scalpel comprises the fixed member, and the sliding member comprises a retractable guard for selectively retracting and exposing a blade of the scalpel.

97. The forceps type apparatus according to claim 94, wherein the working end comprises a tool, the tool comprises the fixed member, and the sliding member comprises a retractable guard for selectively surrounding and exposing the tool.

98. The forceps type apparatus according to claim 94, wherein the working end comprises the fixed member and the sliding member comprises a retractable guard for selectively surrounding and exposing the working end.

99. The forceps type apparatus according to claim 88, wherein the working end comprises a scalpel, the scalpel comprises the fixed member, and the sliding member comprises a retractable guard for selectively retracting and exposing a blade of the scalpel.

100. The forceps type apparatus according to claim 88, wherein the working end comprises a tool, the tool comprises the fixed member, and the sliding member comprises a retractable guard for selectively surrounding and exposing the tool.

101. The forceps type apparatus according to claim 88, wherein the working end comprises the fixed member and the sliding member comprises a retractable guard for selectively surrounding and exposing the working end.

102. The forceps type apparatus according to claim 86, wherein the means for changing the motion comprises a fixed member positioned with the forceps type apparatus and a sliding member positioned adjacent to the fixed member, with the sliding member being linked with the working end for activating the motion for the working end.

103. The forceps type apparatus according to claim 102, wherein the working end comprises a scalpel, the scalpel comprises the fixed member, and the sliding member comprises a retractable guard for selectively retracting and exposing a blade of the scalpel member.

104. The forceps type apparatus according to claim 102, wherein the working end comprises a tool, the tool comprises the fixed member, and the sliding member comprises a retractable guard for selectively surrounding and exposing the tool.

105. The forceps type apparatus according to claim 86, wherein the working end of the forceps type apparatus comprises a surgical tool having a retractable guard for selectively surrounding and exposing the working end of the surgical tool.

106. The forceps type apparatus according to claim 61, wherein the forceps type apparatus comprises a scalpel having a retractable guard for selectively surrounding and exposing the scalpel.

107. The forceps type apparatus according to claim 61, wherein the forceps type apparatus comprises a tool.

108. The forceps type apparatus according to claim 61, wherein the forceps type apparatus comprises a surgical tool.

109. The forceps type apparatus according to claim 61, wherein the forceps type apparatus comprises an endoscopic surgical tool.

110. The forceps type apparatus according to claim 61, wherein the forceps type apparatus comprises a microscissors.

111. The forceps type apparatus according to claim 61, wherein the forceps type apparatus comprises a reverse tweezers.

112. The forceps type apparatus according to claim 61, wherein the forceps type apparatus comprises a scissors.

113. The forceps type apparatus according to claim 112, wherein a line extending between a space formed by the tip of the index finger and the tip of the middle finger and a dorsal surface of the distal interphalangeal joint (DIP) of the small finger of the hand, when the hand is in the Forceps Hand Position (FHP), is parallel to an axis passing centrally through the blades of the scissors.

* * * * *

UNITED STATES PATENT AND TRADEMARK OFFICE
CERTIFICATE OF CORRECTION

PATENT NO. : 6,944,914 B2 Page 1 of 1
APPLICATION NO. : 10/420872
DATED : September 20, 2005
INVENTOR(S) : Tillim It is certified that error appears in the above-identified patent and that said Letters Patent is hereby corrected as shown below:

Col. 30 lines 58-63
Please delete claim 36 and the corrected claim 36 as follows:

36. The forceps type apparatus according to claim 35, wherein a corresponding brace member is attached to the forceps type apparatus by a corresponding hinge member and to the sliding member by a corresponding hinge member for moving the sliding member to activate the motion for the working end.

Signed and Sealed this

Twenty-sixth Day of June, 2007

JON W. DUDAS
*Director of the United States Patent and Trademark Office*